United States Patent
Ay et al.

(10) Patent No.: US 12,274,505 B2
(45) Date of Patent: Apr. 15, 2025

(54) BODY ENGAGERS AND METHODS OF USE

(71) Applicant: Fited, Inc., Teaneck, NJ (US)

(72) Inventors: Mehmet Erdem Ay, Teaneck, NJ (US); Caroline Jane Wolfe, Florham Park, NJ (US)

(73) Assignee: Mehmet Erdem Ay, Teaneck, NJ (US)

( * ) Notice: Subject to any disclaimer, the term of this patent is extended or adjusted under 35 U.S.C. 154(b) by 824 days.

(21) Appl. No.: 16/669,136

(22) Filed: Oct. 30, 2019

(65) Prior Publication Data

US 2020/0129237 A1    Apr. 30, 2020

Related U.S. Application Data

(60) Provisional application No. 62/752,491, filed on Oct. 30, 2018.

(51) Int. Cl.
| | |
|---|---|
| *A61B 34/10* | (2016.01) |
| *A61B 5/103* | (2006.01) |
| *G06T 17/00* | (2006.01) |
| *G06T 19/00* | (2011.01) |
| *G06T 19/20* | (2011.01) |
| *G16H 50/20* | (2018.01) |
| *G16H 70/60* | (2018.01) |
| *A61F 2/48* | (2006.01) |
| *A61F 5/01* | (2006.01) |

(52) U.S. Cl.
CPC .............. *A61B 34/10* (2016.02); *A61B 5/103* (2013.01); *G06T 17/00* (2013.01); *G06T 19/006* (2013.01); *G06T 19/20* (2013.01); *G16H 50/20* (2018.01); *G16H 70/60* (2018.01); *A61B 2034/108* (2016.02); *A61F 2/488* (2021.08); *A61F 5/01* (2013.01); *G06T 2210/41* (2013.01)

(58) Field of Classification Search
CPC ........ A61B 34/10; G16H 70/60; G16H 50/20; G06T 7/0012
USPC ........................................... 600/587
See application file for complete search history.

(56) References Cited

U.S. PATENT DOCUMENTS

| | | | |
|---|---|---|---|
| 2003/0014692 A1* | 1/2003 | James | G06F 11/2263 714/E11.158 |
| 2007/0168152 A1 | 7/2007 | Matov et al. | |
| 2013/0166256 A1* | 6/2013 | Wirx-Speetjens | B33Y 50/00 703/1 |
| 2017/0079828 A1* | 3/2017 | Pedtke | G05B 19/4099 |
| 2017/0323064 A1* | 11/2017 | Bates | G16H 50/20 |
| 2018/0008378 A1 | 1/2018 | Raghavan et al. | |
| 2018/0055660 A1* | 3/2018 | MacMahon | A61B 5/4561 |
| 2018/0147062 A1* | 5/2018 | Ay | A61F 2/30942 |

(Continued)

FOREIGN PATENT DOCUMENTS

WO    WO 2020/092571    5/2020

OTHER PUBLICATIONS

"A 3D visualization tool for the design and customization of spinal braces", D. Fortin et al., Computerized Medical Imaging and Graphics, vol. 31, Issue 8, Dec. 2007, pp. 614-624.*

(Continued)

*Primary Examiner* — Javid A Amini
(74) *Attorney, Agent, or Firm* — Levine Bagade Han LLP

(57) ABSTRACT

Systems, devices and methods are disclosed for addressing body conditions, monitoring body conditions and adapting treatment of internal and/or external body conditions.

43 Claims, 28 Drawing Sheets

(56) References Cited

U.S. PATENT DOCUMENTS

2020/0077892 A1* 3/2020 Tran ..................... A61B 5/1117

OTHER PUBLICATIONS

Cabitza, F. et al. "Machine Learning in Orthopedics: A Literature Review," Frontiers in Bioengineering and Biotechnology, vol. 6, No. 75, pp. 1-20, Jun. 27, 2018.

* cited by examiner

Sit behind the patient. You're going to slide your device down the patient's spine while they're in a forward bend.

The patient needs to be shirtless or in a bra.

You need enough light take a crisp and clear recording.

| Exemplary Data Acquired | | | Example Physical Parameters 502 | Example Body Conditions 504 | Device Fit Requirements 506 | Example Devices 150 |
|---|---|---|---|---|---|---|
| frontal plane | sagittal plane | axial plane | | | | |
| frontal x-ray (e.g., Fig. 7A) | sagittal x-ray (e.g., Figs. 7B and 7C) | axial x-ray (e.g., see Fig. 7D) | horizontal dimensions of the torso (hip, waist, underbust, etc.) in the frontal and sagittal planes, distance from the apex of the spinal curves to CSVL | scoliosis, abnormal curvature of the spine | Spine curvature in degrees, body dimensions like chest measurement, hip measurement | scoliosis brace (e.g., Fig. 12A) |
| frontal x-ray (e.g., Fig. 8A), frontal picture (e.g., Fig. 8B) | sagittal x-ray (e.g., Fig. 8C), sagittal picture (e.g., Figs. 8D and 8E) | axial x-ray(e.g., Fig. 8F) | length of the leg (angle of full knee flexion, extension), frontal and sagittal angle between tibia and humerus in standing position and during gait, circumference around thigh, knee, and/or calf, horizontal dimensions of thigh, knee, and calf in frontal and sagittal view | hyperextension, valgus knee, varus knee, arthritis, meniscus injury, ACL injury, post knee surgery, "runner's knee" (patellofemoral malalignment, chondromalacia patella, and iliotibial band syndrome) | length of the leg that the brace must cover, mobility of knee joint (angle of full knee flexion extension), frontal and sagittal angle between tibia and humerus in standing position and during gait, circumference around thigh, knee, and/or calf | knee brace (e.g., Fig. 12B) |
| frontal x-ray (e.g., Fig. 9A) | sagittal x-ray (e.g., Fig. 9B) | axial x-ray | height and width of hip socket, length of femoral neck, angle of femoral neck from femur and pelvis | osteoarthritis, rheumatoid arthritis, hip fracture to a certain extent, septic arthritis, ankylosing spondylitis, bone displasia, unusual bone growth, avascular necrosis of the hip, death of any part of hip joint, failed previous hip implants/replacements | measurements of hip socket, angle of femoral neck from femur and pelvis, "Q angle" | hip implant (e.g., Fig. 12C) |
| frontal x-ray (e.g., Fig. 10A) | sagittal x-ray (e.g., Fig. 10B) | axial x-ray(e.g., Fig. 10C | length of foot, width of foot at various locations along the length of the foot, static angle between foot and ankle in sagittal and frontal plane during standing, dynamic angle between foot and ankle in sagittal and frontal plane during gait, pressure map of foot contact with ground during standing and during gait, arch height of foot, angle of big toe relative to rest of the foot | runner, walker | measurement of foot dimensions, pressure map of foot on ground while running or walking | Running shoes/ any shoes (e.g., Fig. 12D) |
| frontal picture (e.g., Figs. 11B and 11C), frontal x-ray | sagittal picture (e.g., Figs. 11B and 11C), sagittal x-ray | axial x-ray | desired angle/mobility between forearm and upper arm, desired angle/mobility between shoulder and torso in all 3 dimensions, circumference of upper arm, elbow, forearm, length of the arm that the brace must cover, horizontal dimensions of upper arm, elbow, and lower arm in frontal and sagittal view | pinched nerve, "swimmer's shoulder" (impingement syndrome, etc.), "tennis elbow" (lateral epicondylitis), "golfer's elbow"(medial epicondylitis), fracture of humerus, radius, or ulna | pressure, desired angle between forearm and upper arm, mobility of elbow and /or shoulder joint, circumference of upper are, elbow, and/or forearm, length of the arm that the brace must cover, amount of stabilization needed for healing. | arm brace (e.g., Fig. 12E) |
| frontal x-ray/MRI | sagittal x-ray/MRI | axial x-ray/MRI/ CT scan for imaging of spine | length of neck, circumference of neck | cervical spine or spinal cord injury, whiplash, neck soft tissue injury | length of neck, circumference of neck, range of motion of neck in all 3 planes (coronal, sagittal, axial) | neck brace |
| frontal x-ray/MRI | sagittal x-ray/MRI | axial x-ray/MRI | length of foot, width of foot at various locations along the length of the foot, static angle between foot and ankle in sagittal and frontal plane during standing, dynamic angle between foot and ankle in sagittal and frontal plane during gait, pressure map of foot contact with ground during standing and during gait, arch height of foot, angle of big toe relative to rest of the foot | overpronation, oversupinatioon, achilles injuries (heel lift can be used), plantar faciitis, bunion, arthritis, metatarsophalangeal joint sprain, sesamoiditis, fracture of the bones of the feet including, but not limited to : metatarsals, calcaneus, cuneiform bones, navicular bone), collapsed arches | dimensions of foot, static angle between foot and ankle in sagittal and frontal plane during standing, dynamic angle between foot and ankle in sagittal and frontal plane during gait, pressure map of foot contact with ground during standing and during gait, arch height of foot, angle of big toe relative to rest of the foot | foot orthosis (e.g., Fig. 12D) |
| frontal x-ray/MRI | sagittal x-ray/MRI | axial x-ray/MRI | length of absent limb or portion of body (based on the opposite side with limb, assuming only one side is absent), topography, circumference of the end of the leg at which the prosthesis will attach to, length of the foot on the present side, | foot amputation, toe amputation, leg amputation proximal, distal, or through knee joint, congenital defects resulting in absent foot, toe, or leg | length of absent limb or portion of body (based on the opposite side with limb, assuming only one side is absent), topography, circumference or any measurement of end of body at which the prosthesis will attach to, activity requirements | foot/leg prosthesis |
| frontal x-ray/MRI | sagittal x-ray/MRI | axial x-ray/MRI | length of absent limb or portion of body (based on the opposite side with limb, assuming only one side is absent), topography, circumference of the end of the arm at which the prosthesis will attach to, length of the hand | arm amputation proximal, distal, or through elbow joint, or through shoulder joint, finger or hand amputation | length of absent limb or portion of body (based on the opposite side with limb, assuming only one side is absent), topography, circumference, or any measurement of end of body at which the prosthesis will attach to, activity requirements | arm/hand prosthesis |

| Exemplary Data Acquired | | | Example Physical Parameters 502 |
|---|---|---|---|
| frontal plane | sagittal plane | axial plane | |
| frontal x-ray (e.g., Fig. 7A) | sagittal x-ray (e.g., Figs. 7B and 7C) | axial x-ray (e.g., see Fig. 7D) | horizontal dimensions of the torso (hip, waist, underbust, etc.) in the frontal and sagittal planes, distance from the apex of the spinal curves to CSVL |
| frontal x-ray (e.g., Fig. 8A), frontal picture (e.g., Fig. 8B) | sagittal x-ray (e.g., Fig. 8C), sagittal picture (e.g., Figs. 8D and 8E) | axial x-ray(e.g., Fig. 8F) | length of the leg that the brace must cover, mobility of knee joint (angle of full knee flexion ,extension), frontal and sagittal angle between tibia and humerus in standing position and during gait, circumference around thigh, knee, and/or calf, horizontal dimensions of thigh, knee, and calf in frontal and sagittal view |
| frontal x-ray (e.g., Fig. 9A) | sagittal x-ray (e.g., Fig. 9B) | axial x-ray | height and width of hip socket, length of femoral neck, angle of femoral neck from femur and pelvis |
| frontal x-ray (e.g., Fig. 10A) | sagittal x-ray (e.g., Fig. 10B) | axial x-ray(e.g., Fig. 10C | length of foot, width of foot at various locations along the length of the foot, static angle between foot and ankle in sagittal and frontal plane during standing, dynamic angle between foot and ankle in sagittal and frontal plane during gait, pressure map of foot contact with ground during standing and during gait, arch height of foot, angle of big toe relative to rest of the foot |
| frontal picture (e.g., Fig. 11A), frontal x-ray | sagittal picture (e.g., Figs. 11B and 11C), sagittal x-ray | axial x-ray | desired angle/mobility between forearm and upper arm, desired angle/mobility between shoulder and torso in all 3 dimensions, circumference of upper arm, elbow, forearm, length of the arm that the brace must cover, horizontal dimensions of upper arm, elbow, and lower arm in frontal and sagittal view |
| frontal x-ray/ MRI | sagittal x-ray/MRI | axial x-ray/ MRI/CT scan for imaging of spine | length of neck, circumference of neck |
| frontal x-ray/ MRI | sagittal x-ray/MRI | axial x-ray/ MRI | length of foot, width of foot at various locations along the length of the foot, static angle between foot and ankle in sagittal and frontal plane during standing, dynamic angle between foot and ankle in sagittal and frontal plane during gait, pressure map of foot contact with ground during standing and during gait, arch height of foot, angle of big toe relative to rest of the foot |
| frontal x-ray/ MRI | sagittal x-ray/MRI | axial x-ray/ MRI | length of absent limb or portion of body (based on the opposite side with limb, assuming only one side is absent), topography, circumference of the end of the leg at which the prosthesis will attach to, length of the foot on the present side, |
| frontal x-ray/MRI | sagittal x-ray/MRI | axial x-ray/ MRI | length of absent limb or portion of body (based on the opposite side with limb, assuming only one side is absent), topography, circumference of the end of the arm at which the prosthesis will attach to, length of the hand |

FIG. 6A1-1

| Example Body Conditions 504 | Device Fit Requirements 506 | Example Devices 150 |
|---|---|---|
| scoliosis, abnormal curvature of the spine | spine curvature in degrees, body dimensions like chest measurement, hip measurement | scoliosis brace (e.g., Fig. 12A) |
| hyperextension, valgus knee, varus knee, arthritis, meniscus injury, ACL injury, post knee surgery, "runner's knee" (patellofemoral malalignment, chondromalacia patella, and iliotibial band syndrome) | length of the leg that the brace must cover, mobility of knee joint (angle of full knee flexion ,extension), frontal and sagittal angle between tibia and humerus in standing position and during gait, circumference around thigh, knee, and/or calf | knee brace (e.g., Fig. 12B) |
| osteoarthritis, rheumatoid arthritis, hip fracture to a certain extent, septic arthritis, ankylosing spondylitis, bone displasia, unusual bone growth, avascular necrosis of the hip, death of any part of hip joint, failed previous hip implants/replacements | measurements of hip socket, angle of femoral neck from femur and pelvis, "Q angle" | hip implant (e.g., Fig. 12C) |
| runner, walker | measurement of foot dimensions, pressure map of foot on ground while running or walking | Running shoes/any shoes (e.g., Fig. 12D) |
| pinched nerve, "swimmer's shoulder" (impingement syndrome, etc.), "tennis elbow" (lateral epicondylitis), "golfer's elbow"(medial epicondylitis), fracture of humerus, radius, or ulna | pressure, desired angle between forearm and upper arm, mobility of elbow and /or shoulder joint, circumference of upper are, elbow, and/or forearm, length of the arm that the brace must cover, amount of stabilization needed for healing, | arm brace (e.g., Fig. 12E) |
| cervical spine or spinal cord injury, whiplash, neck soft tissue injury | length of neck, circumference of neck, range of motion of neck in all 3 planes (coronal, sagittal, axial) | neck brace |
| overpronation, oversupinatioon, achilles injuries (heel lift can be used), plantar faciitis, bunion, arthritis, metatarsophalangeal joint sprain, sesamoiditis, fracture of the bones of the feet including, but not limited to : metatarsals, calcaneus, cuneiform bones, navicular bone), collapsed arches | dimensions of foot, static angle between foot and ankle in sagittal and frontal plane during standing, dynamic angle between foot and ankle in sagittal and frontal plane during gait, pressure map of foot contact with ground during standing and during gait, arch height of foot, angle of big toe relative to rest of the foot | foot orthosis (e.g., Fig. 12D) |
| foot amputation, toe amputation, leg amputation proximal, distal, or through knee joint, congenital defects resulting in absent foot, toe, or leg | length of absent limb or portion of body (based on the opposite side with limb, assuming only one side is absent), topography, circumference or any measurement of end of body at which the prosthesis will attach to, activity requirements | foot/leg prosthesis |
| arm amputation proximal, distal, or through elbow joint, or through shoulder joint, finger or hand amputation | length of absent limb or portion of body (based on the opposite side with limb, assuming only one side is absent), topography, circumference, or any measurement of end of body at which the prosthesis will attach to, activity requirements | arm/hand prosthesis |

| Exemplary Data Acquired | | | Example Physical Parameters 502 |
|---|---|---|---|
| frontal plane | sagittal plane | axial plane | |
| frontal x-ray/MRI | sagittal x-ray/MRI | axial x-ray/MRI at joint interface | width and length of the lateral/medial condyle of femur and medial/lateral condyle of tibia, as well as topography. width/length/height measurement of amount of meniscus present, forces within the knee joint (this is do-able only if the person already has a knee implant), frontal and sagittal horizontal measurements of the tibia and femur and circumference of both |
| frontal x-ray/MRI | sagittal x-ray/MRI | sagittal x-ray/MRI | height and width of glenoid cavity, height and width of humerus head and tuberosities, topography of all, coordinates of fracture location |
| frontal x-ray of vertebra that needs bone screw | sagittal x-ray of vertebra that needs bone screw | axial x-ray of vertebra that needs bone screw | circumference, diameter, height, length, width, of vertebra and vertebral body and disks, stage of bone maturity (Risser 1-5), Cobb angle of spine, rotation of vertebra |
| frontal MRI to see thickness of tissue | sagittal MRI to see thickness of tissue | axial MRI to see thickness of tissue | length of incision needed, depth of incision, strength of material though which scalpel will cut |
| frontal x-ray | sagittal x-ray | axial x-ray | measurement of horizontal distance across chest in frontal plane and in sagittal plane, measurement of distance from one shoulder to the other, measurement of horizontal distance across hips in frontal and sagittal plane, angle of lordosis and kyphosis |
| frontal x-ray | sagittal x-ray | axial x-ray | depth and width and height of eye socket, topography of face, cross section dimensions of sinuses, ear canal, width of gumline |
| frontal x-ray | sagittal x-ray | axial x-ray | width, length of jaw, palete |
| frontal x-ray | sagittal x-ray | axial x-ray | width of gumline, length and width of palete, height, length, width of missing teeth |
| frontal MRI | sagittal MRI | axial MRI | height, width, length of uterus, angle at which uterus sits in body, length and width of cervix |
| frontal x-ray | sagittal x-ray | axial x-ray | surface area of skin |
| frontal MRI | sagittal MRI | axial MRI | location of problem area |

| Example Body Conditions 504 | Device Fit Requirements | Example Devices 150 |
|---|---|---|
| osteoarthritis, rheumatoid arthritis, knee fracture to a certain extent, septic arthritis, ankylosing spondylitis, bone dysplasia, unusual bone growth, avascular necrosis, death of any part of knee joint, wearing away of meniscus, failed previous knee implants/replacements | measurements of lateral/ medial condyle of femur, measurements of medial/ lateral condyle of tibia, topography of the condyles of the femur and the tibia, measurements within the knee joint, measurement of amount of meniscus present | knee implant |
| Osteoarthritis, degenerative joint disease, Rheumatoid arthritis, Rotator Cuff Tear Arthropathy, Avascular Necrosis (Osteonecrosis), Severe Fractures, failed previous shoulder replacements/implants | measurements of glenoid, humerus head, tuberosities, rotator cuff capabilities/force output, fracture location and measurements to that coordinate | shoulder implant |
| scoliosis, abnormal curvature of the spine, fracture of any vertebrae | size and dimensions of vertebra and discs, stage of bone maturity, angle of curvature of spine | spine screw |
| need for a scalpel for different patient sizes | size of incision needed, material through which scalpel will cut, depth of incision needed | hip surgery scalpel/scalpel in general |
| poor posture, hyperlordosis, hyperkyphosis | body dimensions like chest measurement, shoulder measurement, hip measurement, angle of posture, lordosis, or kyphosis | back/shoulder brace |
| absent eyeball, nose structure, teeth, ear structure | measurements of eye socket, face, sinuses, sinus openings, ear canal, head, jaw, gumline, mouth palete | cosmetic prosthesis |
| malalignment of teeth, crooked teeth, too small palete | measurement of palete, mold of teeth in original position, measurement of jaw characteristics | dental orthosis |
| missing teeth, misaligned teeth | measurement of palete, gum line, dimensions of missing teeth | dental implants |
| patient wants to prevent pregnancy | measurement of uterus in all 3 dimensions, measurement of cervix | intrauterine devices |
| patient has a burn and needs a skin graft | measurement of area of skin needed | devices for tissue growth (e.g., tissue expanders under skin) |
| patient cannot perform desired motions | location of problem area | electrical stimulation devices (e.g., electrodes for stimulating tissue) |

FIG. 6A2

| Exemplary Data Acquired | | | Example Physical Parameters 502 |
|---|---|---|---|
| frontal plane | sagittal plane | axial plane | |
| frontal x-ray/ MRI | sagittal x-ray/ MRI | axial x-ray/ MRI at joint interface | width and length of the lateral/medial condyle of femur and medial/lateral condyle of tibia, as well as topography. width/length/height measurement of amount of meniscus present, forces within the knee joint (this is do-able only if the person already has a knee implant), frontal and sagittal horizontal measurements of the tibia and femur and circumference of both |
| frontal x-ray/ MRI | sagittal x-ray/ MRI | sagittal x-ray/ MRI | height and width of glenoid cavity, height and width of humerus head and tuberosities, topography of all, coordinates of fracture location |
| frontal x-ray of vertebra that needs bone screw | sagittal x-ray of vertebra that needs bone screw | axial x-ray of vertebra that needs bone screw | circumference, diameter, height, length, width, of vertebra and vertebral body and disks, stage of bone maturity (Risser 1-5), Cobb angle of spine, rotation of vertebra |
| frontal MRI to see thickness of tissue | sagittal MRI to see thickness of tissue | axial MRI to see thickness of tissue | length of incision needed, depth of incision, strength of material though which scalpel will cut |
| frontal x-ray | sagittal x-ray | axial x-ray | measurement of horizontal distance across chest in frontal plane and in sagittal plane, measurement of distance from one shoulder to the other, measurement of horizontal distance across hips in frontal and sagittal plane, angle of lordosis and kyhposis |
| frontal x-ray | sagittal x-ray | axial x-ray | depth and width and height of eye socket, topography of face, cross section dimensions of sinuses, ear canal, width of gumline |
| frontal x-ray | sagittal x-ray | axial x-ray | width, length of jaw, palete |
| frontal x-ray | sagittal x-ray | axial x-ray | width of gumline, length and width of palete, height, length, width of missing teeth |
| frontal MRI | sagittal MRI | axial MRI | height, width, length of uterus, angle at which uterus sits in body, length and width of cervix |
| frontal x-ray | sagittal x-ray | axial x-ray | surface area of skin |
| frontal MRI | sagittal MRI | axial MRI | location of problem area |

FIG. 6A2-1

| Example Body Conditions 504 | Device Fit Requirements | Example Devices 150 |
|---|---|---|
| osteoarthritis, rheumatoid arthritis, knee fracture to a certain extent, septic arthritis, ankylosing spondylitis, bone dysplasia, unusual bone growth, avascular necrosis, death of any part of knee joint, wearing away of meniscus, failed previous knee implants/ replacements | measurements of lateral/ medial condyle of femur, measurements of medial/ lateral condyle of tibia, topography of the condyles of the femur and the tibia, measurements within the knee joint, measurement of amount of meniscus present | knee implant |
| Osteoarthritis, degenerative joint disease, Rheumatoid arthritis, Rotator Cuff Tear Arthropathy, Avascular Necrosis (Osteonecrosis), Severe Fractures, failed previous shoulder replacements/implants | measurements of glenoid, humerus head, tuberosities, rotator cuff capabilities/force output, fracture location and measurements to that coordinate | shoulder implant |
| scoliosis, abnormal curvature of the spine, fracture of any vertebrae | size and dimensions of vertebra and discs, stage of bone maturity, angle of curvature of spine | spine screw |
| need for a scalpel for different patient sizes | size of incision needed, material through which scalpel will cut, depth of incision needed | hip surgery scalpel/scalpel in general |
| poor posture, hyperlordosis, hyperkyphosis | body dimensions like chest measurement, shoulder measurement, hip measurement, angle of posture, lordosis, or kyphosis | back/shoulder brace |
| absent eyeball, nose structure, teeth, ear structure | measurements of eye socket, face, sinuses, sinus openings, ear canal, head, jaw, gumline, mouth palete | cosmetic prosthesis |
| malalignment of teeth, crooked teeth, too small palate | measurement of palate, mold of teeth in original position, measurement of jaw characteristics | dental orthosis |
| missing teeth, misaligned teeth | measurement of palate, gum line, dimensions of missing teeth | dental implants |
| patient wants to prevent pregnancy | measurement of uterus in all 3 dimensions, measurement of cervix | intrauterine devices |
| patient has a burn and needs a skin graft | measurement of area of skin needed | devices for tissue growth (e.g., tissue expanders under skin) |
| patient cannot perform desired motions | location of problem area | electrical stimulation devices (e.g., electrodes for stimulating tissue) |

| Example body conditions 504 | Example Primary Conditions (P) and Secondary Conditions (S) | Example Thresholds for Treatment of Primary Condition |
|---|---|---|
| scoliosis, abnormal curvature of the spine | P: frontal plane Cobb angle<br>S: hypo or hyper kyphosis | For initial treatment: a Cobb angle over approx. 15-20 degrees. For second stage of treatment: Cobb angle at approx. 10 degrees while in this brace, the patient has spend significant time in this brace, and /or the patient has outgrown this brace. Third stage: 5 degrees toward 0. If angles remain static, brace adjustments can be made to decrease Cobb angle. |
| hyperextension, valgus knee, varus knee, arthritis, meniscus injury, ACL injury, post knee surgery, "runner's knee" (patellofemoral malalignment, chondromalacia patella, and iliotibial band syndrome) | P: valgus knee<br>S: foot pronation | Valgus knee of 15 degrees or higher for initial treatment. If knee valgus is 15 degrees or lower, that is ok. Ideally, the brace will reduce knee valgus by 50% with each brace adjustment or with each new brace and spend a sufficient amount of time in this brace, or grow out of the brace. |
| osteoarthritis, rheumatoid arthritis, hip fracture to a certain extent, septic arthritis, ankylosing spondylitis, none displasia, unusual bone growth, avascular necrosis of the hip, death of any part of hip joint, failed previous hip implants/ replacements | P: conditions 504 (e.g., this row, first column in this table)<br>S: knee problems | diagnosis of the conditions listed |
| runner, walker | P/S: a person looking for a personalized shoe is more likely to have foot issues, which means that they are more likely to also have knee issues and hip issues | any person can get this shoe, a condition is not needed, but, it will correct conditions if they exist |
| pinched nerve, "swimmer's shoulder" (impingement syndrome, etc.), "tennis elbow" (lateral epicondylitis), "golfer's elbow" (medial epicondylitis), fracture of humerus, radius, or ulna | P: arm fracture, torn ligament, muscle, or tendon | diagnosis of fracture of soft tissue injury |
| cervical spine or spinal cord injury, whiplash, neck soft tissue injury | P: any of the neck conditions 504 listed (e.g., this row, first column)<br>S: concussion, brain injury, back injury | diagnosis of conditions listed |
| overpronation, oversupination, achilles injuries (heel lift can be used), plantar faciitis, bunion, arthritis, metatarsophalangeal joint sprain, sesamoiditis, fracture of the bones of the feet including, but not limited to : metatarsals, calcaneus, cuneiform bones, navicular bone), collapsed arches | P: collapsed arch, pronation<br>S: back injury | arch heigh less than 3mm-5mm, orthotics will progressively increase the arch height to a normal height |

FIG. 6B1-2    600B

| Example Devices 150 | Example First and Second Positions/ Parameter Values | Monitoring (e.g., via sensors 152 and / or data acquisitions via the acquisition device 102) |
|---|---|---|
| scoliosis brace (e.g., Fig. 12A) | 1st value: 40 degree Cobb angle<br>2nd value: 20 degree Cobb angle | pressure detected by scoliosis brace, change in spine curvature |
| knee brace (e.g., Fig. 12B) | 1st value: valgus knee angle of 25 degrees<br>2nd value: valgus knee of angle 12.5 degrees | pressure, patient pain improvement rating, range of motion of knee, knee angle in normal stance (frontal and sagittal), intra-knee joint pressures, healing of tendons/ligaments/muscles |
| hip implant (e.g., Fig. 12C) | n/a, these implants should only be re-done if a problem occurs or an error was made | intra-joint forces, patient comfort and satisfaction, x-rays and imaging of joint to make sure in tact |
| Running shoes/any shoes (e.g., Fig. 12D) | maybe walker or runner has a low arch, cannot find shoes that fit his or her feet, etc. This shoe would fit the foot and correct any malformations with the foot. ex: low arch, high arch. | rate of injury, patient satisfaction, wear patterns of shoes |
| arm brace (e.g., Fig. 12E) | arm fractured, in displaced position and moveable. With the brace the arm is set back into a 90 degree elbow joint angle and secured in this position | pressure, patient pain improvement rating, range of motion of elbow or shoulder with or without pain, healing of fractures, healing of tendons/ligaments/ muscles |
| neck brace | correction of conditions listed | pressure, healing of fractures or spinal cord injuries or all injuries, patient pain rating during neck range of motion exercises in all 3 planes |
| foot orthosis | For collapsed arch:<br>1st value: arch height of 2mm<br>2nd value: arch height of 5mm | healing of fractures or injuries, patient pain improvement rating, change of angle of big toe relative to rest of foot, change of tactic angle between foot and ankle in sagittal and frontal plane during standing, change of dynamic angle between foot and ankle in sagittal and frontal plane during gait, change of pressure map of foot contact with ground during standing and during gait, change of arch height of foot |

FIG. 6B1

| Example body conditions 504 | Example Primary Conditions (P) and Secondary Conditions (S) | Example Thresholds for Treatment of Primary Condition |
|---|---|---|
| scoliosis, abnormal curvature of the spine | P: frontal plane Cobb angle<br>S: hypo or hyper kyphosis | For initial treatment: a Cobb angle over approx. 15-20 degrees. For second stage of treatment: Cobb angle at approx. 10 degrees while in this brace, the patient has spend significant time in this brace, and /or the patient has outgrown this brace. Third stage: 5 degrees toward 0. If angles remain static, brace adjustments can be made to decrease Cobb angle. |
| hyperextension, valgus knee, varus knee, arthritis, meniscus injury, ACL injury, post knee surgery, "runner's knee" (patellofemoral malalignment, chrondromalacia patella, and iliotibial band syndrome) | P: valgus knee<br>S: foot pronation | Valgus knee of 15 degrees or higher for initial treatment. If knee valgus is 15 degrees or lower, that is ok. Ideally, the brace will reduce knee valgus by 50% with each brace adjustment or with each new brace and spend a sufficient amount of time in this brace, or grow out of the brace. |
| osteoarthritis, rheumatoid arthritis, hip fracture to a certain extent, septic arthritis, ankylosing spondylitis, none displasia, unusual bone growth, avascular necrosis of the hip, death of any part of hip joint, failed previous hip implants/replacements | P: conditions 504 (e.g., this row, first column in this table)<br>S: knee problems | diagnosis of the conditions listed |
| runner, walker | P/S: a person looking for a personalized shoe is more likely to have foot issues, which means that they are more likely to also have knee issues and hip issues | any person can get this shoe, a condition is not needed, but, it will correct conditions if they exist |
| pinched nerve, "swimmer's shoulder" (impingement syndrome, etc.), "tennis elbow" (lateral epicondylitis), "golfer's elbow"(medial epicondylitis), fracture of humerus, radius, or ulna | P: arm fracture, torn ligament, muscle, or tendon | diagnosis of fracture of soft tissue injury |
| cervical spine or spinal cord injury, whiplash, neck soft tissue injury | P: any of the neck conditions 504 listed (e.g., this row, first column)<br>S: concussion, brain injury, back injury | diagnosis of conditions listed |
| overpronation, oversupinatioon, achilles injuries (heel lift can be used), plantar faciitis, bunion, arthritis, metatarsophalangeal joint sprain, sesamoiditis, fracture of the bones of the feet including, but not limited to : metatarsals, calcaneus, cuneiform bones, navicular bone), collapsed arches | P: collapsed arch, pronation<br>S: back injury | arch heigh less than 3mm-5mm, orthodics will progressively increase the arch height to a normal height |

FIG. 6B1-1

| Example Devices 150 | Example First and Second Positions/ Parameter Values | Monitoring (e.g., via sensors 152 and / or data acquisitions via the acquisition device 102) |
|---|---|---|
| scoliosis brace (e.g., Fig. 12A) | 1st value: 40 degree Cobb angle<br>2nd value: 20 degree Cobb angle | pressure detected by scoliosis brace, change in spine curvature |
| knee brace (e.g., Fig. 12B) | 1st value: valgus knee angle of 25 degrees<br>2nd value: valgus knee of angle 12.5 degrees | pressure, patient pain improvement rating, range of motion of knee, knee angle in normal stance (frontal and sagittal), intra-knee joint pressures, healing of tendons/ligaments/muscles |
| hip implant (e.g., Fig. 12C) | n/a, these implants should only be re-done if a problem occurs or an error was made | intra-joint forces, patient comfort and satisfaction, x-rays and imaging of joint to make sure in tact |
| Running shoes/ any shoes (e.g., Fig. 12D) | maybe walker or runner has a low arch, cannot find shoes that fit his or her feet, etc. This shoe would fit the foot and correct any malformations with the foot. ex: low arch, high arch. | rate of injury, patient satisfaction, wear patterns of shoes |
| arm brace (e.g., Fig. 12E) | arm fractured, in displaced position and moveable. With the brace the arm is set back into a 90 degree elbow joint angle and secured in this position | pressure, patient pain improvement rating, range of motion of elbow or shoulder with or without pain, healing of fractures, healing of tendons/ ligaments/muscles |
| neck brace | correction of conditions listed | pressure, healing of fractures or spinal cord injuries or all injuries, patient pain rating during neck range of motion exercises in all 3 planes |
| foot orthosis | For collapsed arch:<br>1st value: arch height of 2mm<br>2nd value: arch height of 5mm | healing of fractures or injuries, patient pain improvement rating, change of angle of big toe relative to rest of foot, change of tactic angle between foot and ankle in sagittal and frontal plane during standing, change of dynamic angle between foot and ankle in sagittal and frontal plane during gait, change of pressure map of foot contact with ground during standing and during gait, change of arch height of foot |

FIG. 6B1-2

| Example body conditions 504 | Example Primary Conditions (P) and Secondary Conditions (S) | Example Thresholds for Treatment of Primary Condition | Example Devices 150 | Example First and Second Positions/ Parameter Values | Monitoring (e.g., via sensors 152 and / or data acquisitions via the acquisition device 102) |
|---|---|---|---|---|---|
| foot amputation, toe amputation, leg amputation proximal, distal, or through knee joint, congenital defects resulting in absent foot, toe, or leg | | | foot/leg prosthesis | | pressures, forces, moisture, skin condition within prosthesis socket, patient comfort, monitoring angles between joints so that they resemble normal gait, patient satisfaction with device |
| arm amputation proximal, distal, or through elbow joint, or through shoulder joint, finger or hand amputation | | | arm/hand prosthesis | | pressures, forces, moisture, skin condition within prosthesis socket, patient comfort and satisfaction with device |
| osteoarthritis, rheumatoid arthritis, knee fracture to a certain extent, septic arthritis, ankylosing spondylitis, bone displasia, unusual bone growth, avascular necrosis, death of any part of knee joint, wearing away of meniscus, failed previous knee implants/ replacements | P: conditions 504 (e.g., this row, first column in this table) S: hip problems | diagnosis of the conditions listed in this row | knee implant | n/a, these implants should only be re-done if a problem occurs or error was made | intra-joint forces, patient comfort and satisfaction, x-rays and imaging of joint to make sure in tact |
| Osteoarthritis, degenerative joint disease, Rheumatoid Arthritis, Rotator Cuff Tear Arthropathy, Avascular Necrosis (Osteonecrosis), Severe Fractures, failed previous shoulder replacements/implants | | diagnosis of the conditions listed in this row | shoulder implant | n/a, these implants should only be re-done if a problem occurs or an error was made | intra-joint forces, patient comfort and satisfaction, x-rays and imaging of joint to make sure in tact |
| scoliosis, abnormal curvature of the spine, fracture of any vertebrae | P: conditions 504 (e.g., this row, first column in this table) S: various types of spinal problems, poor posture | having any of the conditions listed in this row | spine screw | n/a only replaced with significant patient growth | changed angle of curvature of spine, screw maintaining its position |
| need for a scalpel for different patient sizes | | | hip surgery scalpel/scalpel in general | | precision of incision, speed of surgery |
| poor posture, hyperlordosis, hyperkyphosis | P: hyperkyphosis, hyperlordosis | For initial treatment: hyperkyphosis of 50 degree or greater, when reaches 50% of this value for a sufficient amount of time, can move onto next brace that then reduces this value by 50% until reaches below 40 degrees. At this point, doctor decides to remove brace or leave brace on. | back/ shoulder brace | 1st value: kyphosis of 50 degrees 2nd value: kyphosis of 25 degrees | pressure, angle of kyphosis, lordosis, or posture, angle of cervical spine |
| absent eyeball, nose structure, teeth, ear structure | P: conditions listed | having any of the conditions listed in this row | cosmetic prosthesis | n/a | patient satisfaction, pressure within eye socket, adhesion of prosthesis, pressure on gums |
| palete is too small | P: reduced palete size S: misaligned teeth, gum infection | For initial treatment: Width of the palete more than 2 SD below the mean, or palete too small causing misaligned teeth. approximately monthly, the orthosis will be adjusted in order to expand the palete further or a new device will be created to shift the teeth into correct position further. | dental orthosis | initial width of palete: 3cm, next width of palete 3.5cm | improvement of alignment of teeth, expansion of palete if needed |
| missing teeth, misaligned teeth | P: missing teeth, misaligned teeth S: gum infection | missing teeth, misaligned teeth | dental implants | n/a, implants should only be re-done if a problem occurs or error was made | fit of teeth in open spaces, alignment of teeth, |

FIG. 6B2

| Example body conditions 504 | Example Primary Conditions (P) and Secondary Conditions (S) | Example Thresholds for Treatment of Primary Condition |
|---|---|---|
| foot amputation, toe amputation, leg amputation proximal, distal, or through knee joint, congenital defects resulting in absent foot, toe, or leg | | |
| arm amputation proximal, distal, or through elbow joint, or through shoulder joint, finger or hand amputation | | |
| osteoarthritis, rheumatoid arthritis, knee fracture to a certain extent, septic arthritis, ankylosing spondylitis, bone displasia, unusual bone growth, avascular necrosis, death of any part of knee joint, wearing away of meniscus, failed previous knee implants/replacements | P: conditions 504 (e.g., this row, first column in this table) S: hip problems | diagnosis of the conditions listed in this row |
| Osteoarthritis, degenerative joint disease, Rheumatoid Arthritis, Rotator Cuff Tear Arthropathy, Avascular Necrosis (Osteonecrosis), Severe Fractures, failed previous shoulder replacements/implants | | diagnosis of the conditions listed in this row |
| scoliosis, abnormal curvature of the spine, fracture of any vertebrae | P: conditions 504 (e.g., this row, first column in this table) S: various types of spinal problems, poor posture | having any of the conditions listed in this row |
| need for a scalpel for different patient sizes | | |
| poor posture, hyperlordosis, hyperkyphosis | P: hyperkyphosis, hyperlordosis | For initial treatment: hyperkyphosis of 50 degree or greater, when reaches 50% of this value for a sufficient amount of time, can move onto next brace that then reduces this value by 50% until reaches below 40 degrees. At this point, doctor decides to remove brace or leave brace on. |
| absent eyeball, nose structure, teeth, ear structure | P: conditions listed | having any of the conditions listed in this row |
| palete is too small | P: reduced palete size S: misaligned teeth, gum infection | For initial treatment: Width of the palett more than 2 SD below the mean, or palett too small causing misaligned teeth. approximately monthly, the orthosis will be adjusted in order to expand the palett further or a new device will be created to shift the teeth into correct position further. |
| missing teeth, misaligned teeth | P: missing teeth, misaligned teeth S: gum infection | missing teeth, misaligned teeth |

FIG. 6B2-1

| Example Devices 150 | Example First and Second Positions/ Parameter Values | Monitoring (e.g., via sensors 152 and / or data acquisitions via the acquisition device 102) |
|---|---|---|
| foot/leg prosthesis | | pressures, forces, moisture, skin condition within prosthesis socket, patient comfort, monitoring angles between joints so that they resemble normal gait, patient satisfaction with device |
| arm/hand prosthesis | | pressures, forces, moisture, skin condition within prosthesis socket, patient comfort and satisfaction with device |
| knee implant | n/a, these implants should only be re-done if a problem occurs or error was made | intra-joint forces, patient comfort and satisfaction, x-rays and imaging of joint to make sure in tact |
| shoulder implant | n/a, these implants should only be re-done if a problem occurs or an error was made | intra-joint forces, patient comfort and satisfaction, x-rays and imaging of joint to make sure in tact |
| spine screw | n/a only replaced with significant patient growth | changed angle of curvature of spine, screw maintaining its position |
| hip surgery scalpel/scalpel in general | | precision of incision, speed of surgery |
| back/shoulder brace | $1^{st}$ value: kyphosis of 50 degrees $2^{nd}$ value: kyphosis of 25 degrees | pressure, angle of kyphosis, lordosis, or posture, angle of cervical spine |
| cosmetic prosthesis | n/a | patient satisfaction, pressure within eye socket, adhesion of prosthesis, pressure on gums |
| dental orthosis | initial width of palete: 3cm, next width of palete 3.5cm | improvement of alignment of teeth, expansion of palete if needed |
| dental implants | n/a, implants should only be re-done if a problem occurs or error was made | fit of teeth in open spaces, alignment of teeth, |

| Example body conditions 504 | Example Primary Conditions (P) and Secondary Conditions (S) | Example Thresholds for Treatment of Primary Condition |
|---|---|---|
| patient wants to prevent pregnancy | P: conditions listed | having the want to prevent pregnancy |
| patient has a burn and needs a skin graft | P: conditions listed | diagnosis of burn needing a skin graft |
| patient cannot perform desired motions | P: conditions listed | patient cannot perform desired motions |

FIG. 6B3-2

| Example Devices 150 | Example First and Second Positions/Parameter Values | Monitoring (e.g., via sensors 152 and / or data acquisitions via the acquisition device 102) |
|---|---|---|
| intrauterine devices | n/a, implants should only be re-done if a problem occurs or an error was made | |
| tissue expanders under skin | n/a | |
| electrical stimulation (e.g., via electrodes) | optimization of electrical stimulation location | |

600B (Duplicate table below:)

| Example body conditions 504 | Example Primary Conditions (P) and Secondary Conditions (S) | Example Thresholds for Treatment of Primary Condition |
|---|---|---|
| patient wants to prevent pregnancy | P: conditions listed | having the want to prevent pregnancy |
| patient has a burn and needs a skin graft | P: conditions listed | diagnosis of burn needing a skin graft |
| patient cannot perform desired motions | P: conditions listed | patient cannot perform desired motions |

FIG. 6B3-1

| Example Devices 150 | Example First and Second Positions/Parameter Values | Monitoring (e.g., via sensors 152 and / or data acquisitions via the acquisition device 102) |
|---|---|---|
| intrauterine devices | n/a, implants should only be re-done if a problem occurs or an error was made | |
| tissue expanders under skin | n/a | |
| electrical stimulation (e.g., via electrodes) | optimization of electrical stimulation location | |

FIG. 6B3-2

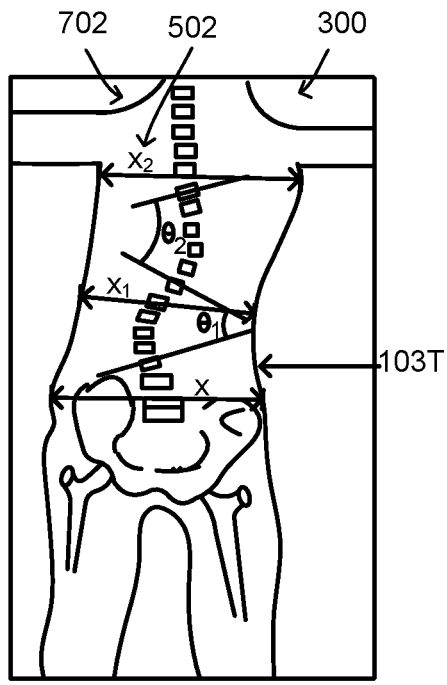
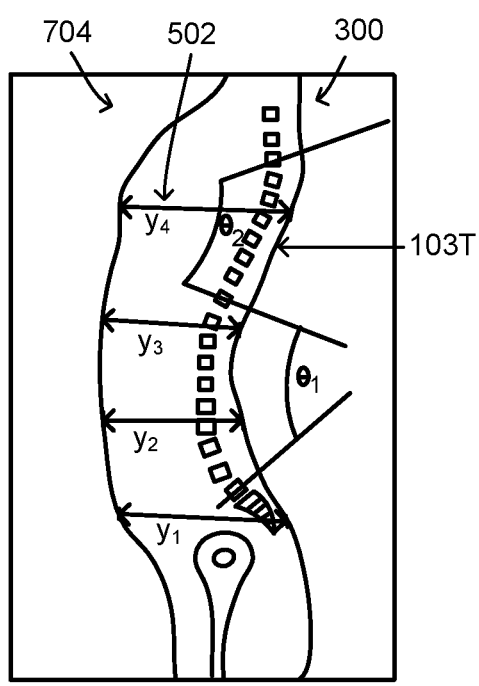
FIG. 7A    FIG. 7B
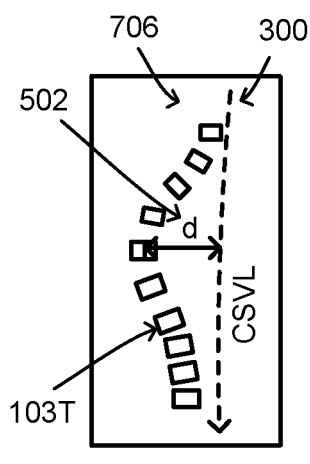
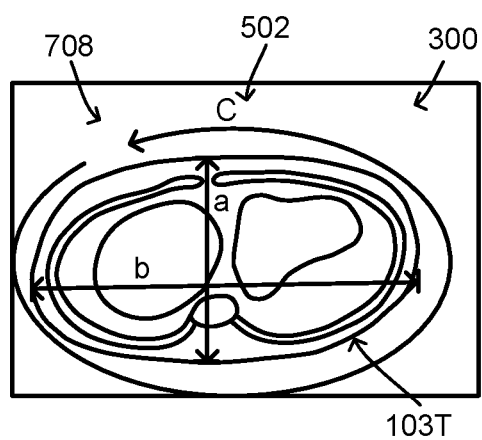
FIG. 7C    FIG. 7D

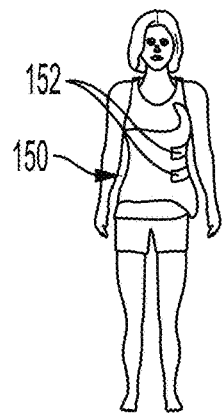
Figure 12A₁
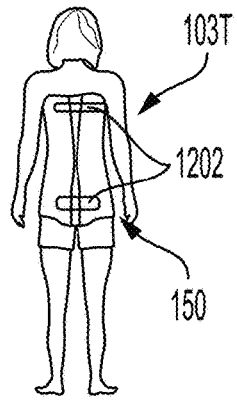
Figure 12A₂
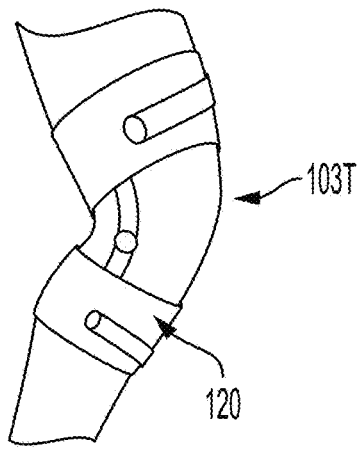
Figure 12B
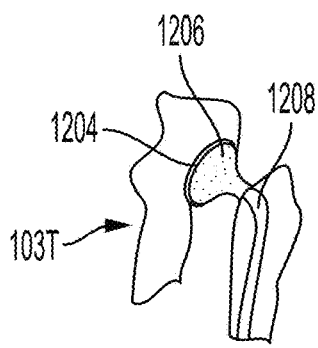
Figure 12C₁
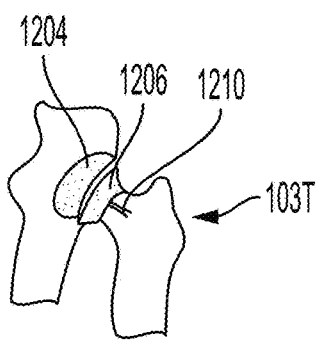
Figure 12C₂
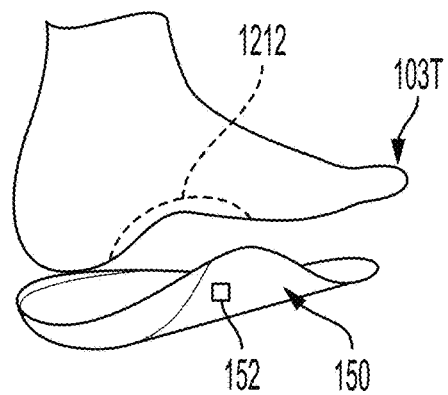
Figure 12D
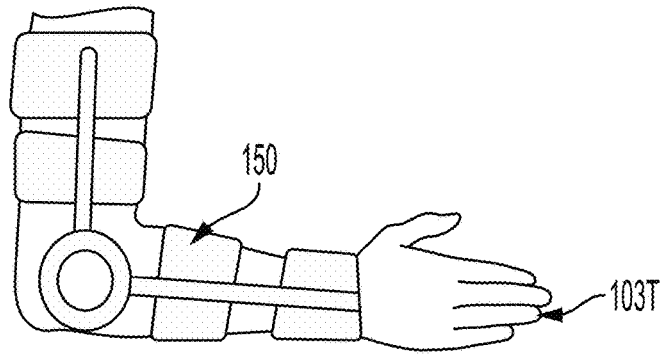
Figure 12E

BODY ENGAGERS AND METHODS OF USE

CROSS-REFERENCE TO RELATED APPLICATIONS

This application claims benefit of priority to U.S. Patent Application No. 62/752,491, filed Oct. 30, 2018, the content of which is incorporated herein by reference in its entirety.

BACKGROUND

1. Technical Field

Structures and methods for creating, using, monitoring and adapting the same are disclosed. More specifically, systems, devices and methods are disclosed for treating body conditions, monitoring body conditions and adapting treatment.

2. Background of the Art

There remains a need for improved user-specific devices to treat body conditions.

A need still exists to diagnose, via an electronic processing of images acquired from a target object, body conditions of the target object and to model and create devices to engage with (e.g., treat) the diagnosed body conditions. A need also still exists to diagnose body conditions of a target object without feedback from or consultation with a doctor (or other medical professional) via an electronic processing of images acquired from the target object and to model and create devices to engage with (e.g., treat) the diagnosed body conditions.

BRIEF SUMMARY

This disclosure relates generally to user-specific devices and methods for creating, using, monitoring and adapting the same.

More specifically, this disclosure relates to user-specific devices for treating body conditions and methods of creating, using, monitoring and adapting user-specific devices for treating body conditions.

Methods of creating body engagement devices are disclosed. For example, a method is disclosed that can include acquiring, via a data acquisition device, a digital representation of a subject. The method can include measuring, via a processor, physical parameters of the subject from the digital representation of the subject. The method can include detecting, via an analysis of the physical parameters by the processor, a body condition of the subject. The method can include determining, via the processor, fit parameters of the body condition. The method can include determining, via the processor, a treatment parameter of the body condition, where the treatment parameter is a desired change in at least one of the fit parameters from a parameter first value to a parameter second value. The method can include designing, based on the fit parameters and the treatment parameter, the body engagement device. The body engagement device, when worn or attached to the subject, can engage with the subject to change the parameter first value to the parameter second value.

Methods of creating body engagement devices are disclosed. For example, a method is disclosed that can include identifying, by processing a first digital representation of a subject via a computer, first physical parameters of the subject associated with the first digital representation and diagnosing, by processing the first physical parameters associated with the first digital representation, a first body condition of the subject. The method can include determining, via an analysis of the first physical parameters associated with the first digital representation via the computer, a first physical extent of the first body condition. The method can include designing, based on the first physical extent of the first body condition, a first digital 3D model to engage with the first body condition. The first digital 3D model, when digitally worn or digitally attached to the digital representation of the subject, can at least one of stabilize and change the first physical extent of the first body condition.

Body engagement device 3D modeling systems are disclosed. For example, a system is disclosed that can have a data acquisition device and a computer. The computer can analyze a digital representation of a subject acquired from the data acquisition device. The computer can measure, via a processor, physical parameters of the subject from the digital representation of the subject. The computer can detect, based on the analysis of the acquired digital representation of the subject, a body condition of the subject. The computer can determine fit parameters of the body condition. The computer can determine a treatment parameter of the body condition. The treatment parameter can be a desired change in at least one of the fit parameters from a parameter first value to a parameter second value. The computer can design, based on the fit parameters and the treatment parameter, the body engagement device. The body engagement device, when worn or attached to the subject, can engage with the subject to change the parameter first value to the parameter second value.

BRIEF DESCRIPTION OF THE DRAWINGS

The drawings shown and described are exemplary embodiments and non-limiting. Like reference numerals indicate identical or functionally equivalent features throughout.

FIG. $6A_1$ illustrates a table showing various data acquirable and determinable using the systems and methods described herein.

FIG. $6A_2$ is a continuation of the table shown in FIG. $6A_1$.

FIG. $6B_1$ illustrates a table showing various data acquirable and determinable using the systems and methods described herein.

FIG. $6B_2$ is a continuation of the table shown in FIG. $6B_1$.

FIG. $6B_3$ is a continuation of the table shown in FIGS. $6B_1$ and $6B_2$.

FIG. 7A illustrates an exemplary data acquisition and various exemplary physical parameters measurable on the data acquisition.

FIG. 7B illustrates an exemplary data acquisition and various exemplary physical parameters measurable on the data acquisition.

FIG. 7C illustrates an exemplary data acquisition and various exemplary physical parameters measurable on the data acquisition.

FIG. 7D illustrates an exemplary data acquisition and various exemplary physical parameters measurable on the data acquisition.

Figure 8A:
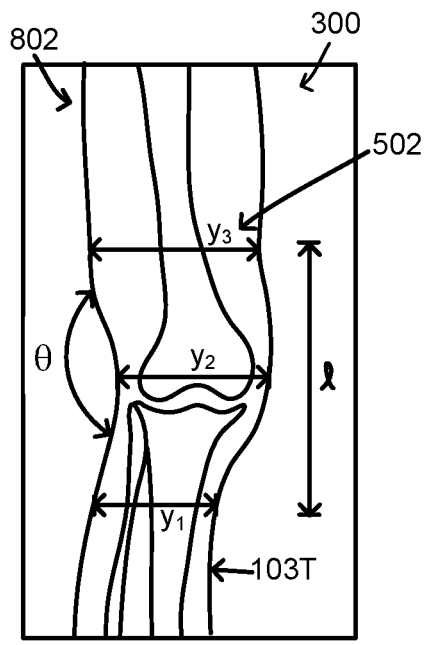

FIG. 8A illustrates an exemplary data acquisition and various exemplary physical parameters measurable on the data acquisition.

Figure 8B:
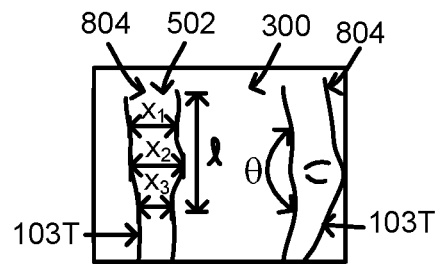

FIG. 8B illustrates an exemplary data acquisition and various exemplary physical parameters measurable on the data acquisition.

Figure 8C:
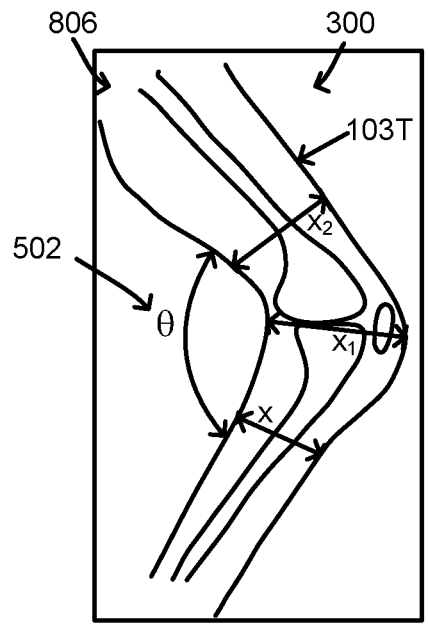

FIG. 8C illustrates an exemplary data acquisition and various exemplary physical parameters measurable on the data acquisition.

Figure 8D:
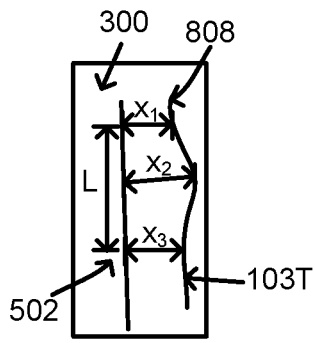

FIG. 8D illustrates an exemplary data acquisition and various exemplary physical parameters measurable on the data acquisition.

Figure 8E:
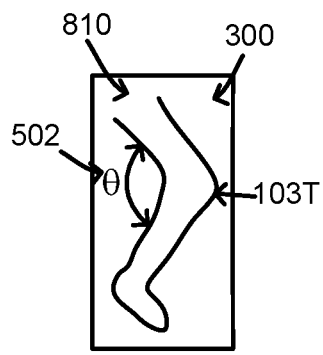

FIG. 8E illustrates an exemplary data acquisition and various exemplary physical parameters measurable on the data acquisition.

Figure 8F:
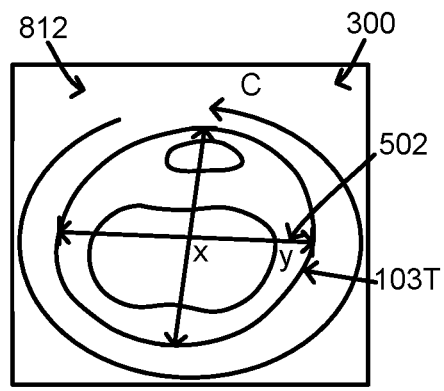

FIG. 8F illustrates an exemplary data acquisition and various exemplary physical parameters measurable on the data acquisition.

Figure 9A:
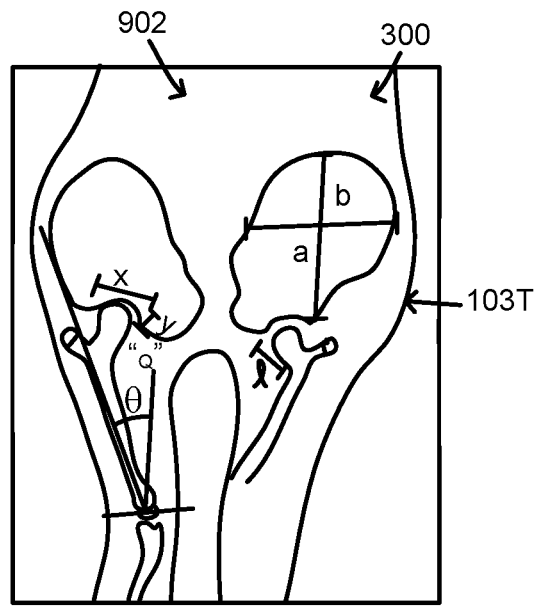

FIG. 9A illustrates an exemplary data acquisition and various exemplary physical parameters measurable on the data acquisition.

Figure 9B:
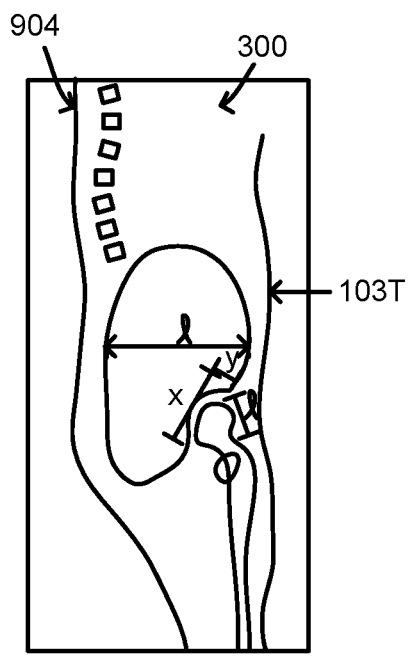

FIG. 9B illustrates an exemplary data acquisition and various exemplary physical parameters measurable on the data acquisition.

Figure 10A:
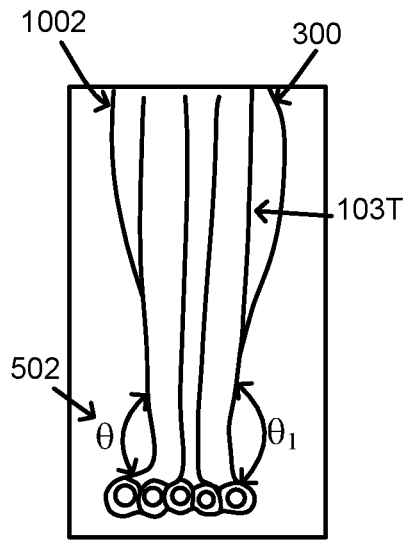

FIG. 10A illustrates an exemplary data acquisition and various exemplary physical parameters measurable on the data acquisition.

Figure 10B:
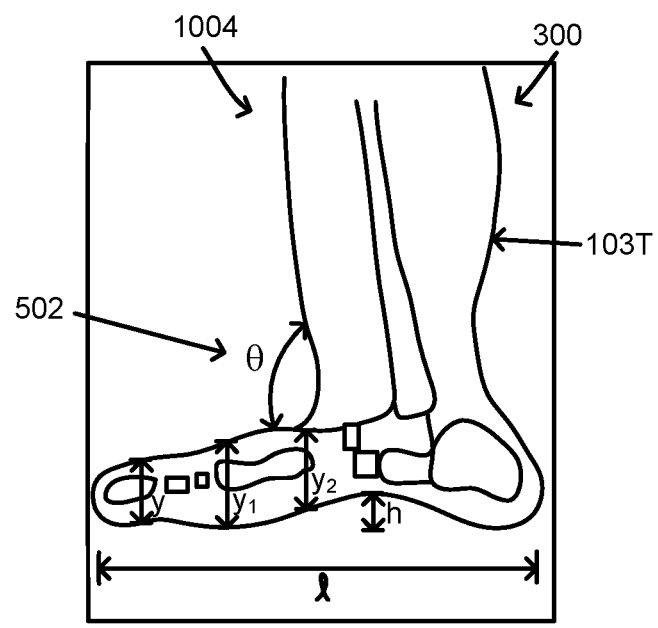

FIG. 10B illustrates an exemplary data acquisition and various exemplary physical parameters measurable on the data acquisition.

Figure 10C:
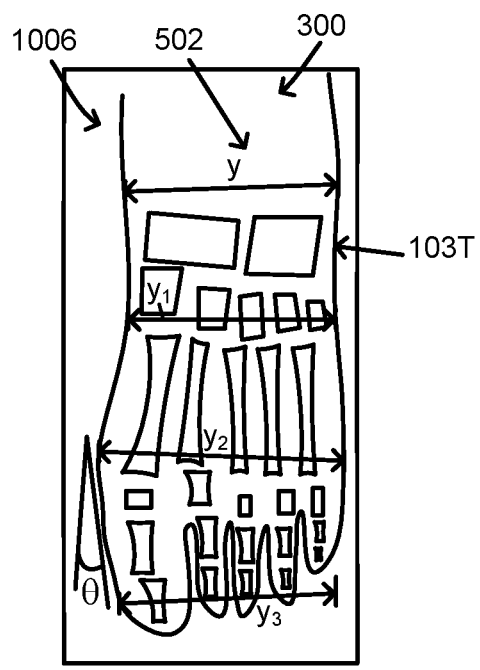

FIG. 10C illustrates an exemplary data acquisition and various exemplary physical parameters measurable on the data acquisition.

Figure 11A:
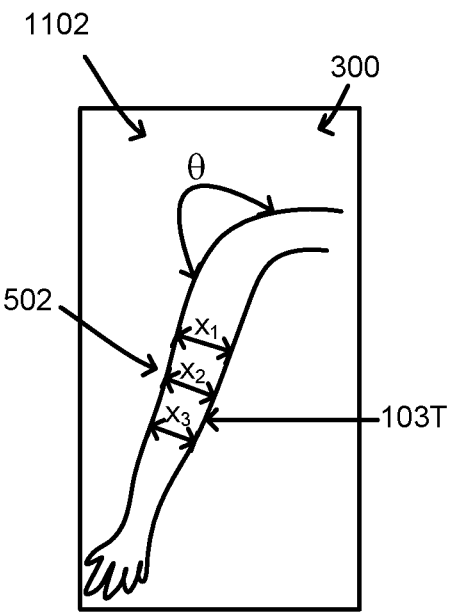

FIG. 11A illustrates an exemplary data acquisition and various exemplary physical parameters measurable on the data acquisition.

Figure 11B:
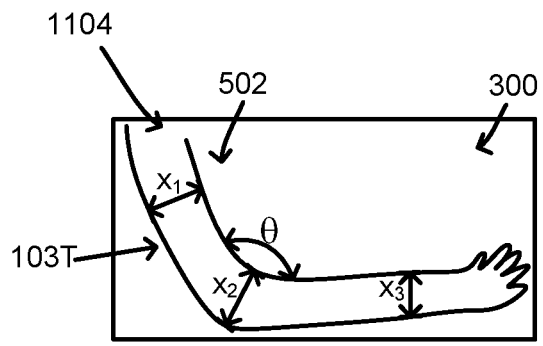

FIG. 11B illustrates an exemplary data acquisition and various exemplary physical parameters measurable on the data acquisition.

Figure 11C:
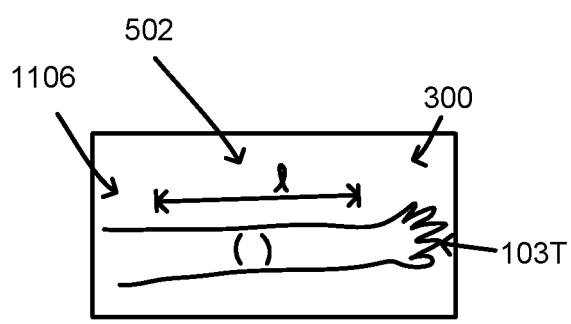

FIG. 11C illustrates an exemplary data acquisition and various exemplary physical parameters measurable on the data acquisition.

FIG. $12A_1$ illustrates a front view of a variation of a scoliosis brace created using the systems and methods described herein.

FIG. $12A_2$ illustrates a rear view of a variation of the scoliosis brace of FIG. $12A_1$.

FIG. 12B illustrates a side view of a variation of a knee brace created using the systems and methods described herein.

FIG. $12C_1$ illustrates a front view of a variation of a hip implant created using the systems and methods described herein.

FIG. $12C_2$ illustrates a front view of a variation of a hip implant created using the systems and methods described herein.

FIG. 12D illustrates a front view of a variation of an orthotic created using the systems and methods described herein.

FIG. 12E illustrates a front view of a variation of an arm brace created using the systems and methods described herein.

Figure 13A:
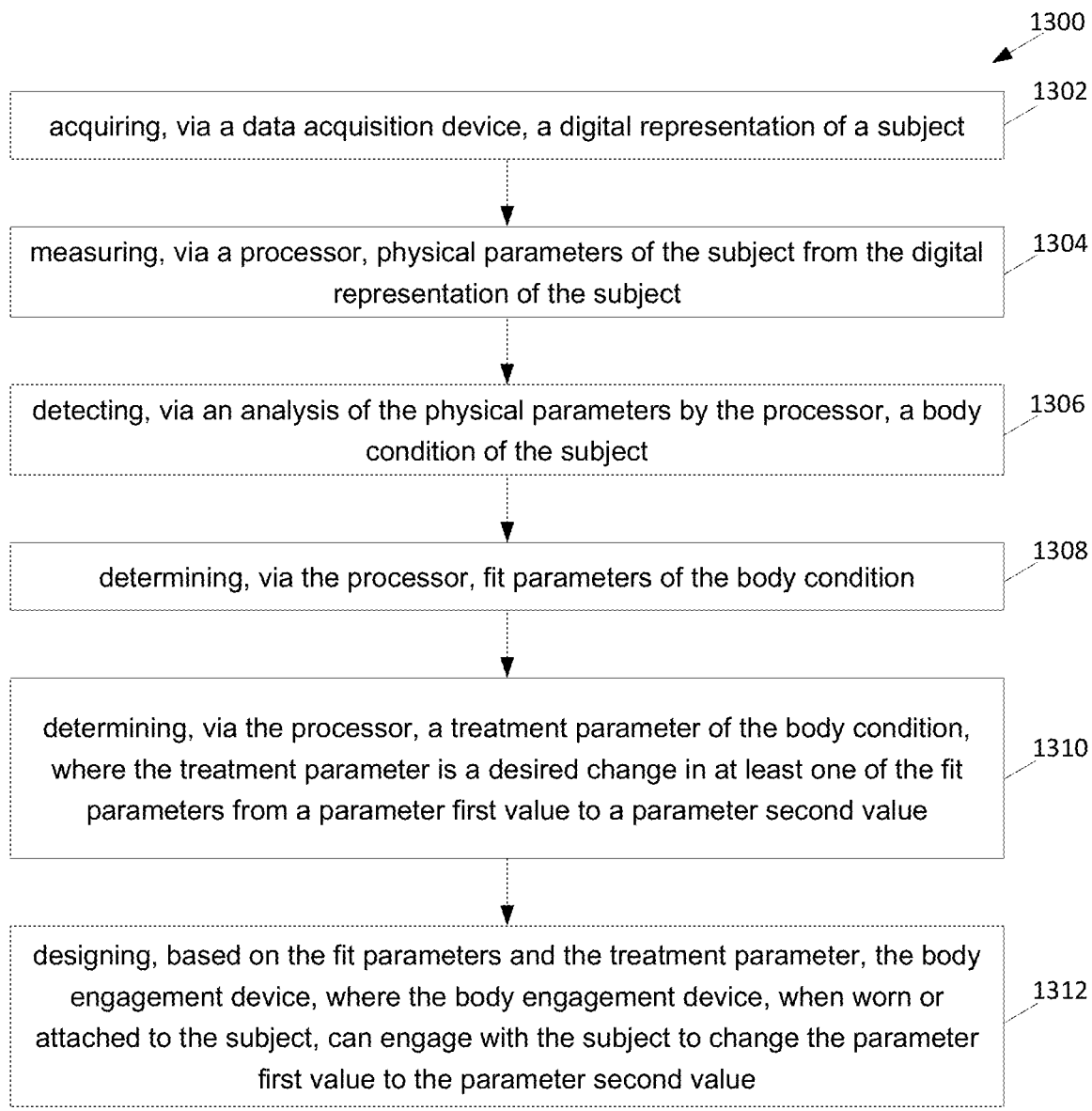

FIG. 13A illustrates a variation of a method undertaken by the system.

Figure 13B:
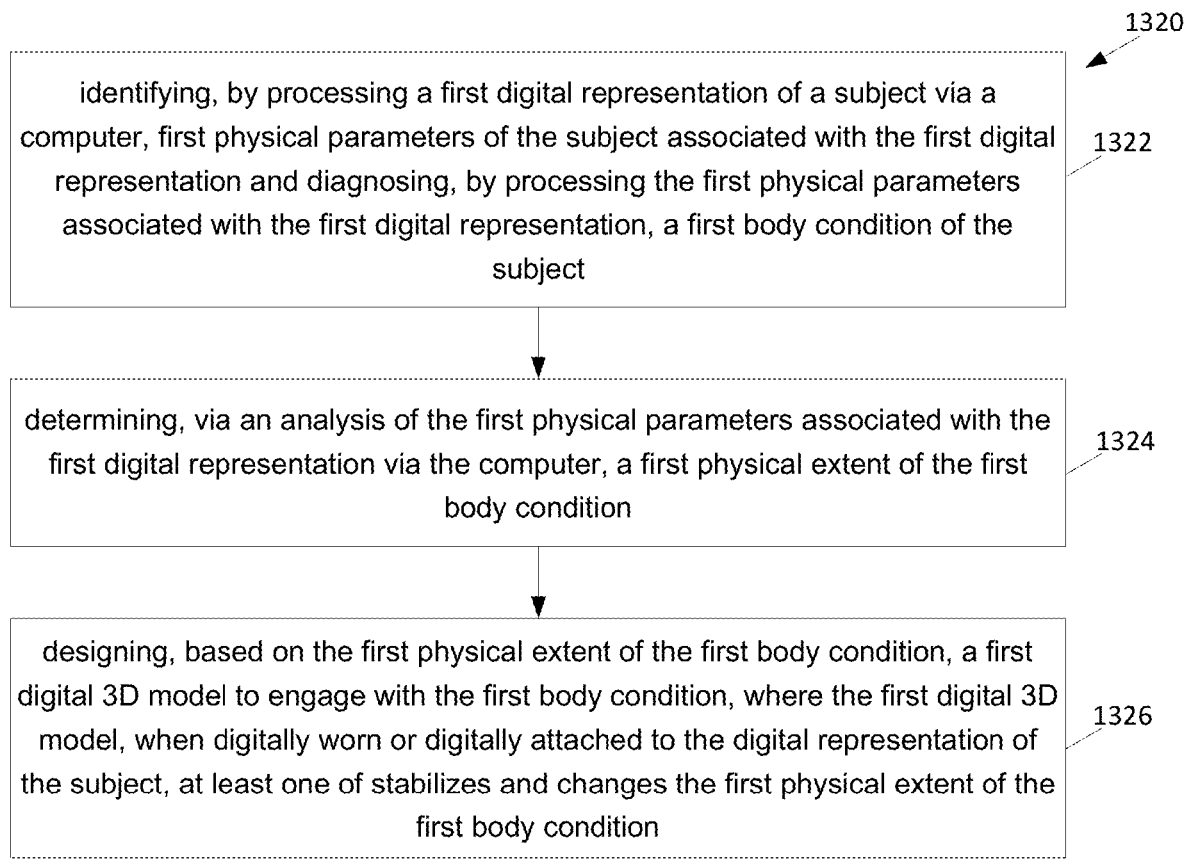

FIG. 13B illustrates a variation of a method undertaken by the system.

DETAILED DESCRIPTION

Devices and methods for creating, using, monitoring and adapting the same are disclosed. Devices and methods for monitoring users are disclosed. For example, methods for generating one or multiple devices to treat a body condition (e.g., medical condition, non-medical condition) and then adapting the devices based on the progression (including change, alteration, deviation) of the body condition are disclosed.

The devices can be body engagers. The devices can be configured to engage with the user's body. For example, when engaged with (e.g., worn by) a user, the device can be engaged with the user's body (e.g., with a limb, a joint, their torso, their neck, or any other part or parts of their body).

The devices can be engageable with one or multiple users, for example, with people, animals, or both. The user can be a patient. Each device can fit one or multiple users. For example, each device can be designed to fit multiple users. As another example, each device can be designed to fit only one user. For example, each device can be a user-specific device (also referred to as a patient-specific device) specifically designed for a single target user. For example, the device can be a user-specific device specifically designed to fit the user and no other user. A user-specific device can be unique to one user, meaning that while it may fit other users or potential users, it is designed to fit only one user (e.g., the target user) and no one else.

The device can be a user-specific device specifically designed to engage with the user to fit (e.g., conform with) the user's unique body size, body shape, and/or body dimensions. The user-specific device can be designed to conform to the user's body. The user-specific device can be adaptable to conform to the user's body as the user grows, as the user's body condition changes, as a new condition (e.g., another condition different from a previously diagnosed condition) is diagnosed, or any or all of the three. The device can be a non-user-specific device designed to fit multiple target users, for example, after an off-the-shelf adjustment is made (e.g., tighten a strap, adjust the size of a pillow, increase a heel lift, change a prescribed joint angle), so that the non-user-specific device can be customized to fit multiple target users, where each target user can have a different body size, body shape, and/or body dimensions relative to another target user. For example, where the device is a non-user-specific device, the non-user-specific device can be mass manufactured in multiple pre-determined sizes (e.g., children and adult, small, medium, and large, or any combination thereof) in order to be more patient-specific.

The devices can affect one or multiple body structures of the user, one or multiple body functions of the user, or both. For example, the devices can stabilize a body structure, change a body structure (e.g., reposition a body structure), move a body structure, stabilize a body function, change a body function, or any combination thereof. The devices can be diagnostically derived using the system and methods disclosed herein such that the devices are designed and dependent on a diagnosis of a body condition and the progression of the body condition. As another example, the devices can be diagnostically derived such that the devices are designed and dependent on a diagnosis of a first body condition and the progression of the first body condition and/or on a diagnosis of a second body condition, where the first body condition can be the primary condition and the second body condition can be the secondary condition. The second body condition can be diagnosed at the same time as or after the diagnosis of first body condition. The second body condition can be, for example, a body condition that is likely to occur based on the existence of first body condition such that the first body condition is an indicator for the second body condition. For example, if the first body condition is scoliosis, the secondary body condition can be reduced kyphosis, where scoliosis is the primary condition and reduced kyphosis is the secondary condition. The diagnosis of the first body condition can thereby function as an indicator of the current presence or likely future presence of a second body condition, where diagnosis of the first body condition can be a decision trigger to evaluate and/or monitor the user for the second body condition such that upon detection of the first body condition, the system can run a diagnostic test to evaluate for the presence or absence of the second body condition. As another example, the first body condition and/or the second body condition can function as contra-indicators of other body conditions to make the methods described herein more efficient.

For example, the devices can be configured to apply one or multiple forces to the user's body to stabilize a target body structure in a first position to thereby inhibit or prevent the target body structure from moving into a second position different from the first position. To stabilize the target body structure in the first position, the devices can be configured to (1) apply forces to the target body structure, (2) apply forces to one or multiple body structures different from the target body structure, (3) inhibit or prevent forces from being applied to the target body structure, (4) inhibit or prevent forces from being applied to one or multiple body structures different from the target body structure, or any combination of (1) to (4), for example, while the devices are engaged with the user. By stabilizing one or multiple target body structures, the devices can be configured to treat a body condition, for example, to stabilize, inhibit, or prevent further progression of a body condition that the device is designed to treat (e.g., scoliosis, bad posture, foot pronation, foot supination, hyperextension of the knee, fractures, musculoskeletal injuries). For example, the devices can be configured to apply external forces to the subject's body to adjust the curvature of the subject's spine.

As another example, the devices can be configured to apply one or multiple forces to the user's body to change (e.g., reposition) a target body structure from a first position to a second position different from the first position. To change (e.g., reposition) the target body structure from the first position to the second position, the devices can be configured to (1) apply forces to the target body structure, (2) apply forces to one or multiple body structures different from the target body structure, (3) inhibit or prevent forces from being applied to the target body structure, (4) inhibit or prevent forces from being applied to one or multiple body structures different from the target body structure, or any combination of (1) to (4), for example, while the devices are engaged with the user. By changing (e.g., repositioning) one or multiple body structures, the devices can be configured to treat one or more body conditions, for example, (1) to stabilize, inhibit, or prevent further progression of a body condition that the device is designed to treat (e.g., scoliosis, bad posture, foot pronation, foot supination, hyperextension of the knee, fractures, musculoskeletal injuries), (2) to reverse or inhibit the progression of the body condition that the device is designed to treat (e.g., scoliosis), (3) to remove or improve the body condition, or any combination of (1) to (3). For example, by moving (e.g., repositioning) one or multiple body structures, the devices can be used to temporarily or permanently improve the body condition or its symptoms. For example, the devices can stabilize or relieve back pain caused by scoliosis, or the above listed conditions.

As yet another example, the devices can be configured to apply one or multiple forces to the user's body to move a target body structure from a first position to a second position different from the first position. For example, where the device is a prosthetic (e.g., joint, hand), the prosthetic can move or facilitate movement of the user's body, move an object by the user controlling the prosthetic, or both.

The devices can be configured to affect one or multiple body structures directly, indirectly, or both. For example, to treat scoliosis, the devices can be configured to directly affect the ribs, torso, hip, and indirectly affect the spine. For example, the devices can be designed to impart forces on one or more ribs and the one or more ribs can in turn transmit the forces to the spine. The forces applied to the ribs and spine via the devices can stabilize the curvature of the user's spine or can urge the user's spine to move from a spine first shape to a spine second shape, where, for example, the spine second shape can be less curved than the spine first shape. The devices can thereby target one or multiple first body structures (e.g., the ribs) and one or multiple second body structures (e.g., the spine). For example, the devices can target the first body structures (e.g., the ribs) to affect the second body structures (e.g., the spine) such that by targeting the first body structures (e.g., the ribs), the first and second body structures can be simultaneously targeted by a single device. For example, the first body structures can be moved by the device and the second body structures can be moved by the first body structures. The devices can accommodate or restrict the movement of any joint of the body, along any of its degrees of freedom.

The devices can create any range of forces which affect one or multiple body structures. For example, the devices can be the source of the forces applied to the body (e.g., to the first and second body structures in the scoliosis example), where the distinction between the first and second body structures is illustrative of the exemplary force pathways that the devices can create. For example, the devices can be configured to affect a first body structure (e.g., a brace to correct a broken forearm), where the first body structure can be the only body structure affected by the device. As another example, the devices can create force pathways which affect multiple body structures, for example, 2 to 50 or less body structures, 100 or less body structures, 100 or more body structures, including every 1 body structure increment within these ranges. For example, the devices can affect a first body structure (e.g., a rib) and a second body structure (e.g., a vertebra). The force pathway can be distributed simultaneously, serially, or both. For example, where there are three structures, the forces from the device can be simultaneously distributed to the first, second and third structures. As another example, where there are three structures, the forces can be serially (also referred to as sequentially) distributed to the first structure, then to the second structure, and then to the third structure. The forces can be parallel to one another, perpendicular to one another, and/or at any degree increment from one another in any direction, for example, from 0 degrees to 360 degrees, including every 1 degree increment within this range.

The devices can apply one or multiple forces to the user's body to promote the user's body to deposit tissue (e.g., bone) in a target area or to send hormones (e.g., human growth hormones) to a target area. The devices can help one or multiple muscles to move, one or multiple biomechanical systems to move, one or multiple bones to move, and/or one or multiple body structures to move, or any combination thereof.

In these various exemplary ways, the devices can, for example, apply forces, relieve forces, stabilize forces and/or change the force distributions external and/or internal to the user's body, thereby stabilizing the user's body, restructuring the user's body, or both. As another example, the devices can, for example, apply pressure, relieve pressure, stabilize pressure and/or change the pressure distributions external and/or internal to the user's body, thereby stabilizing the user's body, restructuring the user's body, or both. The devices can restructure the user's body, for example, by moving one or multiple body first body structures relative to one or multiple second body structures such as from a first position to one or multiple subsequent positions different from the first position (e.g., to a second position different from the first position, to a third position different from the first and second positions, and so on, for example, to 10 or less subsequent positions, 100 or less subsequent positions, 1000 or less subsequent positions). As another example, the devices can restructure the user's body by affecting tissue growth, by means of tissue expanders or body braces emitting low-grade electromagnetic fields to promote bone growth, or hormone production or reduction or neither or both in the target area, in one or more non-target areas, or both.

The devices can be configured to affect the user's body movement. For example, the devices can impart forces on the body which restrict movement, which guide movement, which induce movement or any combination of the three. Where movement is restricted, for example, the devices can inhibit or prevent the user from moving a body part from a first position to a second position, or from moving in any form. Movement induction can be via electrodes placed on top of the skin or in the muscle that will create the desired movement when electrically stimulated. Where movement is guided or induced, for example, the devices can passively allow or actively encourage movement of a body part from a first position to a second position, for example, when the user moves the body part (e.g., from an arm from a first position to a second position). An example of movement induction is if a patient has the condition called foot drop, usually caused by stroke, an electrode can be placed on the patient's skin over the tibialis anterior muscle in order to cause the foot to lift and clear the ground during gait. Additionally or alternatively, the devices can be configured to not affect the user's body movement. For example, the devices can impart forces on the body which do not restrict movement, which do not guide movement, or both.

The devices can affect the user's physical health, mental health, or both. For example, the devices can stabilize or improve the user's mobility, stabilize or improve the user's comfort, stabilize or decrease the user's discomfort, or any combination thereof, where the mobility, comfort, and/or discomfort can be associated with the body condition (e.g., scoliosis) that the device is treating.

The devices can be conformable, non-conformable, or both. The devices can have a conformable shape, a non-conformable shape, or both. The devices can be conformable to the user's body. For example, the devices can be conformable to one or multiple body structures, non-conformable to one or multiple body structures, both. For example, for conformable devices, the devices can have a shape that matches or closely approximates the external surface geometry of the user's body structures, a shape that matches or closely approximates the internal geometry of the user's body structures (e.g., bone, organ cavities), or both. The devices can be rigid, semi-rigid, flexible, or any combination thereof. The flexible devices can morph (e.g., via their flexibility and/or elasticity) to fit the shape of the external or internal body structure. The devices can be made of polymers, metals, or both. The devices can be made of shape memory alloys (e.g., Nitinol). The devices can be made of elastic material, inelastic material, both. The devices can be bioabsorbable (e.g. resorbable surgical screws), non-bioabsorbable, or both. The devices can be manufactured with any method. For example, the devices can be 3D printed, whereby the devices can be 3D printed tissue that can be accepted by the user's immune system.

The devices can be applied to the user, for example, via the user, a person different from the user, or both.

The devices can be wearable devices, implantable devices, or both. For example, the devices can be removably attachable to the user, permanently attachable to the user, removably implantable in the user, permanently implantable in the user, or any combination thereof. The devices can be laid on top of the body, applied to the outside of the body, attached to skin, implanted in the body, or both. The devices can be designed to penetrate the skin (e.g., a person's skin, an animal's fur), not to penetrate the skin, or both. The devices can be worn under clothing, over clothing, or both. The devices can be attached to clothing (e.g., shirt, pants, skirt, dress, sweater, underwear, collar, sportswear, swimsuit, jacket), integrated with clothing, or both. The devices can be attached to or integrated with objects different from the user and their clothing, for example, bags (e.g., backpacks, purses), seats (e.g., car seats), chairs, beds, blankets, bicycles, shoes, socks, skis, sports equipment, or any combination thereof. The devices can be worn during the day, worn during the night, or both.

The devices can be custom made specific for the user, for example, based on a medical diagnosis using the systems (e.g., system 100) and methods (e.g., method 200) disclosed herein, data associated with the medical diagnosis, data unassociated with the medical diagnosis, or any combination thereof. The data can include data relating to the user's body and body condition, for example, (1) the anatomic indicators of the body condition, (2) the shape, size, topography, and dimensions of the body and body condition, (3) the shape, size and dimensions of one or multiple target body structures, (4) the shape, size and dimensions of one or multiple non-target body structures, (5) monitoring data (e.g., the progression or growth of any of (1)-(4), sensor data associated or unassociated with (1)-(4), user wear data, the progression of any of the disclosed, contemplated and/or illustrated monitored data), (6) user input (e.g., their comfort and/or discomfort with the device), (7) any of (1)-(7) acquired from or determined for another user or users, or any combination of (1)-(7). The data (1)-(7) is also individually and collectively referred to more simply as "data" or synonyms thereof, for example, "acquired data". The data (e.g., any combination of data (1)-(7)) can include images, image data, medical image data, sensor data, or any combination thereof, for example, acquired from one or multiple data acquisition devices which can include, for example, one or multiple image acquisition devices, one or multiple sensors, handmade manual measurements (e.g., using a ruler), or any combination thereof.

The devices can be adaptable. For example, the devices can be adjustable, modifiable, reconfigurable, or any combination thereof. The devices can be designed based on any combination of data (1)-(7), independent of any combination of data (1)-(7), or any combination thereof. The devices can be manually or automatically adjusted, modified, reconfigured, or any combination thereof, for example, based on any combination of data (1)-(7). The devices can be modular.

The devices can have a device first configuration and one or multiple subsequent device configurations (e.g., a device second configuration different from the device first configuration, a device third configuration different from the device first and/or second configurations, and so on, for example, to 10 or less subsequent device configurations, 100 or less subsequent device configurations, 1000 or less subsequent device configurations, including every 1 device configuration increment within these ranges). The device first configuration can be the initial configuration of the device or any subsequent device configuration, where the subsequent configuration can be a configuration adapted from a previous configuration (e.g., the device initial configuration or a device subsequent configuration). The device initial configuration can be the device configuration when the device is initially made. The device initial configuration may or may not be adapted (e.g., adjusted, modified, reconfigured) before the subject wears the device for the first time or before the device is implanted into the subject for the first time. The devices can be adjusted, modified, reconfigured, or any combination thereof into one or multiple subsequent device configurations, for example, from a device first configuration into a device second configuration different from the device first configuration. The first and second configuration may also be the same configuration, with transition configurations between them. A single device can thereby function as a series of devices that are each adjustable, modifiable, reconfigurable, or any combination thereof to affect one or multiple body structures of the user, one or multiple body functions of the user, or both. As another example, a device can thereby be changed into a series of devices that are each adjustable, modifiable, reconfigurable, or any combination thereof to affect one or multiple body structures of the user, one or multiple body functions of the user, or both.

A single device can be part of or not part of a series of multiple devices. For example, each device can be a standalone device that is not part of an intended or unintended series of multiple devices. Each device can be a standalone device that is not part of a predetermined series of devices. In such variations, a single device can be adjusted, modified, or reconfigured into a series of device configurations (e.g., from an initial configuration to any number of subsequent configurations, where each configuration of the device can be an iteration of the device in a series of device configurations) that can achieve the same effects as a series of multiple devices or as a predetermined series of multiple devices. In such variations, each device can be adjusted, modified, or reconfigured into a series of device configurations that can achieve the same effects as a series of multiple devices or as a predetermined series of multiple devices. For example, where the devices are orthodontic trays, a single orthodontic tray can be adjusted, modified and/or reconfigured such that a predetermined series of separate orthodontic trays can be replaced with less trays using the devices than the number of orthodontic trays normally required in the predetermined series without using the device (e.g., the $1^{st}$, $2^{nd}$ and $3^{rd}$ trays in a predetermined series of orthodontic trays can be replaced with a single device created and adapted using the methods disclosed herein), where each device (e.g., i.e., orthodontic tray in this example) can function as a series of multiple different orthodontic trays. Another example is as the patient gets used to pressure on the spine, a single scoliosis brace can be adapted (e.g., tightened) via a locking mechanism without having to order another brace. As another example, the devices can be part of a series of devices. For example, the devices can be devices that are part of an intended or unintended series of devices, including, for example, a predetermined series of devices. A device series can have, for example, 2 to 10 or less devices, 2 to 50 or less devices, 2 to 100 or less devices, including every 1 device increment within these ranges (e.g., 5 devices, 10 devices, 15 devices, 50 devices, 100 devices). Each device in the series (e.g., a non-predetermined and/or a predetermined series) can be adjustable, modifiable, reconfigurable, or any combination thereof. As another example, some or all of the devices in a series of multiple devices can be non-adjustable, non-modifiable, non-reconfigurable, or any combination thereof.

The devices can be designed and applied to the user over time to stabilize the target body structure, change the target body structure (e.g., reposition the target body structure), move the target body structure, or any combination thereof. The devices can affect one or multiple body structures of the user, one or multiple body functions of the user, or both. For example, the devices can stabilize a body structure, change a body structure (e.g., reposition a body structure), move a body structure, stabilize a body function, change a body function, or any combination thereof.

For example, where the device is an orthodontic tray, the device can be designed and applied to the user over time in order to move (e.g., reposition) individual teeth in successive steps. The device can be configured to be adapted in increments, for example, in increments of less than 2 mm, less than 1 mm, or less than 0.5 mm. The device can thereby be configured to move individual teeth in successive increments, where the successive use of the device in each of its configurations permits the device to progressively move individual teeth in small increments of about less than 2 mm, less than 1 mm, or less than 0.5 mm. The increments can refer to the maximum linear or non-linear translation of any point on a tooth as a result of using the device in one of its configurations. The interior surfaces of successive devices can be adjusted, modified, or reconfigured so that the device can function as a series of devices such that the interior surfaces of successive device configurations can differ in their tooth-conforming configuration by less than 2 mm, less than 1 mm, less than 0.5 mm, or less than 0.2 mm, respectively.

The devices can be medical devices, therapeutic devices, treatment devices, monitoring devices, preventative devices, or any combination thereof, and/or devices that enhance these devices (e.g., for a prosthetic there can be a robotic arm, and the device can be a device that helps the robotic arm function based on the fit and the forces sensed from the muscles to move the robotic arm which moves an object, an attachment to a prosthetic arm that helps the user complete tasks, or devices added to braces to make the brace more comfortable to the user).

As mentioned above, methods for creating, using, monitoring and adapting devices for the body are disclosed, as are methods for diagnosing body conditions, treating body conditions, monitoring body conditions, and adapting the treatment of body conditions. The methods can include, for example, creating, using, and/or monitoring devices to affect one or multiple body conditions of a user. The methods can include designing and generating one or multiple devices to cure, mitigate, treat, prevent, or any combination thereof, one or multiple body conditions. The medical devices can be configured to affect one or multiple body structures and/or functions of a user's body. The body conditions can include, for example, diseases, disorders, deformities, injuries, deficiencies, or any combination thereof. The body conditions can be internal conditions, external conditions, or both. The methods can include diagnosing the body conditions, monitoring the body conditions, or both.

For example, the methods can include diagnosing a body condition and designing, creating, and adapting a device based on the diagnosis, the extent of the body condition, the progression of the body condition, the monitoring data (e.g., wear data), measurements, or any combination thereof. The monitoring data can be internal user data, external user data, surface data of the user, surrounding data (e.g., environmental data), and at a distance data (e.g., data in location different from the user).

As another example, the methods can include diagnosing a body condition, identifying the fit parameters and treatment parameters of the body condition, creating a 3D model based on the identified fit and treatment parameters, and constructing the device, or any combination thereof, where the fit parameters can be external and/or internal characteristics and the treatment parameters can be a desired change in an internal and/or external parameter of the subject, e.g., a delta of a relative position between a first portion of the subject's body and a second portion of the subject's body).

User-specific devices (e.g., medical devices) and adaptive systems for creating, adapting, monitoring and/or using the same are thereby disclosed.

Figure 1A:
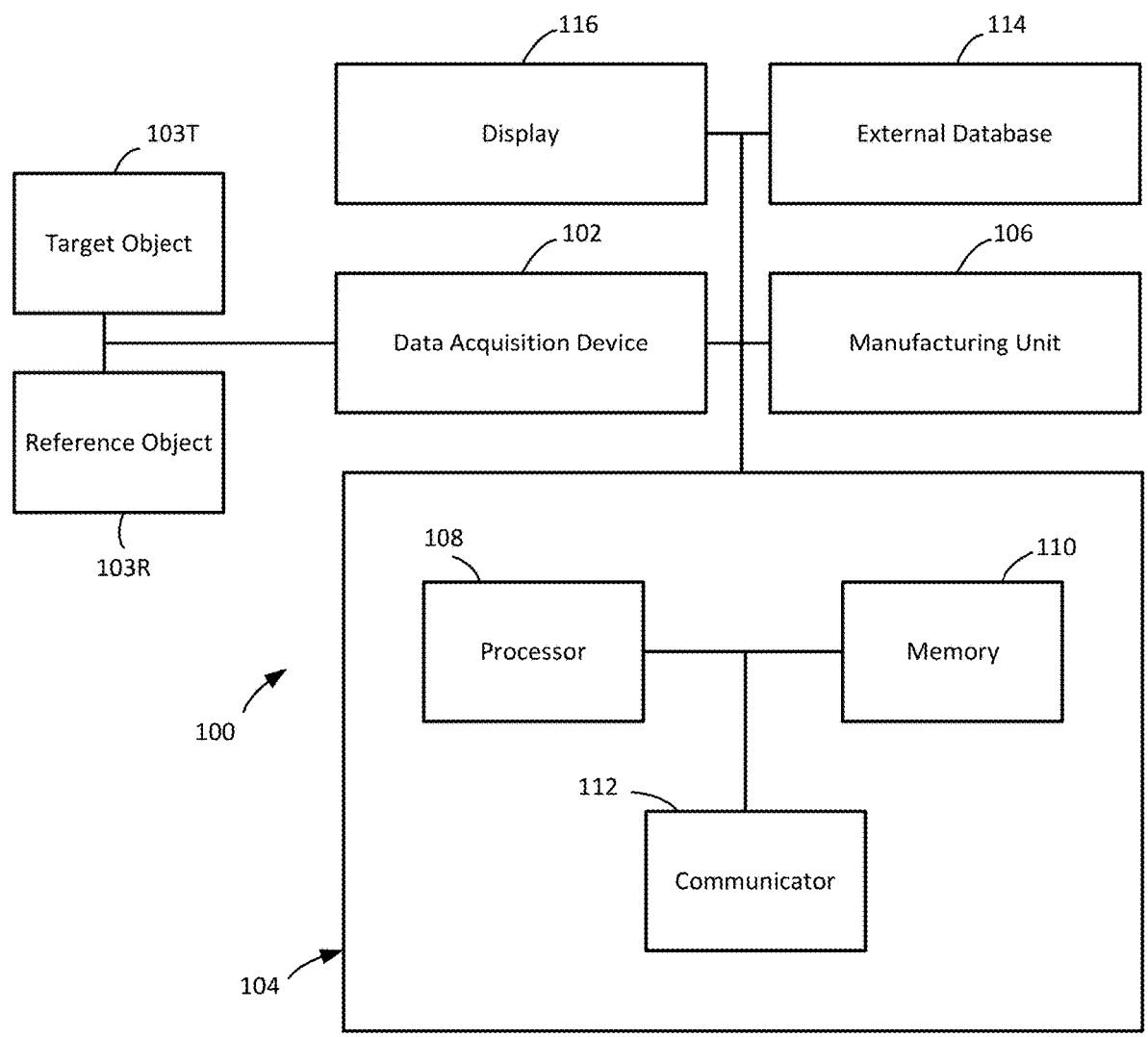
FIG. 1A illustrates a variation of a schematic of a 3D modeling system.

FIG. 1A illustrates a schematic of a variation of a 3D modeling system 100. The 3D modeling system 100 can model the devices disclosed, contemplated, and/or illustrated herein (also referred to as the structure 150 and the device 150). The system 100 can include a data acquisition device 102, a modeling unit 104, a manufacturing unit 106, or any combination thereof. The data acquisition device 102 can be in wired or wireless communication with the modeling unit 104. The modeling unit 104 can be in wired or wireless communication with the manufacturing unit 106. The modeling unit 104 can receive data from one or more data acquisition devices 102. The data acquisition devices 102 can be used to capture (also referred to as image, digitally image, or any combination thereof) reference and target objects 103R, 103T. The data acquisition devices 102 can be, for example, sensors, imaging devices, computing devices, digital hand drawings, or any other image capturing device. The imaging devices can be, for example, scanners, 3D scanners, cameras, x-ray devices, MRI systems, ultrasound systems, ultrasonographic systems, CT systems, nuclear medicine imaging, including PET scans, mammography, DEXA scans, colonoscope, and endoscope, or any combination thereof.

The same or different data acquisition device 102 can be used to image each of the reference and/or target objects 103R, 103T. The data acquisition device 102 can be used to create an image or digital image of the entire body and/or one or more parts of the body, for example, the entire body, limbs or portions thereof, joints, the torso, bone, muscles, blood vessels, soft tissue, non-soft tissue, organs, teeth, or any combination thereof. The target objects 103T can be topologically isomorphic to a reference object 103R. The target objects 103T can also be non-topologically isomorphic to a reference object 103R.

The modeling unit 104 can process data received and/or retrieved from the data acquisition device 102. The modeling unit 104 can be local or remote relative to the data acquisition device 102. For example, the modeling unit 104 can be on or be part of a server such as a cloud server, a cluster server, and/or a storage server. The modeling unit 104 can have a processor unit configured to process the images received from the data acquisition devices 102.

The manufacturing unit 106 can process (e.g., via a processor) data received and/or retrieved from the modeling unit 104. The manufacturing unit 106 can be local or remote relative to the modeling unit 104. The manufacturing unit 106 can be connected to the modeling unit 104 through a network. The manufacturing unit 106 can manufacture structures using the 2D or 3D models disclosed. The manufacturing unit 106 can manufacture the 3D reference models disclosed, the 3D target models disclosed, or any combination.

The manufacturing unit 106 can manufacture the disclosed models, for example, using 3D printing, computer numerical control (CNC) routers, industrial robots, textile machines, or any combination thereof. The 3D printing techniques used can include, for example, stereolithography (SLA), digital light processing (DLP), fused deposition modeling (FDM), selective laser sintering (SLS), selective laser melting (SLM), electronic beam melting (EBM), laminated object manufacturing (LOM), 3D model based manufacturing processes, or any combination thereof. The CNC routers used can include, for example, plasma cutters, milling machines, lathes, laser cutters, mill-turn multiaxis machines, surface grinders, tool & cutter grinders (e.g. Walter, Anka), multi-axis machines, specialty machines, or any combination thereof. The industrial robots used can include, for example, cartesian coordinate robots (also called linear robots), SCARA robots (selective compliance assembly robot arm and selective compliance articulated robot arm), 6-axis robots, redundant robots, dual-arm robots, welding robots, or any combination thereof. The textile machines used can include, for example, weaving machines, knitting machines, garment machines, cutting machines, sewing machines, or any combination thereof. In addition to or in lieu of the manufacturing unit 106, the devices 150 can be manufactured by hand (e.g., hand sewn or otherwise handmade).

FIG. 1A further illustrates that the modeling unit 104 can have one or multiple processing units 108, memory units 110, communication units 112, or any combination thereof.

The processing unit 108 can be coupled to the memory and communication units 110, 112 through, for example, high-speed buses.

The processing units 108 can include one or more central processing units (CPUs), graphical processing units (GPUs), application-specific integrated circuits (ASICs), field-programmable gate arrays (FPGAs), neural processing units, or any combination thereof. The processing units 108 can be programmable processors. The processing units 108 can execute software stored in the memory units 110 to execute the methods, instructions, and/or algorithms described herein. The processing units 108 can be an embedded processor, a processor core, a microprocessor, a logic circuit, a hardware finite state machine (FSM), a digital signal processor (DSP), or any combination thereof. As a more specific example, the processing units 108 can be a 32-bit or a 64-bit processor. The processing units 108 can be a quantum computer processor or processors.

The memory units 110 can store software, data, logs, or any combination thereof. The memory units 110 can store data received from the data acquisition devices 102, as well as the output from the processing units 108. The memory units 110 can be internal memory of the modeling unit 104 as shown in FIG. 1A, or can be external memory, such as a memory residing on a storage node, external drive, a cloud server, and/or a storage server. The memory units 110 can be a volatile memory or a non-volatile memory. For example, the memory units 110 can be a non-volatile storage medium such as non-volatile random access memory (NVRAM), flash memory, disk storage, or a volatile storage such as static random access memory (SRAM). The memory units 110 can be the main storage unit for the modeling unit 104.

The communication unit 112 can be a transceiver. The communication unit 112 can include one or more wired or wireless communication interfaces. The communication unit 112 can be a network interface card of the modeling unit 104. The communication unit 112 can be a wireless modem or a wired modem, for example, a WiFi modem, a 3G modem, a 4G modem, an LTE modem, a satellite modem, a 5G modem. Additionally or alternatively, the communication unit 112 can be a Bluetooth™ component, a radio receiver, an antenna, or any combination thereof. For example, the communication unit 112 can be a server communication unit. The modeling unit 104 can transmit and/or receive data packets and/or messages using the communication unit 112. The communication unit 112 can connect to or communicatively couple with one or more wireless signal transceivers and/or networks.

FIG. 1A further illustrates that the system 100 can have one or more external databases 114 (also referred to as datastores). The external data bases 114 can be configured to store data associated with the reference and/or target objects 103R, 103T. The external databases 114 can be separate from, alternative to, and/or additional to the memory units 110. Additionally or alternatively, the external database 114 can be integrated or otherwise combined with the memory units 110. The external databases and datastores 114 can be on or be part of a server, for example, a cloud server, and/or a storage server.

The memory 110 and/or the external database 114 can be configured to store data associated with reference objects 103R and/or with target objects 103T. The target object data can correspond to patient-specific data (also referred to as user-specific data). The reference object data can correspond to patient-specific data. The reference object data can correspond to non-patient specific data (also referred to as non-user specific data). For example, the reference object 103R can correspond to an image of a first person and the target object 103T can correspond to an image of a second person different from the first person. The data associated with the target object can also be used as reference object data, for example, to modify a geometric design definition and/or to create a new geometric design definition, both of which can be but need not be defined by the reference object.

FIG. 1A further illustrates that the system 100 can have one or more displays 116 (also referred to as projections). For example, the display 116 can be a projection onto any surface such as a wall. As another example, the display can be a projection on a screen (e.g., computer screen, smartphone screen). The displays 116 can display data acquisition results, modeling results, or any combination thereof. The displays 116 can be integrated with the device or system having the modeling unit 104 and/or can be part of a standalone device in wired or wireless communication with the modeling unit 104. For example, the display 116 can be part of (e.g. embedded in) a computer, a smartphone, a tablet, a laptop, a smartwatch, or any combination thereof. The device having the display 116 can be in communication with the data acquisition devices 102, external database 114, manufacturing unit 106, one or more other devices, the cloud, and/or one or more networks.

Executable code can be installed on memory (e.g., memory 110) of the device having the display 116. When the executable code is executed by the system 100, the system 100 can perform the instructions, processes, methods, and operations disclosed and contemplated herein, such that the system 100 can analyze data acquisition results and perform the methods disclosed herein, for example, determining geometric design definitions, generating 3D models, adjusting 3D models, improving 3D models, or any combination thereof. For example, executable code can be downloaded onto a computer configured to carry out the various functions of the modeling unit 104. Additionally or alternatively, executable code can be located on the cloud, for example, on a server, on neural networks, machine learning data trained models, or any combination thereof. A device (e.g., a smartphone) can query the server to run the executable code on the server to carry out the instructions, processes, methods, and operations disclosed and contemplated herein.

Additionally or alternatively, the modeling unit 104 can comprise downloadable executable code that utilizes existing processing, memory, and data storage features of a device and/or the cloud.

Figure 1B:
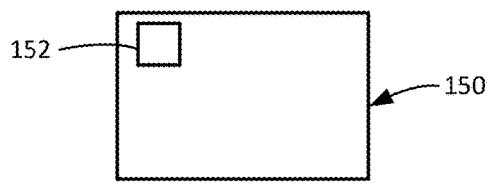
FIG. 1B illustrates a variation of a schematic of a manufactured 3D model.

FIG. 1B illustrates a variation of a structure 150 (also referred to as the device 150 and a manufactured 3D model) that can be created with the system 100. For example, the structure 150 can be any of the devices disclosed herein, including any of the devices mentioned above and below and shown in the figures. FIG. 1B illustrates that a manufactured 3D model 150 can have one or multiple sensors 152, for example, 1 to 25 sensors 152, 1 to 50 sensors 152, or 1 to 100 sensors 152, including every 1 sensor increment within these ranges. The sensors 152 can be attached to and/or integrated with the structure 150. The sensors 152 can be removably attached to the structure 150. The sensors 152 can be flexible or rigid. The sensors 152 can be attached to one or multiple flexible circuits (e.g., flexible PCB) that can be attached and/or integrated with and/or manufactured with the structure 150, for example, 1 to 100 flexible circuits. The sensors 152 can comprise a sensor array. The sensor array can be rigid or flexible. The sensors 152 can be on an inner surface, on an outer surface, in an interior, and/or along one or more edges of the structure 150, which can be either external or internal to the body. Data from the sensors 152 and/or sensor arrays can be communicated wired or wirelessly, for example, to one or more controllers, networks, servers, modeling units 104, data acquisition devices 102, or any combination thereof.

The sensors 152 can include, for example, one or more accelerometers, breathing monitors, heart rate monitors, blood pressure sensors, moisture sensors, temperature sensors, pressure sensors, displacement sensors, force sensors, environmental sensors, gyroscope sensors, shock sensors, torque sensors, strain gauge sensors, or any combination thereof. The sensors 152 can be usage sensors configured to acquire data when the manufactured 3D models are being used (e.g., when worn, when carried, when implanted). Additionally or alternatively, the sensors 152 can be sensors configured to acquire data when the manufactured 3D models are not being used. Data from the sensors 152 can be used to improve the geometric design definition and help improve the design of the structure 150 (e.g., by changing the fit parameters of the structure 150 with the user), for example, to improve the structure's function (e.g., to periodically change the force pathways exerted against a user's ribs via the structure 150 to reduce or stabilize the curvature of their spine so that their scoliosis can be treated with the structure 150) and/or to increase a user's comfort when using the structure.

The one or more accelerometers 152 can monitor movement of the user (not shown) and/or structure 150. The accelerometers can be configured to check or monitor the user's mobility (e.g., range of motion, changes in position, changes in movement) and capture kinematic data while using the structure. Accelerometer data can be used to improve the geometric design definition so that the mobility associated with subsequent structures can be improved (e.g., so that a user's range of motion is increased, so that user movement is easier, so that the structure provides less resistance to user movement) and help improve the design of the structure 150 (e.g., by adjusting, based on the accelerometer data analyzed, one or multiple physical parameters of the structure 150, by adjusting, based on the accelerometer data analyzed, one or multiple stimulation parameters of any stimulator (e.g., sensor) configured to deliver a stimulant (e.g., electrical stimulant, chemical stimulant) to the user, or by adjusting both). For example, where a stimulator is configured to deliver an electrical impulse to the user (e.g., to one of their muscles), the voltage associated with the electrical impulse can be adjusted based on the accelerometer data analyzed. For example, if the pressure within a scoliosis brace is measured to be too high (e.g., 11 kPa) based on a physician's recommendations, the design can be improved to provide less pressure to the torso.

The sensors 152 can include one or more breathing monitors 152. The one or more breathing monitors 152 can monitor breathing of a user while using the structure 150. The breathing data acquired can be analyzed to determine breathing patterns, changes in breathing patterns, breathing rates, and/or changes in breathing rates of the user. Breathing data can be used to improve the geometric design definition so that the breathing of users associated with subsequent structures can be improved, dynamically adapted, or made more comfortable.

The sensors 152 can include one or more heart rate sensors 152. The one or more heart rate sensors 152 can monitor a user's heart rate and changes in heart rate while using the structure 150. The heart rate data acquired can be analyzed to determine when the structure is being used, the length of use, and whether the use is periodic (e.g., on and off wear) or continuous (e.g., all day, all night). The heart rate sensor data can measure when the user in engaging in periods of high or low intensity exercise versus rest. Heart rate data can be used to improve the geometric design definition by optimizing the heart rate sensor placement on the structure 150 such that a user's heart rate can be reliably monitored.

The sensors 152 can include one or more blood pressure sensors 152. The one or more blood pressure monitors 152 can monitor a user's blood pressure and changes in blood pressure while using the structure 150. The blood pressure data acquired can be analyzed to determine when the structure is being used, the length of use, and whether the use is periodic (e.g., on and off wear) or continuous (e.g., all day, all night). The blood pressure sensor data can determine periods of high stress versus low stress for the user. Blood pressure data can be used to improve the geometric design definition by optimizing the blood pressure sensor placement on the structure 150 such that a user's blood pressure can be reliably monitored.

The sensors 152 can include one or more moisture sensors 152. The one or more moisture sensors 152 (also referred to as humidity sensors) can monitor sweating from the user. The moisture data acquired can be analyzed to determine the quantity a user is sweating, the user's sweat rate, and/or the structure's moisture content when the structure is being used. Moisture data can be used to improve the geometric design definition so that optimal sweating can be achieved (e.g., more or less sweating), and/or so that the humidity inside the structure 150 or between a user and a user contact surface of the structure 150 can be minimized or lessened. As another example, the moisture sensor data can determine when the user is engaging in periods of exercise versus rest. The moisture sensors 152 can be sweat sensors. The moisture sensors can measure moisture volume, for example, the volume of moisture absorbed by the sensor, the volume of moisture absorbed by the structure adjacent the sensor, the volume of moisture that passes through the sensor, or any combination thereof.

The sensors 152 can include one or more temperature sensors 152. While the user is using the structure 150, the one or more temperature sensors 152 (also referred to as thermal sensors and heat sensors) can monitor a user's temperature, can monitor a user's changes in temperature, can be used to produce a heat map of the user's body, or any combination thereof. Additionally or alternatively, the one or more temperature sensors 152 can monitor the environment temperature and changes in the environment temperature. Temperature data can be used to improve the geometric design definition so that the structure 150 has less or more of an effect on a user's temperature, and/or so that the temperature inside the structure 150 or between a user and a user contact surface of the structure 150 can be minimized or lessened (e.g., so that the optimal temperature can be achieved between the structure 150 and the user).

The sensors 152 can include one or more pressure sensors 152. The one or more pressure sensors 152 can monitor the pressure applied by the structure to the user. For example, the one or more pressure sensors 152 can monitor the pressure on muscles, tissue, bones, joints, bloods vessels, organs, or any combination thereof. The pressure data acquired can be analyzed to determine the pressures that the structure is applying to the user. The pressure sensor data acquired can be analyzed to determine when the structure is being used, the length of use, and whether the use is periodic (e.g., on and off wear) or continuous (e.g., all day, all night). Pressure data can be used to improve the geometric design definition by ensuring that the desired pressures are achieved against the user at the pressure sensor contact points.

The sensors 152 can include one or more force sensors 152. The one or more force sensors 152 can monitor the internal and external forces applied to the structure 150. The force data can be analyzed to determine the internal and/or external forces applied to the structure 150. Force data can be used to improve the geometric design definition by ensuring that the structure 150 is tolerant of internal and external impacts to the structure 150. The pressure sensor data acquired can be analyzed to determine when the structure is being used, the length of use, and whether the use is periodic (e.g., on and off wear) or continuous (e.g., all day, all night). External forces can be applied to the structure 150 from the environment such as impact forces from other objects. Internal forces can be applied to the structure from the user. Additionally or alternatively, internal forces can correspond to tensile and/or compressive forces that the structure 150 experiences. The compressive forces can be biomechanical forces.

The location of the sensors can be adjusted, or any component of the geometric design definition can be adjusted in response to data acquired and/or analyzed from one or more sensors 152.

Figure 2A:
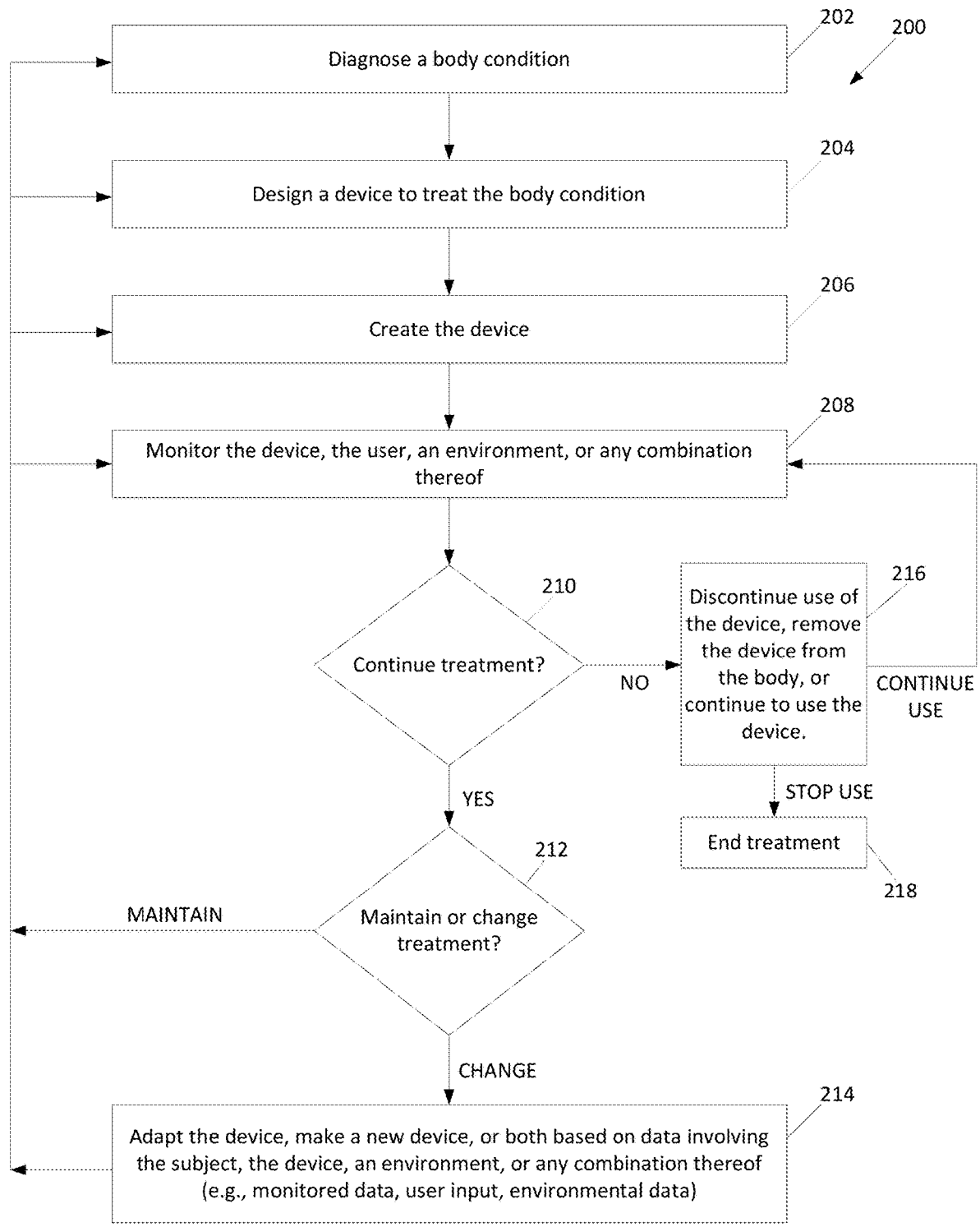
FIG. 2A illustrates a variation of a method undertaken by the system.

FIG. 2A illustrates a variation of a process 200 that is implementable using and/or performable by the system 100, using the system 100, or both. The method 200 can be used to diagnose and treat a subject (also referred to as the user and the patient). For example, the method 200 can be used to diagnose a subject (e.g., to diagnose a body condition of a subject), design a device 150 (e.g., a user-specific device 150) to treat the subject (e.g., to treat the diagnosed body condition), monitor the subject (e.g., monitor the diagnosed body condition and/or the treatment thereof), monitor the device 150 (e.g., monitor the device 150 that is created for the subject to treat the subject), monitor an environment near the device 150 (e.g., monitor the environment that the device 150 is in), reassess the body condition, recommend an adaptation to the device 150 (e.g., after a period of use, including wear and implantation, including sensor adjustment), recommend a modification of the device 150 (e.g., after a period of use, including wear and implantation, including sensor adjustment), diagnose of another body condition, a secondary condition, or any combination thereof.

For example, FIG. 2A illustrates that the method 200 can involve diagnosing a body condition (e.g., in operation 202), designing a device 150 to treat the body condition (e.g., in operation 204), creating the device 150 (e.g., in operation 206), monitoring the device 150, the user, an environment, or any combination thereof (e.g., in operation 208), determining whether to continue treatment based on monitoring data, a reassessment of the body condition, or both (e.g., in operation 210), determining to maintain or change the treatment (e.g., in operation 212), adapting the device, making a new device, a new device portion, or any combination thereof, for example, to change the device's effect on the body (e.g., in operation 214), discontinuing use of the device, removing the device from the body, or continuing use of the device (e.g., in operation 216), ending treatment (e.g., in operation 218), or any combination thereof, where ending treatment can include a recommendation to periodically monitor the body condition using, for example, the system 100 should the body condition not be improved or completely removed between operation 202 and operation 220 (e.g., where a scoliosis brace reduces the curvature of the spine but does not return the curvature to within normal limits, where a posture-correcting device reduces kyphosis but does not return the curvature to within normal limits, where a shoe insert or foot orthotic reduces pronation while running or walking but does not eliminate it entirely). Diagnosing the body condition can involve determining the extent of the body condition (e.g., in operation 202).

Operation 202 can involve creating one or multiple diagnostic tests to identify one or multiple body conditions (e.g., medical conditions, non-medical conditions), involving and/or including, for example, a user's finger, wrist, elbow, shoulder, arm, neck, spine (e.g., scoliosis), knee, hip, ankle, foot, toe, joint, conditions related to arthritis, fractures, degeneration, congenital, herniated disks, tumors, injury, infection, obesity, strain, sprain, osteoarthritis, spondylitis, compression fractures, deformed limbs, amputated limbs, avascular necrosis, pronation, supination, knee valgus, knee varus, tendonitis, torn ligaments, any body part or condition, or any combination thereof. The diagnosis can be performed by a computer (e.g., via the system 100) using the one or multiple diagnostic tests, by a person (e.g., a medical professional), by a person using a self-serve diagnostic test, by machine intelligence (e.g., a neural network), or any combination thereof. The method 200 can diagnose any body condition observable by a data acquisition device and can design a user-specific device to address the body condition. The above list is merely exemplary.

Any number of diagnostic tests can be performed in operation 202, for example, 1 to 10 diagnostic tests, or more broadly, 1 to 100 diagnostic tests, or more broadly still, 1 to 1,000 or more diagnostic tests, or less than 10,000 diagnostic tests, including every 1 diagnostic test within these ranges (e.g., 1 diagnostic test, 10 diagnostic tests, 1,000 diagnostic tests, 10,000 diagnostic tests, 10,001 diagnostic tests). Each diagnostic test (e.g., performed in operation 202) can involve recognizing (also referred to as detecting) the body condition of the subject based on data that includes, for example, symptoms of the body condition, the physical extent of the body condition, the physical extent or condition of the subject, or any combination thereof. Operation 202 can identify the subject's body condition, determine the extent (e.g., severity) of the body condition, determine the type treatment to treat the body condition (e.g., treatment with a user-specific device custom made for the user), and determine the fit requirements to effect the desired treatment. Operation 202 can involve executing each diagnostic test with or without the aid or input from a medical professional before, during and/or after the test. For example, operation 202 can include using the system 100 for data capture, recording, comparison, and analysis techniques to recognize the body condition with or without the aid or input from a medical professional. One or multiple data acquisition devices 102 can be used to acquire image data (e.g., body dimension data) and non-image data (e.g., heart and blood pressure data) from which symptoms of the body condition, the physical extent of the body condition, the physical extent of the subject, or any combination thereof can be determined. The acquired data can include images (e.g., pictures and/or videos) of the subject from one or multiple perspectives, for example, from the front, back, left, right and 360 degree view, x-rays and medical imaging, or any combination thereof. The acquired data can also include the subject's medical history and the subject's answers to one or multiple questions (e.g., on a standard medical questionnaire form) regarding their current health. The acquired data can include non-image data, including, for example, accelerometer data, barometer data, gyroscope data, scoliometer data, moisture data, pressure data, force data, heart rate data, blood pressure data, and/or data internal to the subject's body. Image data and/or non-image data can be used to diagnose the subject's body condition. For example, the system (e.g., via one or more images and/or scoliometer data) can capture images of the subject and then from those images determine the degree of curvature of the subject's spine where they have scoliosis. The acquired data can be, for example, images (x-ray images, CT scans, MRI images, 3D images, 2D images, endoscope images, nuclear medicine images, PET scans, mammography scans, DEXA scans, colonoscope images), image data, medical imaging data, sensor data, or any combination thereof. The acquired data can be acquired, for example, from one or more sensors, image acquisition devices, or both.

The diagnostic test (e.g., performed in operation 202) can involve identifying the body condition, the size, shape, and/or position of the body condition, the size, shape, and/or position of the subject (e.g., the entire subject or one or multiple areas of the subject), or any combination thereof, for example, via a processor analyzing data acquired by the data acquisition device 102. The size, shape, and/or position of the body condition can be fit characteristics (also referred to as fit parameters) for a device that can be designed to treat the identified body condition. The size, shape, and/or position of the subject can be fit characteristics (also referred to as fit parameters) for a device that can be designed to treat the identified body condition. For example, operation 202 can involve determining, for example, via a processor analyzing data acquired by the data acquisition device 102, one or multiple dimensions of the body condition and/or the subject, including, for example, dimensions of one or multiple external characteristics of the subject and/or body condition, dimensions of one or multiple internal characteristics of the subject and/or body condition, or both, such that the system 100 can design a device whose dimensions are determined based at least partly on measurements of the subject's and/or body condition's external characteristics, the subject's and/or body condition's internal characteristics, or both.

The external characteristics can be external structural characteristics of the body condition and/or the subject and can include, for example, the size and/or shape of the body condition, the size and/or shape of one or multiple body structures, the relative positions of body structures, the position of the body condition relative to one or multiple body structures, a map (e.g., contour map) of the outer surface of the body condition, a map (e.g., contour map) of the outer surface of the subject, range of motion of body structures, the surface area of the body structure or condition, measurements of the body structure or condition, circumference of body structure or condition, or any combination thereof. The internal characteristics can be internal structural characteristics (e.g., size, shape and/or relative positions of the body condition, body structures, relative positions of body structures, relative position of the body condition to other parts of the subject, maps of the internal surfaces of the subject, condition, or both, location of mapping of bones, organs, and tissues, measurement of fluid flow through the body, metabolism rate, or any combination thereof). The external characteristics can be, for example, dimensions, sizes, shapes and positions of body structures, body conditions, blood perfusion, heat map, moisture, or any combination thereof. The internal characteristics can be, for example, dimensions, sizes, shapes and positions of body structures, body conditions, blood perfusion, heat map, moisture or any combination thereof.

The acquired external and/or internal characteristics can be stored as data, for example, in a database of the system 100 (e.g., external database 114). The subject's internal and external physical digital data can include data collected by the system 100 (or other data acquisition systems) collected in the past, in the present, on a continuous basis (e.g., monitoring), or any combination thereof.

Operation 202 can include body condition identification parameters (also referred to as anatomical indicators) for one or multiple conditions, for example, from 1 to $N_{C-1}$ conditions, where $N_C$ can be the total number of conditions identifiable by the system (e.g., system 100). $N_C$ can range, for example, from 1 to 10, 1 to 100, 1 to 1000, less than 10000, including every 1 condition increment with these ranges. An acquired data set (e.g., image data from the system 100) can be analyzed, for example, via a processor analyzing data acquired by the data acquisition device 102, relative to the identification parameters using one or multiple data analysis techniques. $N_C$ can be static or dynamic such that the system 100 can create diagnostic tests based on (1) data acquired from the data acquisition device 102 and/or based on (2) body condition identification parameters (e.g., diagnostic tests) added to the system 100, for example, by being uploaded to any of the system 100 memories and/or databases, such that diagnostic tests can be created by the system 100 (e.g., by analyzing, via a processor of the system 100, data acquired by the data acquisition device 102), uploaded to the system 100, or both. For example, where $N_C$ is 3, the system 100 can set or determine parameters for a first body condition, a second body condition and a third body condition. Based on one or multiple data acquisition techniques, the system (e.g., system 100) can identify the first, second, and/or third body conditions. Based on one or multiple data acquisition techniques, the system (e.g., system 100) can identify the fit properties (also referred to as anatomic indicators) of the body condition and of the subject (e.g., determine the bounds/extent of the identified body condition and/or of the subject, where the entire subject or discrete areas of the body condition and/or the subject can be mapped). In this way, for example, the system 100 can identify a body condition (e.g., the first, second, and/or third body conditions) and identify the fit needs for a device to effectively treat the identified condition. The identification parameters can be pre-determined such that the identification parameters can be programmed into the operation 202.

For example, using one or multiple data acquisition techniques, operation 202 can involve determining the subject's condition (e.g., medical, non-medical), the severity of the condition, and the type of device treatment and fit requirements for the device can be determined. For example, operation 202 can identify the characteristics of the body condition that the device can be designed to treat inside the acquired data of the subject (e.g., using the acquired data of the subject). The device can be a wearable device. The device can be an implantable device. The device can be both implantable and wearable. For example, where the subject has scoliosis, the system 100 can diagnose the subject's scoliosis based on, for example, (1) a photo of the subject with non-level shoulders (e.g., one shoulder is higher than the other), (2) a photo of the subject with non-level hips (e.g., one hip is higher than the other), (3) a spine x-ray of the subject with a curvature of their spine, or any combination thereof. The system 100 can automatically diagnose the body condition (e.g., scoliosis), via the system 100, and then determine fit requirements for the device 150, also via the system 100. Another example, where the subject has a missing portion of his or her leg, the system 100 can determine the level of amputation and the topography of the end portion of the leg based on, for example, (1) a photo of the subject with or without a knee joint and without an ankle joint, (2) a photo of the patient with leg length discrepancy, (3) a leg x-ray of the subject showing or not showing a knee joint and not showing an ankle joint. The system 100 can automatically diagnose the body condition (missing leg), and then determine fit requirements based on topography of the end of the limb.

Operation 202 can involve analyzing acquired data, for example, from the data acquisition devices 102 via one or multiple processors. Based on analysis of the acquired data, locally or remotely relative to the subject 103T, to the data acquisition device 102, or both, operation 202 can involve diagnosing one or multiple body conditions. As another example, operation 202 can analyze the acquired data and based partly or entirely on this analysis diagnose one or multiple body conditions. The acquired data can include images (e.g., pictures and/or videos, point clouds, 3D scans, laser scans) of the subject from one or multiple perspectives, for example, from the front, back, left, right and 360 degree view, medical images, or any combination thereof.

For example, based on imaging, photos and/or videos from one or multiple perspectives of the subject, the method 200 (e.g., via the system 100) can automatically detect that (1) the subject is standing upright, (2) the subject's shoulder blades are not on an even plane, (3) the gap between the subject's body and arms are different on the subject's left and right sides, for example, between the subject's left arm and body and between the subject's right arm and body (e.g., when the arms are parallel to the body or at resting position while the subject is standing upright), (4) one leg is shorter than the other, (5) the subject's back or spine has a curvature, (6) the subject's body tilts to one side, (7) body measurements from head to toe (e.g., full body measurements, partial body measurements, or both, for example, including the subject's height), or any combination thereof. The one or multiple perspectives of the subject can include, for example, photos and/or videos from the front, back, left, right and 360 degree view, medical imaging, or any combination thereof.

As another example, based on photos and/or videos from one or multiple perspectives of the subject, the method 200 (e.g., via the system 100) can automatically detect that (1) the subject is in a forward bent position, that the palms of their hands are being held together, and that the subject is wearing no shirt, or only a bra, or any combination thereof, (2) the ribcage is rotated creating a hump, or any combination thereof. The one or multiple perspectives of the subject can include, for example, photos and/or videos from the front, back, left, right and 360 degree view, or any combination thereof.

As yet another example, based on photos, videos, medical imaging, accelerometer data, barometer data, gyroscope data, and scoliometer data, the system can capture the degree of curvature of the spine. This data can be acquired with data acquisition devices, for example, the photos and/or videos with an image capturing device (e.g., a camera), the medical imaging with a medical imaging device, a 3D scan with a 3D scanner, the accelerometer data with an accelerometer, the barometer data with a barometer, the gyroscope data with a gyroscope and the scoliometer data with a scoliometer (also referred to as an inclinometer). Using any combination of these data acquisition techniques and acquired data, the method 200 (e.g., via the system 100) can automatically detect, for example, that the subject is in a forward bent, palms of the persons' hand are together, and are wearing no shirt, or only a bra, or any combination thereof. The scoliometer can be a mobile phone with a scoliometer application. The scoliometer can be placed and/or run along the back of the patient to determine the curvature (and/or non-curvature) of the subject's spine. The scoliometer can be used, for example, to automatically detect spine curvatures by measuring the angle of trunk rotation (ATR), where a normal ATR can be from about 0 degrees to about 3 degrees, an intermediate ATR can be from about 4 degrees to about 6 degrees, and a relevant ATR (e.g., an ATR which indicates that it is highly probably that the user has scoliosis) can be about 7 degrees or greater (e.g., from about 7 degrees to about 50 or less degrees, including every 1 degree increment within this range). The method 200 can involve using the scoliometer, for example, to automatically detect whether the user's spine has a normal ATR, an intermediate ATR, a relevant ATR, or any combination thereof. The scoliometer can be a digital or a non-digital device. The scoliometer can be an electronic or a non-electronic device. For example, the scoliometer can be a phone, can be part of the phone, or can be scoliometer software on the phone. The scoliometer can provides the degree of the curvature of the subject's spine.

The method 200 (e.g., operation 202) can advantageously analyze acquired image data (e.g., from pictures and/or videos) be used in conjunction with acquired scoliometer data. For example, the acquired image data (e.g., photos or videos) can provide the relevant position of the scoliometer while the scoliometer measurements are taken, for example, while the scoliometer is moved and/or placed along the subject's back. Additionally or alternatively, a barometer, an accelerometer, and/or a gyroscope can be used to determine the relevant position of the scoliometer and how the scoliometer is run from a first position to a second position (e.g., from the bottom of the spine to the top of the spine), which can include from tailbone to the neck or any lesser portion (e.g., between any two vertebrae, between any two spinal disks).

The data acquisition device (e.g., device 102) can be a specialized jacket with sensors (e.g., pressure sensors, heat sensors, heart rate sensors, movement sensors, accelerometers, gyroscopes, temperature sensors, moisture sensors, blood pressure sensors). The subject can wear the jacket during data acquisition. Data from acquired from the jacket can be used to create a map of the subject's body showing their body shape, body size, relative positions of body structures (similar to a point cloud), temperature, or any combination thereof. For example, the sensors of the jacket can show the subject's body curvature, including, for example, curvature of the subject's spine.

As still yet another example, based on x-rays and/or other digital medical imaging from one or multiple perspectives of the subject, the method 200 (e.g., via the system 100) can automatically detect and measure the location and degree of each vertebrae and/or spinal disk with respect to each other and the subject's body. Operation 202 can advantageously allow the subject's spine (e.g., individual vertebrae and/or individual spinal disks) to be visible, for example, from the subject's neck to their tailbone or any lesser portion (e.g., between any two vertebrae, between any two spinal disks). Operation 202 can thereby automatically detect, for example, that (1) the subject is standing up upright, (2) the subject's spine is not in a straight line when they are standing upright, (3) the subject's spine has a curve (e.g., an S-shaped curve), kyphosis, lordosis, or any combination thereof. The curvature of the subject's spine can be measured to be more than 0 degrees, for example, between any two vertebrae, between any two spinal disks, or both. The one or multiple perspectives of the subject can include, for example, photos and/or videos from the front, back, left, right and 360 degree view, a photo or video at any angle increment and in any direction from any view of the patient, or any combination thereof. As another example, based on x-rays and/or other digital medical imaging from one or multiple perspectives of the subject, the method 200 (e.g., via the system 100) can automatically detect and measure the location and severity of a bone fracture. Operation 202 can advantageously allow the subject's bone to be visible, for example, from the subject's skull to their feet or any lesser portion (e.g., just the fractured bone). Operation 202 can thereby automatically detect, for example, that (1) the subject has inflammation in one area of the body, (2) the subject has a fracture in one of his or her bones, (3) the severity of the fracture, or any combination thereof. The one or multiple perspectives of the subject can include, for example, photos and/or videos from the front, back, left, right and 360 degree view, a photo or video at any angle increment and in any direction from any view of the patient, or any combination thereof.

As still yet another example, operation 202 can diagnose scoliosis from one or multiple photos (e.g., 1 to 10 photos, including every 1 photo increment within this range (e.g., 4 photos)), one or multiple x-rays (e.g., 1 to 10 x-rays, including every 1 x-ray increment within this range (e.g., 2 x-rays)), a pressure map of the body indicating the curvature of the body, a magnetic resonance image (MRI), a CT scan, or any combination thereof. As still yet another example, operation 202 can diagnose foot over-pronation from one or multiple photos (e.g., 1 to 10 photos, including every 1 photo increment within this range (e.g., 4 photos)), one or multiple x-rays (e.g., 1 to 10 x-rays, including every 1 x-ray increment within this range (e.g., 2 x-rays)), a pressure map of the foot striking the ground during stance and during normal gait and running gait, MRI, CT scan, or any combination thereof.

Operation 202 can further involve assessing the diagnosed condition and making a treatment determination. The treatment determination can be a recommended treatment. The treatment determination can be multiple recommendations, ranked in order of, for example, expected efficacy of the treatment, projected treatment duration, estimated subject comfort during treatment, anticipated subject compliance during treatment, or any combination thereof. Such factors can also be provided where only one recommended treatment is provided by the method 200. The treatment determination can involve designing one or multiple user-specific medical or non-medical devices to treat the diagnosed condition (e.g., medical or non-medical condition). The treatment determination can be based on, for example, (1) the diagnosed condition and (2) the fit parameters of the condition, (3) the fit parameters of the subject, (4) the treatment parameters (e.g., desired physical changes of the subject), or any combination thereof.

FIG. 2A further illustrates that the method 200 (e.g., in operation 204) can include addressing (e.g., treating) the identified body condition with one or multiple devices 150 that are custom designed to address (e.g., treat) the identified body condition of the target user.

Operation 204 can involve designing one or multiple devices 150 to address the body condition based at least partly on or entirely on data acquired and/or determined from operation 202. Addressing the body condition can involve affecting the progression of the body condition, for example, stabilizing the body condition, improving the body condition, inhibiting the body condition from becoming worse, preventing the body condition from becoming worse, or any combination thereof. As another example, addressing the body condition can involve changing the subject's body structure to maintain the current state of the body condition. As yet another example, addressing the body condition can include affecting (e.g., changing, maintaining, stabilizing, moving, or any combination thereof) subject's biomechanics, exerting external forces and/or pressures on the subject's body to redistribute forces and/or pressures inside the subject's body, exerting internal forces and/or pressures in the subject's body to redistribute forces and/or pressures inside the subject's body, or any combination thereof. Addressing the body condition can involve relieving, reducing, or eliminating pain or discomfort associated with the body condition. For example, operation 204 can design a medical device 150 that can relieve, reduce, or eliminate forces and/or pressures on one or multiple nerves in the subject's body (e.g., the sciatic nerve). As still yet another example, addressing the body condition can involve designing a medical device 150 that can adjust the relative positions of one or multiple body structures relative to one or multiple other body structures. For example, the designed medical device 150 can move or exert force and/or pressure on one or multiple tissues (e.g., bone, bone marrow, muscle, fat, skin, organs, soft tissue, non-soft tissue, teeth, tendons, ligaments) such that a body first structure (e.g., a first rib) is moved relative to a body second structure (e.g., a second rib, a first vertebra). The designed medical device 150 can induce or inhibit movement or range of motion, as well. The device 150 can be an invasive device, a non-invasive device, or both. The device can be configured to penetrate tissue, to not penetrate tissue, or both.

Operation 204 can involve designing implants, wearable devices, or both. For example, operation 204 can involve designing endovascular stents, joint replacements or implants (e.g., hip replacements, knee replacements, shoulder replacements, intrauterine devices), scoliosis braces, spine screws, rods, artificial disks, metal screws, pins, plates, rods, artificial knees, artificial hips, cervical plates, lumbar plates, facet screws, pedicle screw systems, fusion cages, intramedullary nails, bone screws, hip sterns, patient-specific implants, humerous plates, radius plates, surgical guides, surgical knives, orthotics, heel inserts, foot orthotics, ankle supports, ankle-foot orthoses, lower extremity walker boots, functional knee orthosis, knee immobilizer, knee ankle foot orthosis, reciprocating gait orthosis, lower extremity fracture orthoses or distal tibia/fibular fracture orthosis, hip abduction orthosis, body armor, or any combination thereof. The method 200 can diagnose design user-specific devices to address any condition observable by a data acquisition. The above list of devices is merely exemplary.

Operation 204 can involve designing a device to affect (e.g., treat) the body condition diagnosed in operation 202. For example, operation 204 can involve designing one or multiple three-dimensional (3D) models of a device 150 to treat the diagnosed body condition, for example, to treat the body condition diagnosed in operation 202. The models can be constructed from multiple two-dimensional (2D) images. The 2D and 3D images can be digital models.

Operation 204 can design a single model. Operation 204 can design multiple models (e.g., 2 to 20 or less models, 2 to 100 or less models, including every 1 model increment within these ranges). The multiple models can be a system of structures 150. The one or multiple 3D models can be configured to be worn by the subject or implanted in the subject. One or more of the 3D models can be configured to interact with at least one other 3D model. For example, operation 204 can design a first 3D model and a second 3D model. The first 3D model can be separate from the second 3D model such that they are not configured to engage with or otherwise interact with one another directly or indirectly or can be configured to interact with one another directly or indirectly. The first 3D model can be configured to fit a first portion of the target subject (also referred to as the subject) and/or of a first target body condition and the second 3D model can be configured to fit a second portion of the target subject, a second portion of the first target body condition, and/or a first portion of a second target body condition, or any combination thereof. The first and second target body conditions may or may not be related or interact with each other.

The design process (e.g., operation 204) can involve identifying the symptoms of the condition (e.g., in diagnosis step 202), identifying the fit needs for the medical device 150 (e.g., in creating/design step 204), identifying the data needed to recognize the body condition and the fit needs of the medical device 150 (e.g., in operation 202, 204, and/or a separate step different from operation 202 and/or 204), designing a 3D model that can address the specific body condition (e.g., in creating/design step 204), or any combination thereof. The fit needs can be the external and/or internal parameters of the subject, the body condition, or both.

The device 150 designed in operation 202 and/or in operation 204 can be designed to be wearable by the subject, implantable into the subject, or both. For example, the device 150 can be designed to cover a portion of an outer surface of the subject. For example, where the diagnosed condition is scoliosis, the curvature of the subject's spine from an x-ray can be recognized for diagnosis (e.g., in step 202), the body dimensions from one or multiple images (e.g., photos/videos) can be determined for fit (e.g., in operation 202 and/or 204), and the curvature of the spine on the x-ray and the determined body dimensions can be used to create a custom 3D model (also referred to as a user-specific 3D model) to fit the subject and/or their body condition (e.g., in operation 204), or any combination thereof.

The method 200 (e.g., via operations 202 and 204) can recognize (also referred to as diagnose) the condition in operation 202, can determine fit parameters of a treatment device (e.g., structure 150) using measured and/or determined external and/or internal parameters of the subject, can model the device using the external and/or internal parameters of the subject, and can construct the device (e.g., in operation 206). The device 150 can be made (e.g., via machine, by hand, or both), for example, in operation 206 using, for example, the manufacturing unit 106.

As another example, in operation 202 the condition can be recognized, in operation 202 the fit parameters for the subject and/or the body condition can be identified, selected, and/or determined (e.g., the size, shape and dimensions of the subject and/or the body condition can be measured), in operation 202 the fit parameters for the device can be identified, selected, and/or determined to fit or otherwise accommodate the fit parameters of the subject and/or the body condition. In operation 204 a user-specific device to address (e.g., treat) the diagnosed condition can be designed (e.g., modeled) based on the fit parameters for the device, and in operation 206 one or multiple devices can be created based partly or entirely on the fit parameters for the device, or any combination thereof. The fit parameters for the device are also referred to as device fit parameters. The device fit parameters can be determined and/or selected so that the device does or does not conform to or follow the contour of a surface of the subject. For example, the device can be a fixation device (cast) that follows the contour of the arm for a broken arm. The device can also be an implant is placed in the muscle, skin, or organs and does not follow the contour of a body part. The surface can be an external surface (e.g., surface of the skin), an internal surface (e.g., a tissue hammock that can hold organs in place), or both.

As yet another example, in operation 202 the condition can be recognized, in operation 202 the fit parameters for the subject can be identified, selected, and/or determined (e.g., the size, shape and dimensions of the subject can be measured), in operation 202 and/or operation 204 the fit parameters associated with the diagnosed condition can be identified, selected and/or determined (e.g., the size shape and dimensions of the body condition can be measured), in operation 202 the fit parameters for the device can be identified, selected, and/or determined to fit or otherwise accommodate the fit parameters of the subject and/or the body condition (e.g., when the physical extent of the subject and/or the condition is determined in operation 202), in operation 204 a user-specific device to address (e.g., treat) the diagnosed condition can be designed (e.g., modeled) based on the identified fit parameters for the subject, the body condition, and/or the device, and in operation 206 one or multiple devices can be created based partly or entirely on the identified, selected, and/or determined fit parameters for the subject, the body condition, and/or the device, or any combination thereof.

As still yet another example, in operation 202 the condition can be recognized, in operation 202 fit parameters for a device and/or the subject can be identified, selected, and/or determined, in operation 204 one or multiple treatment parameters for the device and/or the subject can be identified, selected and/or determined, in operation 204 the device can be designed based on the identified, selected, and/or determined fit and/or treatment parameters, in operation 206 one or multiple devices can be created based partly or entirely on one or multiple of the fit and/or treatment parameters, and in operation 206 the device or multiple devices can be created based partly or entirely on the one or multiple of the fit and/or treatment parameters, or any combination thereof. In operation 204 the device can be designed by generating a 3D model. The fit parameters can be external characteristics and the treatment parameters can be a desired change in an internal and/or external parameter of the subject, (e.g., a delta of a relative position between a first portion of the subject's body and a second portion of the subject's body). 3D models of the device 150 can be designed in operation 204. The 3D models can be configured to fit the subject.

The structure 150 can be created based on the data including the location, structure, and relative positions of the subject's tissues, for example, including bone, fat, muscle, skin or any combination thereof. For example, the structure 150 can be created based on the location, structure and relative positions of soft tissue (e.g., fat, muscle), hard tissue (e.g., bone), blood vessels, or any combination thereof.

Operation 204 can involve mapping the device 150 to the subject's inner and/or outer surfaces, to an intersection of inner and/or outer surfaces, to an interaction of inner and/or outer surfaces, to soft tissue, to hard tissue, one or multiple layers of tissue, or any combination thereof.

Operation 204 can involve designing the device 150 to fit the subject and/or their body condition based partly or entirely on data associated with the subject collected before, during, and/or after usage of the device 150.

For example, where the structure 150 designed in operation 204 is a scoliosis brace, the structure 150 can be configured to cover an outer surface of the subject (e.g., their torso, hips, chest, back, ribs, or any combination thereof), where the structure 150 can be created to cover the outer surface based partly or entirely on one or multiple measurements of the subject in operation 202 (e.g., based partly or entirely on the sizes, shapes and/or dimensions of the external and/or internal characteristics determined for the condition, the subject, or both). For example, the structure 150 can have dimensions and characteristics which can be determined based partly or entirely on measurements and/or one or multiple determined parameters (e.g., fit parameters, treatment parameters, or both) of the subject.

Operation 204 can involve personalizing the device 150. The method 200 (e.g., in operation 204) can include designing 3D models that include the personal preferences of the subject. The personal preferences incorporated into the device 150 can affect the structure of the device. Devices 150 with and without personal preferences can affect the body condition of the subject. The personal preferences may or may not change the design of the device 150. For example, a first device designed for a subject without personal preferences can achieve the same effect as a second device designed with personal preferences for the same subject. The first device can have the same or different structural designs as a result of the personal preferences in the second device and absence of personal preferences in the first device.

In operation 204 a device 150 can be designed with characteristics that can be uniquely created based on the preferences of the subject, based on the look and feel the subject desires for their user-specific device 150, based on the subject's desired comfort level while wearing the device, or any combination thereof. The personal preferences can include, for example, color, shape, and design of the device 150, or any combination thereof. For example, physical representations such as a cat face, mouse face, and/or embroidery can be incorporated into the device 150 that would not otherwise be incorporated into the device 150 but for the subject's personal preferences. The physical representations can be additional structures (e.g., additional material added to the device 150), can be open spaces in the device (e.g., cutouts not changing the efficacy of the device), or both.

The personal preferences can be incorporated into the design such that the personal preferences can be involved with addressing the body condition, such that when the device 150 is adapted to effect a different or the next treatment parameter, all or a portion of the personal preference can be adjusted or modified. For example, where the device 150 has a cat face, the device can be adjusted by adjusting the size, shape and/or dimensions of the cat ears. When the device 150 is adapted, the portion of the device 150 having the personal preference can be adjusted and/or modified, a portion of the device 150 not having the personal preference can be adjusted and/or modified, or both.

FIG. 2A further illustrates that the structure 150 can be designed with or without determining and/or using a geometric design definition (GDD) of a device modeled to fit a reference object 103R, where the subject and/or the body condition can be the target object 103T (also referred to simply as the subject or the user). The reference object 103R can be a reference subject with or without an observable body condition. The reference object 103R can be a reference subject with or without the same body condition as the target subject (also referred to simply as the subject or the user). A GDD can be determined and a reference 3D model designed and generated, for example, as disclosed in International Application No. PCT/US2017/064099 filed Nov. 30, 2017 (published as WO 2018/102625) and U.S. application Ser. No. 15/828,430 filed Nov. 30, 2017 (published as US 2018/0147062), both of which are herein incorporated by reference in their entireties for all purposes.

Where a GDD is determined, the method 200 can include creating a GDD of the body condition of the reference object 103R based on data that includes symptoms, characteristics, and the fit properties (e.g., anatomic indicators) of the body condition of the reference object 103R, and one or more areas of the reference object 103R (also referred to as the generic subject), or any combination thereof.

For example, the method 200 can include defining data capture, recording, comparison, analysis techniques to identify and map the body condition of the reference object 103R and/or of the body condition of the generic user, the fit characteristics of the body condition and/or of the generic subject, or any combination thereof.

As another example, the method 200 can include designing 3D reference models, for example, based on the GDD, where the 3D reference models can be configured to address the body condition of the generic subject across the generic subject or in or across one or more areas of the generic subject 103R (also referred to as discrete areas of the generic subject).

As yet another example, the method 200 can include designing 3D reference models, where the 3D reference models can be configured to fit the body condition of the generic subject across the generic subject or in or across one or more areas of the generic subject 103R (also referred to as discrete areas of the generic subject).

As still yet another example, the method 200 can include designing 3D reference models that specifically fits a discrete area of the generic subject 103R and addresses the body condition (e.g., the reference object 103R or the body condition of the generic subject 103R) in the discrete area in conjunction with or without other 3D reference models that fit another discrete area of the generic subject and addresses the discrete body condition in the other specific area. The method 200 can include addressing one or more body conditions of the generic subject 103R that may or may not be related or interact with each other.

As still yet another example, the method 200 can include designing 3D reference models, where the 3D reference models can dynamically adapt (e.g., can be fitted) to the generic subject 103R across the generic subject or in the discrete areas of the generic subject's body condition based on the generic subject's data collected before, during, and after the usage of the generic subject's device (e.g., device 150 designed for the reference object 103R) that addresses the body condition of the generic subject 103R.

As still yet another example, the method 200 can include designing 3D reference models, where the 3d reference models can dynamically affect the generic subject 103R across the generic subject or in the discrete areas of the generic subject's body condition based on the generic subject's data collected before, during, and after the usage of the generic subject's medical device (e.g., device 150 designed for the reference object 103R) that addresses the body condition of the generic subject 103R.

The device or devices 150 for the subject can be designed, modeled and made with or without a GDD. The device or devices 150 for the subject can be designed, modeled and made independent from or dependent on a GDD. The device or devices 150 for the subject can be derived from a GDD, for example, from the fit parameters of the GDD of the 3D reference model designed to fit the reference object 103R and/or address the body condition of the reference object 103R. The method 200 can determine the GDD of one or multiple reference objects 103R.

The same or different diagnostic techniques can be used for the reference and target objects 103R, 103T. Operation 202 can include confirming that the target subject's diagnosis is the same as the general subject's diagnosis, for example, by diagnosing the target subject and then cross-referencing this diagnosis with a database of generic subject diagnoses and then linking or pairing the target subject's diagnosis and/or the target subject to one or multiple geometric design definitions (GDDs) associated with a generic subject or a group of generic subjects with the same diagnosis.

Where a GDD is used to design the structure 150 in operation 204, the 3D reference models defined by the GDD can be adjusted to fit the target object 103T (also referred to as the subject, the user, and the target subject). For example, the method 200 can include (1) adjusting the generic model defined by the GDD designed to fit the generic subject or an average of generic subjects to fit a target subject, (2) adjusting the resulting target 3D model and/or device for the target subject independent of the GDD and independent of the generic model, for example, using wear data of the target subject, or as another example, using wear data of the target subject and comparing it to wear data of the generic subject, and as yet another example, using wear data of the generic subject, or any combination thereof, (3) designing the device or devices 150 independent of or without reference to a GDD, or any combination of (1) to (3). The average of generic subjects can be an average of dimensions of multiple reference objects 103R. The reference object 103R can have previously been a target subject 103T. The reference object 103R can simultaneously be a target object 103T. For example, a first target object 103T1 can be a reference object 103R for a second target object 103T2 and the second target object 103T2 can be a reference object 103R for the first target object 103T1.

The method 200 can involve defining the GDD and adjusting the GDD to fit the target subject. As another example, the method 200 can involve first defining the GDD and then adjusting the GDD to fit the target subject.

The method 200 can include (e.g., in operation 204) creating 3D target models (e.g., defined by the GDD) by adjusting a 3D reference model (e.g., defined by the GDD) to map the device 150 to the subject's inner and/or outer surfaces, to an intersection of inner and/or outer surfaces, to an interaction of inner and/or outer surfaces, to soft tissue, to hard tissue, one or multiple layers of tissue, or any combination thereof.

Operation 204 can involve designing the device 150 (e.g., using a 3D reference model defined by the GDD and/or using a 3D target model defined by the GDD) to fit the target subject and/or their body condition based partly or entirely on data associated with the target subject collected before, during, and/or after usage of the device 150, based partly or entirely on data associated with the reference subject collected before, during, and/or after usage of the device 150, or both. As another example, a first device 150a can be designed using a GDD and a second device 150b can be designed with or without a GDD. The first and second devices 150a, 150b can be configured to interact with one another or not interact with one another while worn by and/or implanted in the target subject. As another example, first portion of a device 150 can be designed using a GDD and a second portion of the device 150 can be designed with or without using a GDD such that two or more portions of the device 150 can be designed, modeled, and created differently.

Operation 204 can design a single device 150, a series of devices 150, or both. Where a series of devices 150 is designed, the series can be a predetermined series of devices 150 such that the entire series is designed before the user starts using the first device in the series, or the series can be designed one device at a time such that each next device 150 in a series can be designed during or after the user uses each current device 150 in the series (e.g., the third device in a series can be designed during or after the user uses the second device in the series). Designing a series one device at a time can advantageously allow each device 150 in the series to inform or impact the design of the next device 150 in the series. Each subsequent device in a series can be an entirely new device (e.g., an entirely new scoliosis brace) or can be an adaptation of the previous device in the series (e.g., the tightening of a strap of a scoliosis brace from a strap first position to a strap second position). For example, operation 204 can include designing 1 to $N_{D-1}$ devices, where $N_D$ can be the total number of devices 150 designed in operation 202 and/or 204. $N_D$ can range, for example, from 1 to 10, 1 to 100, 1 to 1000, less than 10000, including every 1 device increment within these ranges.

Operation 204 can design a day device (e.g., configured to be worn during the day or while the subject is awake), a night device (e.g., configured to be worn during the night or while the subject is asleep or resting), a day-night device (e.g., configured to be worn at any point over the 24 day irrespective of the time of day), or any combination thereof. The day device variations can be custom designed to depend on, for example, the subject's activities, the subject's activity level, or both. The night device variations can be custom designed to depend on for example, the subject's preferred sleeping position (e.g., on their back, stomach, left side, right side). The day-night device can incorporate design features of the day device, the night device, or both.

FIG. 2A further illustrates that operation 206 can involve making the device or devices 150 designed in operations 202 and/or 204. For example, one, multiple or all of the designed devices $N_D$ can be made by the system (e.g., system 100), for example, in operation 206, or can be made by a manufacturing unit (e.g., person, machine, or both) different from the system from which operations 202 and/or 204 are executed by (e.g., different from the system 100 to which operations 202 and/or 204 belong). The manufacturing unit 106 can be a person, machine, or both. Operation 206 can make a single device 150, a series of devices 150, or both. Operation 202 and/or 204 can involve simulating the device 150, for example, via finite element analysis, augmented reality, virtual reality, or any combination thereof.

The device 150 can be adaptable, for example, adjustable, modifiable, or both. The device 150 can be an adaptable device (e.g., adjustable, modifiable). The device 150 can be a static device (e.g., not adjustable, not modifiable).

The devices 150 can be designed and created with one or multiple structural properties, multiple parts inter-connected, material properties, or both. The one or multiple devices 150 can be created with one or multiple material or structural properties, for example, based on measurements and/or data determined, generated, or collected in operations 202 and/or 204.

For example, when the device 150 is worn by the subject (e.g., a scoliosis brace), based on the correction required, the device 150 can cover the subject from the breast area in the front through to the pelvic area, can cover the subject from the neck area in the back through the hips and right above the buttocks, or both. Some parts of the cover contains special designs and personalization elements created based on the personal preferences of the subject.

The device 150 can be made of one or multiple device elements. The device elements can be interlocking parts, interconnected parts, or both. The device elements can be connected to each other. The device elements can be permanently or temporarily engageable with one another. Each device element can engage with one or multiple other device elements. The device elements can include struts. The device elements can be telescopable elements. The device elements can include joints. The device elements can include parts of the device itself. The device elements can be connected at joints. The struts can be connected at joints. The struts, joints, or both can define cells. The cells can be openings in the device 150. A flexible and/or rigid component can be in the open cells, cover the open cells, cover the device elements, or any combination thereof. The device elements can have male ends, female ends, or both (e.g., one of each). The male ends can fit into the male ends, for example, with a screw fit, friction fit, glue fit, or any combination thereof. The device elements can be flexible. The device elements can be rigid. The device elements can be elastic. The device elements can be inelastic. The device elements can be made of a shape memory alloy (e.g., Nitinol). The device 150 can be solid. The device 150 can be hollow. The device 150 can receive one or more body structures (e.g., the subject's torso, limbs, neck). One or multiple of the device components (e.g., interlocking parts) can be solid or hollow. The device can be expandable, compressible, stretchable, compressible, or any combination thereof.

The device elements can be adaptable, for example, adjustable, modifiable, or both. One or multiple device elements can be movable relative to another device element, for example, to change the device from a device first configuration to a device second configuration. The device elements can allow the device 150 to be adapted such that the relative position between at least two device elements can be changed. As another example, the device elements can allow the device 150 to be adapted such that a dimension between at least two device elements can be increased, decreased, or both. Changing the relative position and/or a dimension between at least two device elements can change how the device 150 fits the subject when worn by the subject. For example, changing the relative position and/or a dimension between at least two device elements can make the fit between the subject and the device 150 tighter in one or multiple locations, looser in one or multiple locations, or both.

For example, a dimension between a first device element and a second device element can be increased (e.g., to loosen the fit of device, to lessen the force/pressure applied by the device 150 to the subject, or both), a dimension between the first device element and the second device element be decreased (e.g., to tighten the fit of the device 150, to increase the force/pressure applied by the device 150 to the subject, or both), a relative position between the first device element and the second device element can be changed (e.g., to loosen the fit of device, to lessen the force/pressure applied by the device 150 to the subject, to tighten the fit of the device 150, to increase the force/pressure applied by the device 150 to the subject, or any combination thereof), or any combination thereof. One, all, or some of the device elements can be increased or decreased (e.g., to loosen the fit of device, to lessen the force/pressure applied by the device 150 to the subject, to tighten the fit of the device 150, to increase the force/pressure applied by the device 150 to the subject, or any combination thereof), or any combination thereof. As another example, a dimension and/or relative position between a device first element and a device second element can be changed to adapt the device from a device first configuration to a device configuration such that the device first and/or second elements can be configured to apply more or less force to the subject's body in the second configuration than in the first configuration. One or multiple dimensions between device elements can be adapted by adjusting the relative positions of the device elements to each other, for example, moving the device first and second elements such that a dimension between them is increased or decreased. One or multiple dimensions between device elements can be increased, for example, to decrease the overall pressure and/or force exerted on the subject by the device 150. One or multiple dimensions between device elements can be decreased, for example, to increase the overall pressure and/or force exerted on the subject by the device 150. The compression and/or tension that the device 150 is configured to apply to the subject's body can be increased and/or decreased by adapting the device from a device first configuration to a device second configuration, vice versa, or both.

The relative positions of the device elements can adapted (e.g., adjusted, modified) to change the size, shape, and/or dimensions of the device 150. A modification can include, for example, the addition or removal of material (e.g., device elements), and an adjustment of the device can include, for example, movement of one or more device elements relative to one another. Adjusting and/or modifying the device 150 can physically change the size, shape, and/or dimensions of the device. For example, the device 150 can be adapted to have a smaller size, a larger size, a different shape, or any combination thereof.

The device 150 can be adapted to accommodate progression of the body condition, growth of the subject, aging of the subject, or any combination thereof. The progression of the body condition can be a positive progression (e.g., improvement of the condition), a negative progression (e.g., worsening of the condition), or a neutral progression (e.g., no change in the condition). Adapting the parts of the device 150 can result in no change in the number of contact points between the subject and the device 150 or can result in an increase or decrease in the number of contact points.

The device 150 can have one or multiple device portions, for example, 1 to $N_{DP-1}$ devices, where $N_{DP}$ can be the total number of device portions. $N_{DP}$ can range, for example, from 1 to 10 or less, 1 to 50 or less, 1 to 200 or less, including every 1 device portion increment with these ranges. For example, the device 150 can have a device first portion, a device second portion, a device third portion, a device fourth portion, or an combination thereof, where the device first portion can be a front of the device, where the device second portion can be a back of the device, where the device third portion can be a first side of the device, and where the device second portion can be a second side of the device. Each device portion can be made of, for example, device elements. The devices can be modular. For example, the device portions can be modular relative to each other.

Some or all of the device elements and/or device portions can be patterned to increase the strength of each element and/or portion to change the density, volume area, and strength of the device 150, or any combination thereof.

The device 150 can treat pronation, supination, varus knee, valgus knee, slouching posture, hyperextension of the knee, extreme lordosis or kyphosis, limited lordosis or kyphosis, bracing for fractures or injuries, or any other body condition. For example, where scoliosis is treated, based on the degree of the curvature of the spine in connection with the shape of the subject's body, one or multiple device elements and/or one or multiple device portions (e.g., a device front, a device back, a device side) can be created to apply the appropriate level of pressure and/or force to the spine to correct the curvature to treat the scoliosis. The pressure and/or force on the body can be increased, for example, by increasing the tension between two or more of the device elements and/or device portions covering the body. The pressure and/or force on the body can be decreased, for example, by decreasing the tension between two or more of the device elements and/or device portions covering the body. For example when there are two device portions, one in the front (e.g., on the subject's chest) and one on the back (e.g., on the subject's back), each device portion can be locked to each other at 1 to 100 or more points, including every 1 point increment within this range (e.g., 1 point, 2 points, 3 points, 50 points, 100 points) and at 1 to 20 or more points, including every 1 point increment within this range (e.g., 1 point, 2 points, 3 points, 20 points) a locking mechanism can allow for adjustment of the distance between the two parts of the device 150 (e.g., a brace), hence increasing and/or decreasing the tension and the pressure and/or force applied to the body and hence to the spine, adjusting the spine to its ideal position.

The device 150 can have a lining. The device can have a lining integrated with one or more portions of the device. The lining can be formed of sensors. The lining can be an inner lining (e.g., on an inner surface of the device), an outer lining (e.g., on an outer surface of the device), or both. The inner lining can be permanently or removably attached to the device 150, for example, to a surface of the device. The surface can be a device inner surface, a device outer surface (e.g., a surface that faces away from the subject when the device 150 is worn by the subject), or both. The device can be configured to contact the subject, the subject's clothing, or both. The surface can, for example, face a device center longitudinal axis, toward a device chamber, or both. The surface can, for example, face away from a device center longitudinal axis, away from a device chamber, or both. Using the lining, the pressure and/or force applied by the device 150, and the subject's body form (e.g., size, shape, and/or dimensions) can be measured and tracked, or any combination thereof.

The device 150 can have one or multiple adaptable mechanics that can advantageously allow the device 150 to be adjusted, modified, or both, for example, based on tracking data (also referred to as monitoring data). The adaptable mechanics can include, for example, one or multiple actuators, one or multiple soft robotics, one or multiple mechanical assemblies, or any combination thereof. The device 150 can be adjusted in real-time, for example, via a controller in wired or wireless communication with a processor. The processor can be configured to process instructions received from the controller. The processor can send signals to the one or multiple adaptable mechanics of the device, for example, to change the device from a device first configuration to a device subsequent configuration (e.g., a device second configuration), vice versa, or both. The instructions can be manually entered via a control interface (e.g., by the user, by the user's parents by a medical professional) and then sent to the device 150, can be automatically determined by the method 200 (e.g., in operation 214), or both. The control interface can be, for example, a smartphone, an interface integrated with the device 150, or both. The device can also be auto-adjusting, where the sensor feedback tells the device whether to adjust or to remain static. For example, if the pressure sensor between the remaining portion of a patient's leg and the prosthetic limb socket is measured to be higher than the threshold of acceptable pressures as determined by physicians, potentially leading to soft tissue damage and pressure sores, The structure 150 designed via the method 200 (e.g., in operation 204) can force a body part of the subject to take a new shape, for example, by forcing the body part into alignment with another body part or parts. For example, where the structure 150 is a scoliosis brace (also referred to as a spine mover), the spine mover 150 can align the subject's spine, for example, from a first curved condition to a second curved condition less curved than the first curved condition. The spine mover 150 can advantageously force the subject's spine into a new shape, inhibit the subject's spine from moving into a new shape, prevent the subject's spine from moving into a new shape, maintain the subject's spine in the current shape, or any combination thereof.

Operation 208 can involve monitoring (also referred to as tracking) the device 150, the user, an environment, or any combination thereof. The device 150, the user, and/or the environment can be monitored with one or multiple data acquisition devices 102 (e.g., one or multiple sensors, one or multiple image capturers). For example, the device 150 can monitor the user, itself, and/or the environment, for example, via the one or multiple sensors 152, one or multiple cameras, or both. The cameras can be on the user, off the user, controlled (e.g., driven) by the user, automatically guided, or any combination thereof. The environment can be the environment in which the user, the device 150, or both are in. Monitoring the user can include reassessing the body condition, for example, with operation 202. The user can be monitored while the device 150 is being worn by the user, while the device is not being worn by the user, while the device 150 is or is not implanted in the user, or any combination thereof.

Operation 208 can involve monitoring the device 150 (e.g., via sensors 152) on a periodic or continuous (also referred to as an ongoing basis) during usage of the device 150 by the user, during implantation in the user, or both. For example, the orthodontic trays and scoliosis braces disclosed herein can be monitored on an ongoing basis through their usage by the user or on a periodic basis when being used by the user. Periodic tracking can include for example, tracking the device only when worn by the user, tracking the device at preset times (e.g., once every hour, once every 4 hours, once every 8 hours, once every 24 hours, once every 1-31 days and every 1 day increment within this range, once every 3 months, once every 6 months, once every year), tracking the user, the device, and/or the environment less than continuously. Continuous tracking can include tracking the user, the device, and/or the environment 24 hours per day, whenever one or more sensors are activated during use or implantation, or both. As another example, the tracking protocol can be defined by the subject's treatment plan which can include, for example, a device prescription that provides when and how to wear the device or devices 150. For example, the treatment plan can include a prescription to wear the device or devices 150 continuously (e.g., 24 hours per day) or during one or multiple wear periods (e.g., 8 hours per day, 12 hours per day, the morning, the afternoon, the evening, while awake, while asleep, during the day, during the night).

The data monitored in operation 208 can be individually and collectively referred to as monitoring data (also referred to as tracking data). The monitored data can include monitoring 1 to $N_{M-1}$ parameters, where $N_M$ can be the total number of monitored parameters monitored in operation 208. $N_M$ can range, for example, from 1 to 5, 1 to 10, 1 to 25, 1 to 100, including every 1 parameter increment within these ranges. For example, the monitored data can include monitoring any parameter measurable, detectable, or observable by the sensors 152. As another example, the user, the device, and/or the environment may or may not be monitored, may or may not have sensors configured to monitor the user, the device, and/or the environment, may or may not monitor the monitored parameters, or any combination thereof. Operation 208 can monitor the monitored parameters, changes in the monitored parameters, or both. The monitored data can be measured at device contact points, at device non-contact points, or both. The device 150 can be configured to contact the user at the contact points. The device 150 can be configured to not contact the user at the non-contact points. When the device 150 is adapted from a device current configuration to a device adapted configuration (also referred to as a subsequent device configuration), a contact point can remain a contact point, a contact point can become a non-contact point, a non-contact point can remain a non-contact point, a non-contact point can become a contact point, or any combination thereof. A device adapted configuration can be any device configuration different from the device's current device configuration.

The monitored parameters can include, for example, (1) a body displacement and/or a body structure displacement parameter, (2) a device-to-body pressure parameter (e.g., a measurement of the pressure exerted against the user's body by the device 150), (3) a device-to-body force parameter (e.g., a measurement of the force exerted against the user's body by the device 150), (4) a heat and/or temperature parameter (e.g., of the environment, of the user, and/or of the device 150), (5) a moisture parameter (e.g., humidity of the environment), (6) a perspiration parameter (e.g., perspiration of the user), (7) a heart rate parameter, (8) a blood pressure parameter, (9) an accelerometer parameter (e.g., the position and/or movement of the device), (10) a barometer parameter (e.g., the environmental pressure, for example, the atmospheric pressure that the device is in), (11) a gyroscope parameter, or any combination thereof, where the parameters can be detected, measured, or observed, for example, via the sensors 152. Data from sensors (e.g., sensors 152) can be analyzed by the device 150 and/or the system 100 to quantify (e.g., measure) the monitored parameters. The monitoring data can be collected. The monitored data can be represented on a map of the body, for example, a map of the body can be electronically displayed on a display and the monitored data or a subset thereof can be displayed to the user or to someone who is not the user (e.g., the user's parents, a medical professional), or both. The map can be monitor map, for example, a body structure displacement map, a movement map, an anatomical change indicator map, a pressure map, a force map, a parameter map (e.g., showing any of the monitored parameters), or any combination thereof. The monitored data can be displayed in real-time and/or determined and stored when accessed by the data viewer (e.g., the user or someone who is not the user).

The monitored data can indicate one or multiple things. For example, the monitored data, changes in the monitored data and/or thresholds exceeded by the monitored data can indicate (1) that the device was worn properly, (2) that the device was not worn properly, (3) that the device has achieved its desired effect, (4) that the device has achieved its desired effect and hence a new and/or adapted device is needed to apply more pressure/force to the subject, (5) that the device needs to be tightened, (6) that the device needs to be loosened, (7) that the device elements needed to be adapted to increase and/or decrease the force applied to the subject's body, (8) the subject's compliance with a treatment plan (e.g., the number of hours the subject wore the device, the number of times have the device was donned, the number of time the device was taken off), (9) a comparison of the monitored data with what was expected of the subject per the prescription (also referred to as their treatment plan) (e.g., how many hours has the expected pressure been applied? Was the applied pressure at the expected pressure level throughout the day or only portions of the data?), (10) device motion data, sensor motion data, user motion data, relative motion data between the device and the user, or any combination thereof, including for example, any combination of (1) to (10). As another example, heart rate, blood pressure, accelerometer, gyroscope and/or barometer data can be tracked to determine if the changes in, for example, pressure/heat/perspiration is related to changes in the activity level of the subject. The monitored data can be monitored across population groups and analyzed.

The monitored data can be shared with the person responsible for the subject (e.g., the subject's parents, the subject's caregiver), for example, to increase the subject's compliance with the treatment plan. The treatment plan can include a prescription to wear the device or devices 150 continuously (e.g., 24 hours per day) or during one or multiple wear periods (e.g., 8 hours per day, 12 hours per day, the morning, the afternoon, the evening). The parents can have access to the subject's monitored data, can be provided access to the subject's monitored data, or both. Sharing data with or giving access to the subject's parents can advantageously encourage the subject to comply with the treatment plan. The parents can have real-time access to the data.

The monitored data can be shared with the maker of the device, the designer of the device for remote adjustment, the manufacturer, or any combination thereof for remote analysis of the device, remote analysis of the subject, or both.

The monitored data can be shared with a medical professional (e.g., doctor, physician's assistant, nurse practitioner, nurse) for determining the efficacy of the device. As another example, method 200 can analyze the monitored data and determine the efficacy of the device. The monitored data can be shared with a medical professional (e.g., the subject's doctor) to increase the subject's compliance with the treatment plan. The medical professional can have access to the subject's monitored data, can be provided access to the subject's monitored data, or both. Sharing data with or giving access to a medical professional can advantageously encourage the subject to comply with the treatment plan. The medical professional can have real-time access to the data.

The monitored data can be shared with the subject, for example, to increase the subject's compliance with the treatment plan. For example, the monitored data can be shared with the subject for increased compliance through a gaming and/or reward based system or method.

The device 150 can provide feedback to the subject, and/or to the body condition through electrical or mechanical signals to improve the treatment of the subject and/or the body condition, for example, to create a better fit between the device and the subject and/or the body condition, so that the subject permanently conforms and adopts to the structure of the device, or any combination thereof. For example, for a scoliosis brace 150, the scoliosis brace can be configured to apply pressure, electrical, and/or mechanical signals to achieve the desired change in the body shape and body spine to adopt the body and the spine to its new form based on the desired effect. This can advantageously dynamically affect the patient in real-time. The feedback can be dynamic such that the feedback can change depending on, for example, the state of one or more of the monitored parameters. The feedback can be provided via one or multiple adaptable mechanics, vibratable elements, electrodes, sound producers (e.g., speakers), light producers (e.g., lights), temperature sensation producers (e.g., a warm sensation producer, a hot sensation producer, a cool sensation producer, a cold sensation producer), or any combination thereof. The adaptable mechanics can include, for example, one or multiple actuators, one or multiple soft robotics, one or multiple mechanical assemblies, or any combination thereof.

FIG. 2A further illustrates that operation 210 can involve making a determination whether or not to continue treatment. The determination can be made, for example, based partly or entirely on an observed anatomical change of the subject, when the device 150 achieves a desired anatomical change of the subject (e.g., a threshold change), one or multiple indications derived from one or more of the monitored parameters, a reassessment of the body condition (e.g., medical condition), or any combination thereof. Continued treatment can be recommended as indicated by the "YES" between operations 210 and 212 or the termination of treatment can be recommended as indicated by the "NO" between operations 210 and 216. The "YES' indication can be an N score, for example, scaled from 1 to 100 including every 1 unit increment within this range, including every 10 unit increment within this range, including every 25 unit increment within this range, or any combination thereof, where a lower score (e.g., closer to and/or equal to 1) can be an indication to continue and a higher score (e.g., closer to and/or equal to 100) can be an indication that means less likely to continue or to return the device to a previous configuration associated with an earlier stage in the treatment, such that the scaled score can indicate the probability of having the diagnosed condition, where a score of 0 indicates with 99% or 100% certainty that the patient does not have a body condition, and where a score of 100 indicates with 99% or 100% certainty that the patient does have a body condition.

FIG. 2A further illustrates that where the termination of treatment in operation 210 is recommended that operation 216 can involve discontinuing use of the device 150 or removal of the device 150 from the subject as indicated by "STOP USE" between operations 216 and 218, where operation 218 can be the end of the treatment. FIG. 2A further illustrates that where the termination of treatment in operation 210 is recommended that operation 216 can involve the user continuing use of the device 150, for example, as indicated by "CONTINUE USE" between operations 216 and 208.

FIG. 2A further illustrates that where the continuation of treatment in operation 210 is recommend that operation 212 can involve making a determination whether to maintain or change the treatment that the device 150 is configured to provide to the subject. The determination can be made, for example, based partly or entirely on an observed anatomical change of the subject, when the device 150 achieves a desired anatomical change of the subject (e.g., a threshold change), one or multiple indications derived from one or more of the monitored parameters, a reassessment of the body condition (e.g., medical condition), or any combination thereof. Maintained treatment (e.g., no change in the device 150) can be recommended as indicated by the "MAINTAIN" between operations 212 and 208 or a treatment change (e.g., an adaptation of the treatment, stopping the current treatment and starting a new treatment, and/or maintaining the current treatment and starting an additional treatment) can be recommended as indicated by the "CHANGE" between operations 212 and 208, where "CHANGE" can include adapting the device 150 or creating a new device 150.

FIG. 2A further illustrates that operation 214 can involve adapting the device 150, the user (e.g., their behavior), or both. For example, operation 214 can involve adapting the device 150 and/or making a new device 150 based partly or entirely on (1) the user's body condition, (2) the anatomic indicators of the body condition, (3) the shape, size and dimensions of the body condition, (4) the shape, size and dimensions of one or multiple target body structures, (5) the shape, size and dimensions of one or multiple non-target body structures, (6) monitoring data (e.g., the progression of any of (1)-(5), sensor data associated or unassociated with (1)-(5), user wear data, the progression of any of the disclosed, contemplated and/or illustrated monitored data), (7) user input (e.g., their comfort and/or discomfort with the device), (8) any of (1)-(8) acquired from or determined for another user or users, or any combination of (1)-(8). As another example, operation 214 can involve adapting the device 150 and/or making a new device based partly or entirely on the extent of the body condition, the progression of the body condition (e.g., changes in the body condition), device wear data or the lack thereof, for example, based on motion and sensor data, data collected before, during, and after the usage of the subject's device, the impact/effect of the subject's device on the subject's body condition, or any combination thereof. The device 150 can be adaptively regenerated (also referred to as adapted) and/or a new device 150 can be made based on motion and sensor data (e.g., using sensors 152) periodically during or continuously throughout usage. For example, for a scoliosis brace 150, the scoliosis brace can be adapted by increasing the tightness of the brace on the body gradually (e.g., incrementally) through screws or actuators or soft robotics that can be adjusted automatically, manually, or both. As still yet another example, the device 150 can be adapted and/or a new device 150 can be designed when the monitor map, parameter, and sensor changes. If the monitor map changes, operation 214 can determine why the map changed, for example, whether due to the device 150, due to growth of the subject (e.g., from a growth spurt), due to the clothes of the subject (e.g., wearing thicker clothes or thinner clothes as compared to a previous monitored map), due to the subject not wearing the device (e.g., due to someone else wearing the device), or any combination thereof. The device sensors can measure tension between two or more points of the device 150. The device 150 can be adapted and/or adjusted when the measured tension falls within a desired range, falls outside the desired range, or both. One or multiple desired ranges can be programmed into the device.

The device can be dynamically adaptable, for example, capable of providing dynamic feedback to the subject and/or to the body condition through electrical and/or mechanical signals to improve the adjustment of the subject and/or the body condition to create a better fit and to permanently adopt the structure of the subject to the structure of the device. This can advantageously dynamically affect the patient in real-time. The electrical and/or mechanical signals can, for example, provide the subject with a gentle nudge to as a reward to maintain their current behavior (e.g., maintain their current posture, maintain the current position of the device), change their current behavior (e.g., change their current posture, change the current position of the device, or both. One or multiple signals can be communicated to the subject via the device to correct the position of their device, to keep wearing the device, to take off their device, to adapt their device, or any combination thereof. The dynamic feedback can be linked to another device the subject wears or carries, such as a phone, computer, clothing or any combination thereof. One or multiple signals can be communicated to this other device to alert the subject, for example, via a ring and/or vibration of their phone to remind the subject to wear their device, to take off their device, to adapt their device, or any combination thereof. The feedback can be provided, for example, by one or multiple adaptable mechanics, vibratable elements, electrodes, sound producers (e.g., speakers), or any combination thereof. The adaptable mechanics can include, for example, one or multiple actuators, one or multiple soft robotics, one or multiple mechanical assemblies, or any combination thereof.

The device adaptations can be non-predetermined such that the adaptations are not determined during the design of the device, prior to the subject wearing the device, prior to acquiring monitoring data, or any combination thereof. This can advantageously allow the device 150 to be custom adapted based on the subject's behavior, the subject's response to treatment, or both. The device can be designed, however, to allow for the device to be adapted using one or multiple adaptation techniques. For example, the device can be adapted from a device first configuration to device second configuration by automatically and/or manually adjusting and/or modifying the device (e.g., the device elements, the device portions) to change the size, shape, and/or dimensions of the device which can, for example, tighten the fit of the device, stretch the device, expand the device, loosen the fit of the device, compress the device, collapse the device, change the device's monitoring capabilities, change the device's user feedback (e.g., dynamic feedback) capabilities, or any combination thereof. The device first configuration can be the initial configuration of the device or any subsequent device configuration, where the subsequent configuration can be a configuration adapted from a previous configuration (e.g., the device initial configuration or a device subsequent configuration). The device initial configuration can be the device configuration when the device is initially made. The device initial configuration may or may not be adapted before the subject wears or the device is implanted into the subject for the first time. For example, the device initial configuration can be but need not be adapted before the subject wears or the device is implanted into the subject for the first time. The device 150 can have a device initial configuration and a device final configuration. The device 150 can have one or multiple intermediate device configurations between the device initial configuration and the device final configuration.

The adaptation techniques can include, for example, adjusting one or multiple device elements (e.g., lengthening, shortening, and/or curving (e.g., bending) at least one device element), modifying one or multiple device elements (e.g., adding at least one device element, removing at least one device element), adjusting the size, shape and/or dimensions of one or multiple device portions (e.g., by adjusting and/or modifying device elements), adding at least one device portion, removing at least one device portion, adding at least one device, changing the location of one or multiple sensors, changing one or multiple sensors, adding one or multiple sensors, removing one or multiple sensors, changing the location of one or multiple monitoring sensors, changing one or multiple monitoring sensors, adding one or multiple monitoring sensors, removing one or multiple monitoring sensors, changing the location of one or multiple subject feedback devices (e.g., electrodes), changing one or multiple subject feedback device, adding one or multiple subject feedback devices, removing one or multiple subject feedback devices, or any combination thereof.

The device adaptations can be predetermined and/or not predetermined. For example, the device adaptions can be predetermined and/or not predetermined such when the device is adapted from a device first configuration to a device second configuration, the adaptation is a previously determined adaptation or is not a previously determined adaption. None, some, or all of the device adaptations can be predetermined. None, some, or all of the device adaptations can be not predetermined. For example, one or multiple device adaptions can be planned or unplanned. As another example, a series of successive device adaptations can be planned or unplanned. Whether an adaptation is planned or unplanned, the adaptation can be an expected and/or anticipated adaptation. However, when the adaptation is planned or predetermined, the device 150 can be designed so that the planned adaptation can be easier to manually or automatically achieve than if the planned adaptation was not predetermined or unplanned. For example, operation 204 can, for example, estimate one or multiple device adaptations (e.g., a series of two or more device adaptations) and design the device 150 to be adaptable from a device initial configuration to a device final configuration. The adaptations can be adapted based on the subject's behavior, the subject's response to treatment, monitoring data, subject's comfort with the device, or any combination thereof. As another example, the device adaptations can be predetermined, for example, based on the treatment plan. In such cases the predetermined adaptations can be projected adaptations, estimated adaptations, expected adaptations, or any combination thereof. The predetermined adaptations can be adapted based on the subject's behavior, the subject's response to treatment, monitoring data, subject's comfort with the device, or any combination thereof. For example, the devices 150 can be a series of predetermined orthodontic trays, where each tray can be adaptable, can adaptively change, can be capable of providing dynamic feedback to the subject, or any or all of the three.

The device adaptations can be achieved without remaking the device, without destroying the device, without breaking the device, or any combination thereof. The device adaptations can be permitted by the original design of the device. The device adaptations can be part of the design of the device, part of the device treatment plan, or both.

The device 150 can be adapted to the subject and/or the body condition such that the device 150 can be adapted (e.g., refit, dynamically adapted) to better fit the condition's progression, for example, by changing the device size, shape and/or dimensions from a device first configuration to a device second configuration. In this way, for example, the method 200 can be an adaptive platform that can design many different devices that fit very many conditions, can adapt the condition to the subject as the subject's body shape changes, as the subject's behavior changes, or both. For example, after usage of the device 150 gets to a point when the applied/measured pressure or the fit is no longer satisfactory to produce the desired anatomical change in the subject, a new device 150 can be created and/or the device can be adapted to meet the new state of the subject and/or the condition to produce the desired anatomical change in the subject and/or the condition. For example, the device 150 can be configured to produce a desired first anatomical change of the subject and/or condition. Once the desired first anatomical change is achieved, once the anatomical change stabilizes before, at, or beyond the desired first anatomical change, and/or when the desired anatomical change is below, at, or above a threshold rate of change, the device 150 can be adapted and/or a new device 150 can be designed to achieve a desired second anatomical change, where the desired second anatomical change can be the same type or a different type of anatomical change as the first anatomical change.

For example, the device 150 can be configured to reduce the subject's spine curvature from a spine first curvature to a spine second curvature (e.g., from radius of curvature of 40 degrees to a radius of curvature of 30 degrees), for example, while the device is in a device first configuration (e.g., a device initial configuration, a device second configuration, a device initial configuration, or any device subsequent configuration). The device 150 can then be adapted from the device first configuration to a device second configuration where the device second configuration can be configured to reduce the subject's spine curvature from the spine second curvature (e.g., radius of curvature of 30 degrees) to a spine third curvature (e.g., to a radius of curvature of 20 degrees). As another example, once the device 150 changes the subject's spine curvature from the spine first curvature to the spine second curvature, a new device 150 can be designed and made to urge the subject's spine from the spine second curvature to the spine third curvature.

The device 150 can be adapted and/or a new device 150 can be designed and/or made when the desired anatomical change of the device 150 is achieved, when the desired anatomical change stabilizes before, at, or beyond the desired first anatomical change, when the desired anatomical change is below, at, or above a threshold rate of change, or any combination thereof. For example, for a scoliosis brace 150, a first device 150 can urge (e.g., force) a spine having a 40 degree curvature to 30 degrees at which point the device shape, size and/or dimensions may be insufficient to produce any further anatomical change (e.g., further reduction in the spine curvature, may be insufficient to produce the desired anatomical change (e.g., rate of reduction of the spine curvature), or both, such that the scoliosis brace 150 can be adapted and/or a new device 150 can be designed to produce the desired anatomical change in the subject. If the desired anatomical change is not achieved by the adapted or new device 150, the device 150 can be redesigned or adapted. For example, for a scoliosis brace, if the pressure points of the brace 150 are too small or too large to create a desired change in pressure against the subject, the brace 150 can be redesigned or adapted to increase or decrease the size of the pressure points, for example, by increasing or decreasing the surface of one or more sections of the brace that are configured to apply pressure to the subject.

The device 150 can be adapted, for example, when the subject grows out of the device (e.g., where the subject is a child, where the subject gains or loses weight, where the subject has an abnormal growth that increases or decrease in size (e.g., a tumor), or any combination thereof).

The device 150 can support and correct body conditions of children, adults, animals or any or all of the above. As another example, the device 150 can support and correct body conditions of children and can support body conditions of adults. As yet another example, the device 150 can be a support device for use after surgery or injury that can be specific to surgery or injury recovery, a surgical device, a cutting device, or a scalpel.

Adapting the device 150 via the method 200 (e.g., in operation 214) can include adapting the 3D target models, where the 3D target models can be dynamically adapted to the subject based on the subject's data collected before, during, and after the usage of the device. In this way, the device 150 can dynamically affect the subject, for example, affect the subject with a first group of forces when the device is in a device first configuration and affect the subject with a second group of forces different from the first group of forces when the device is in a device second configuration different from the device first configuration. For example, a device can have its dimensions adaptively regenerated based on motion and sensor data while the user is wearing the device, during a treatment plan but when the user is not wearing the device, or both, where the regenerated device can include any adaptation of the device's dimension (e.g., adjusted, modified, or both). For example, for a scoliosis brace 150, the scoliosis brace can have a structural shape or material that can adapt based on the changes in the body such as bone growth or increase or decrease in body fat. The adaptation of the 3D target models can be simulated, approved by the system 100, or both. The 3D target model adaptations can be implemented in the device 150 manually, automatically, or both. The device can be manually and/or automatically adjusted with or without adapting a 3D target model. The device can be manually and/or automatically adjusted with or without first adapting a 3D target model.

The adapted 3D models can be configured to fit the subject, can be configured to address the current state of the body condition of the subject after the use of a previous device by the subject (e.g., an immediately preceding device), or both.

The devices 150 can have a device first configuration and one or multiple subsequent device configurations (e.g., a device second configuration different from the device first configuration, a device third configuration different from the device first and/or second configurations, and so on, for example, to 10 or less subsequent device configurations, 100 or less subsequent device configurations, 1000 or less subsequent device configurations, including every 1 device configuration increment within these ranges). The devices can be adjusted, modified, reconfigured, or any combination thereof into one or multiple subsequent device configurations, for example, from a device first configuration into a device second configuration different from the device first configuration. For example, a single device 150 can have 1 to $N_{DC-1}$ device configurations, where $N_{DC}$ can be the total number of device configurations. $N_{DC}$ can range, for example, from 1 to 5, 1 to 10, 1 to 25, 1 to 100, 1 to 1000, 1 to 10000, including every 1 device configuration increment within these ranges. A single device can thereby function as a series of devices that are each adaptable (e.g., adjustable, modifiable, reconfigurable, or any combination thereof) to affect one or multiple body structures of the user, one or multiple body functions of the user, or both. As another example, a device can thereby be changed into a series of devices that are each adjustable, modifiable, reconfigurable, or any combination thereof to affect one or multiple body structures of the user, one or multiple body functions of the user, or both.

A single device can be part of or not part of a series of multiple devices. For example, each device can be a stand-alone device that is not part of an intended or unintended series of multiple devices. In such variations, a device can be adjusted, modified, or reconfigured into a series of device configurations that can achieve the same effects as a series of multiple devices. For example, where the devices are orthodontic trays, a single orthodontic tray can be adjusted, modified and/or reconfigured either by the system, doctor, or user, such that a series of separate orthodontic trays can be replaced with less than the number of orthodontic trays in the series (e.g., 1 tray, 2 trays, 3 trays), where each orthodontic tray can function as a series of multiple different orthodontic trays. As another example, the devices can be part of a series of devices. For example, the devices can be devices that are part of an intended or unintended series of devices. A device series can have, for example, 2 to 10 or less devices, 2 to 50 or less devices, 2 to 100 or less devices, including every 1 device increment within these ranges (e.g., 5 devices, 10 devices, 15 devices, 50 devices, 100 devices). Each device in the series can be adjustable, modifiable, reconfigurable, or any combination thereof. As another example, some or all of the devices in a series of multiple devices can be non-adjustable, non-modifiable, non-reconfigurable, or any combination thereof.

The devices can be designed and applied to the user over time to stabilize the target body structure, change a body structure (e.g., reposition a body structure), move a body structure, or any combination thereof.

For example, where the device 150 is a scoliosis brace, the device 150 can be designed and applied to the user over time in order to change (e.g., reposition, move) the subject's spine in successive steps. The device 150 can be configured to be adjusted in increments, for example, in increments of 1 mm to 5 mm, 1 mm to 10 mm, 1 mm to 100 mm, including every 1 mm increment within these ranges. The device 150 can thereby be configured to move the spine (e.g., change the shape of the spine) in successive increments, where the successive use of the device 150 in each of its configurations permits the device 150 to progressively move the spine in increments of about less than 25 mm, less than 10 mm, less than 5 mm, less than 2 mm, less than 1 mm, less than 0.5 mm, or any combination thereof. As another example, the device 150 can thereby be configured to move the spine (e.g., change the shape of the spine) in successive increments, where the successive use of the device 150 in each of its configurations permits the device 150 to progressively change the one or multiple radii of curvature of the subject's spine in increments of about less than 25 degrees, less than 10 degrees, less than 5 degrees, less than 2 degrees, less than 1 degree, less than 0.5 degrees, or any combination thereof. The increments can refer to the maximum linear translation of any point of a vertebra or spinal disk as a result of using the device 150 in one of its configurations. The device 150 can be adapted (e.g., adjusted, modified, or reconfigured) so that the device 150 can function as a series of devices such that the successive device configurations can differ in their spine-conforming configuration by less than 25 mm, less than 10 mm, less than 5 mm, less than 2 mm, less than 1 mm, less than 0.5 mm, or any combination thereof, respectively, and/or can differ in their spine-conforming configuration by less than 25 degrees, less than 10 degrees, less than 5 degrees, less than 2 degrees, less than 1 degree, less than 0.5 degrees, or any combination thereof.

The method 200 can be an adaptable software platform. The method 200 can be a data platform. The method 200 can involve algorithm learning. The learning methods can include machine learning, online machine learning, online learning, or any combination thereof. For example, one or multiple operations in the method 200 (e.g., any one operation or subset of the operations) can use supervised and/or unsupervised online learning with machine learning techniques such as computer vision, statistical learning, deep learning, differential geometry, mathematical topology, natural language processing, including, regression, Markov models, support vector machines, Bayes Classifier, clustering, decision trees, neural networks, or any combination thereof. The system 100 can use such learning algorithms to iteratively improve the estimation and/or determination of the device adaptations, for example, in operation 214.

The operations 202, 204, 206, 208, 210, 212, 214, 216 and 218 can be interchangeably combined, rearranged, substituted, and/or omitted in any combination, and can be executed in any order, for example, in the order shown in FIG. 2A. Additional operations that are not shown can be added to the method 200 or can be part of a separate implementable and/or performable method. For example, the method 200 can involve repeating and performing operations 202, 204, 206, 208, 210, 212, 214, 216 and 218 in any order and in any combination. As another example, the monitoring, treatment decision, and device adaptation operations 208, 210, 212 and 214 can be repeated, for example, until a desired anatomical change of the body condition is achieved, including maintenance, improvement, or removal of the body condition of the subject. The data, results, and/or outcomes of every step in the method 200 can improve each step in the outcome in the method 200.

Operations 202, 204, 206, 208, 210, 212, and 214, or any combination thereof, can be iterated until a desired anatomical change of the subject is achieved, maintained, or both.

Figure 2B:
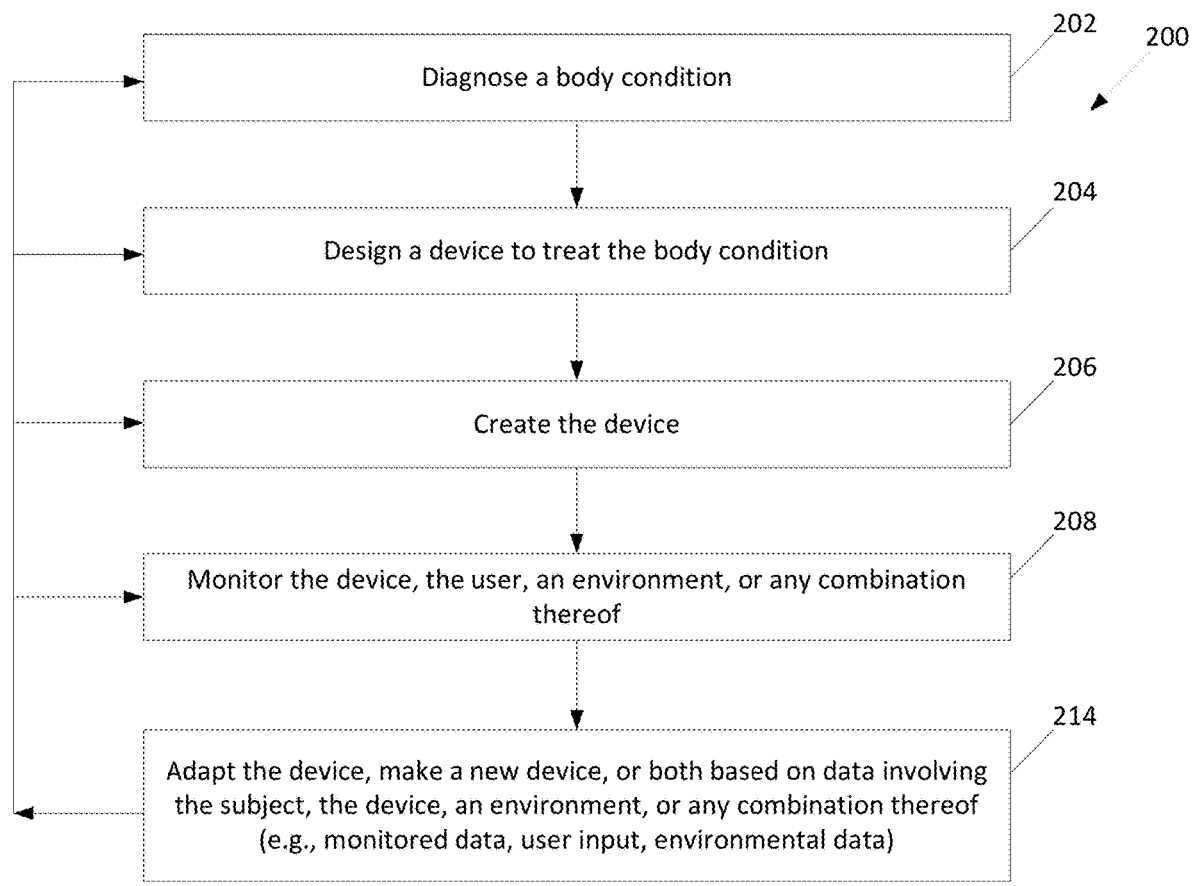
FIG. 2B illustrates a variation of a method undertaken by the system.
Figures 3A, 3B, 3C, 3D:
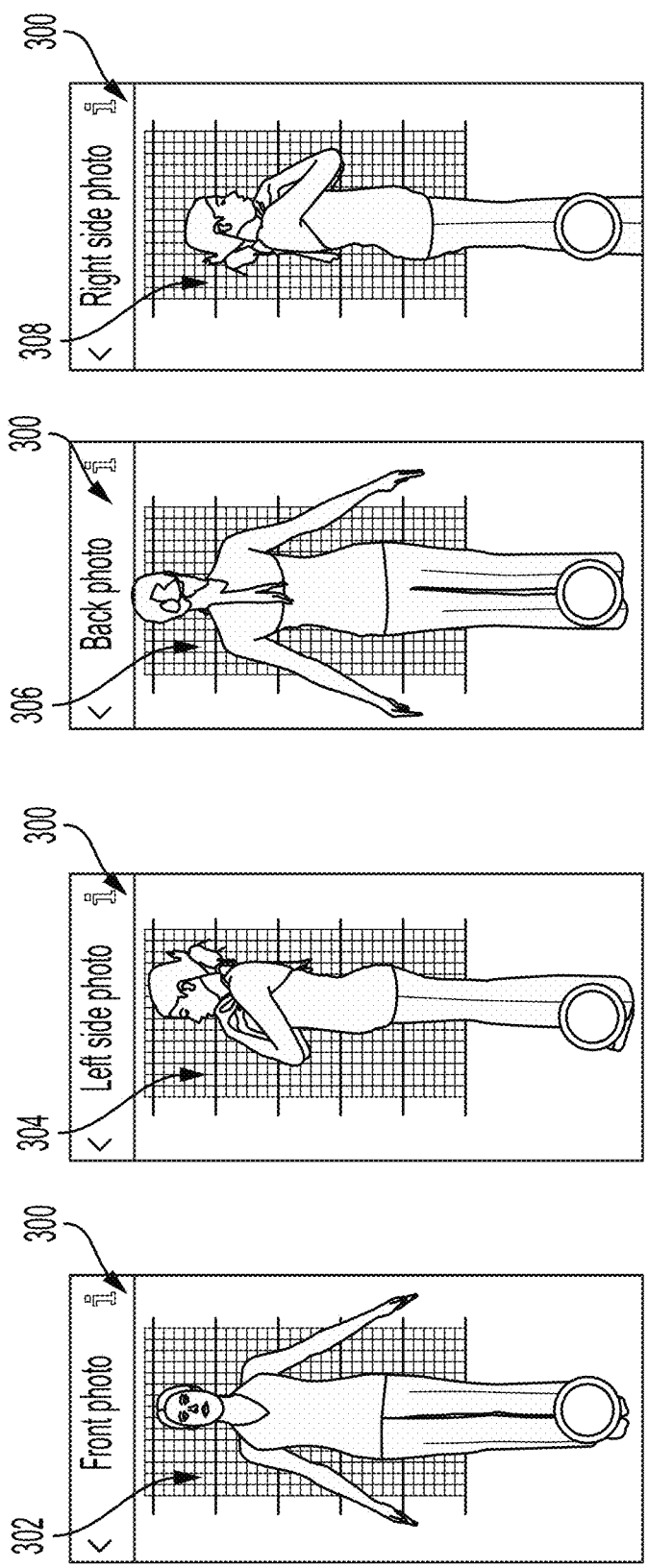
FIG. 3A illustrates a variation of a graphical user interface.
FIG. 3B illustrates a variation of a graphical user interface.
FIG. 3C illustrates a variation of a graphical user interface.
FIG. 3D illustrates a variation of a graphical user interface.

For example, FIG. 2B illustrates another variation of the process 200 that is implementable using and/or performable by the system 100, using the system 100, or both.

FIG. 2B illustrates that the method 200 can involve operations 202, 204, 206, 208 and 214 and that these operations, or any combination thereof, can be iterated until a desired anatomical change of the subject is achieved, maintained, or both.

The operations 202, 204, 206, 208 and 214 can be interchangeably combined, rearranged, substituted, and/or omitted in any combination, and can be executed in any order, for example, in the order shown in FIG. 2B. Additional operations that are not shown can be added to the method 200 or can be part of a separate implementable and/or performable method. For example, the method 200 can involve repeating and performing operations 202, 204, 206, 208, and 214 in any order and in any combination. As another example, the monitoring, treatment decision, and device adaptation operations 208, 210, 212 and 214 can be repeated, for example, until a desired anatomical change of the body condition is achieved, including maintenance, improvement, or removal of the body condition of the subject.

The body conditions referred to throughout can include any treatable condition or non-treatable condition, where treatment can include improvement of the condition, stabilization of the condition, non-worsening of the condition, or any combination thereof. Non-treatable conditions can be conditions that cannot be improved, but that can be stabilized or prevented or inhibited from becoming worse.

The devices can include, for example, orthoses, orthopedic devices, assistive devices, prostheses, implants, non-medical devices, non-medical structures, or any combination thereof. The devices can be supportive devices, corrective devices, therapeutic devices, surgical devices, or any combination thereof. For example, the devices 150 can support but not correct a body condition. As another example, the devices 150 can support and correct a body condition. The device 150 can support and/or correct the condition (e.g., medical condition) of the subject.

The devices can provide support to and/or correct alignment of a portion of a subject's body. For example, the devices can include joint braces (e.g., for wrists, ankles, knees, elbows, sacroiliac joints), back braces (e.g., scoliosis braces), implants (e.g., rods, screws, pins, plates for bones, artificial discs), external fixation devices for internal and external support for bones, replacement joints (e.g., for knees, elbows, hips), splints (e.g., for bones), bone fracture repair components (e.g., rods, screws, plates), or any combination thereof. The assistive devices can include, for example, canes, crutches, walkers, wheelchairs (e.g., for subject's with cerebral palsy), or any combination thereof.

The prostheses (also referred to as prosthetic devices) can include, for example, limb prostheses (e.g., arm prostheses, leg prostheses), ocular prostheses, extremity prostheses (e.g., hands, fingers, feet, toes), breast prostheses, face prostheses (e.g., nose prostheses), or any combination thereof.

The implants can include medical and/or non-medical implants. For example, the medical implants can include implantable devices such as stents, vascular connectors (e.g., anastomotic connectors), artificial heart valves, artificial organs (e.g., hearts), spinal cages, or any combination thereof. The non-medical implants can include, for example, cosmetic implants.

The non-medical structures can include, for example, fashion products such as clothing (e.g., dresses, pants, shirts), hats, and gloves designed to fit under the device, over the device, or configured to house the device.

FIGS. 3A-3D illustrate that the data acquisition device 102 can acquire a front image 302, a left image 304, a back image 306, a right side image 308, respectively, or any combination thereof, of a subject. The data acquisition device 102 can acquire the images in any order. As another example, the data acquisition device 102 can acquire a 360 degree view of the subject. The 360 degree view can be a video, can be a series of photos, for example, a series of photos taken every 1 degree to 45 degree increment in the 360 degree photo pan, including every 1 degree increment within this range, or both. The subject can be a generic subject or a target subject. The data capture in FIGS. 3A-3D can be performed, for example, before, during, or after operation 202. The data capture in FIGS. 3A-3D can be a data capture for a scoliosis brace, where, for example, the images in FIGS. 3A-3D can be acquired before or after operation 202 diagnoses that the subject has scoliosis.

FIGS. 3A-3D further illustrate that the acquired image can be displayed on a data display device (e.g., a smartphone, computer display) having a graphical user interface (GUI), for example, a GUI 300 having the features displayed in FIG. 3A-3D. The data display device can be the data acquisition device 102. The data display device can be an on device GUI. The data display device can have multiple data acquisition devices 102.

FIGS. 4A-4G illustrate a variation of a body condition screening application 400 as performable using the data acquisition device 102, where the screening application can be displayed on the GUI 300. The body condition screening and/or diagnosis application can be a computer algorithm or web-based platform. The body condition screening application can be a downloadable smartphone application. The body condition screening application 400 can guide the user of the data acquisition device 102 through the various steps, can automatically proceed to a next step when step has been completed, or both. For example, the body condition application can guide a user of the data acquisition device through steps 402, 404, 406, 408, 410, 412, and/or 414.

Figure 4A:
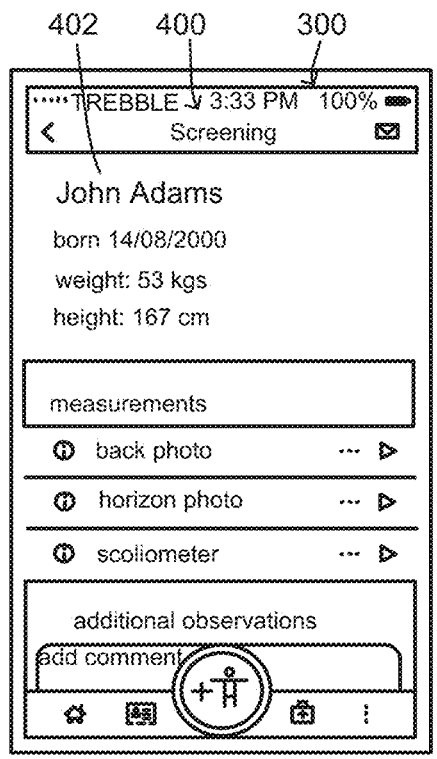
FIG. 4A illustrates a variation of a graphical user interface.

FIG. 4A illustrates that the body condition screening application can include screening navigation content 402 displayed by the GUI 300 with the features shown, for example, subject identifying data, selectable measurements (e.g., back photo, horizon photo, scoliometer), an additional observations sections for the screener (e.g., medical professional) to input into the data acquisition device 102, selectable touch screen buttons (e.g., a home screen, an insurance input button, patient or guardian input button), or any combination thereof.

Figure 4B:
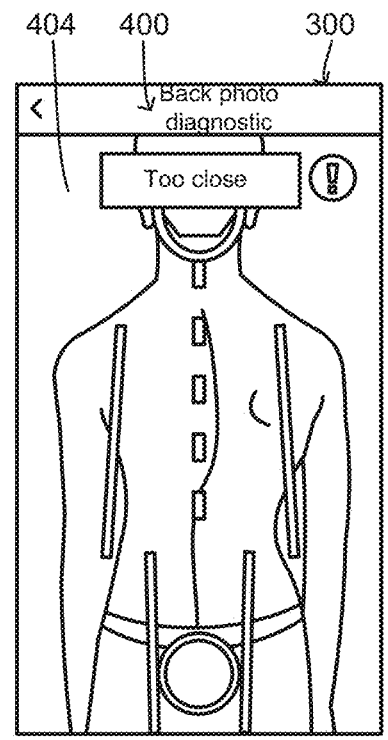
FIG. 4B illustrates a variation of a graphical user interface.

FIG. 4B illustrates that the body condition screening application 400 can include back photo diagnostic content 404 with the various features shown on the GUI 300. For example, the body condition screening application 400 can indicate that that the data acquisition is too close to the subject (e.g., as shown in FIG. 4B), too far from the subject, an acceptable distance from the subject, or any combination thereof. One or multiple alignment bars can be displayed on the GUI 300 before, during, and/or after the back photo is acquired.

Figure 4C:
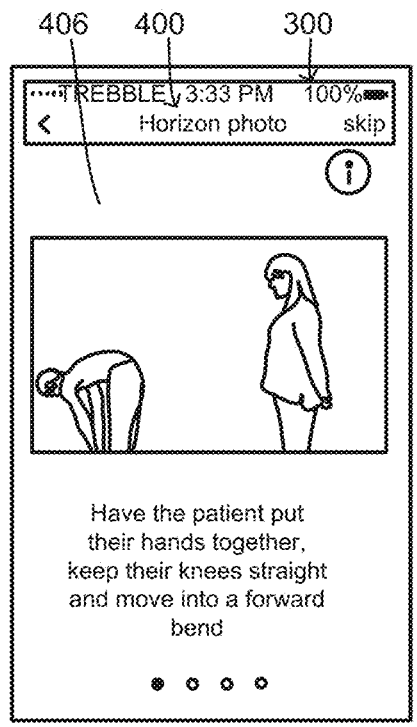
FIG. 4C illustrates a variation of a graphical user interface.

FIG. 4C illustrates that the body condition screening application 400 can include instruction content 406 with the various features shown on the GUI 300. For example, the instruction content 406 can provide instructions for how the subject should position their body for a horizon photo (e.g., "Have the patient put their hands together, keep their knees straight and move into a forward bend").

Figure 4D:
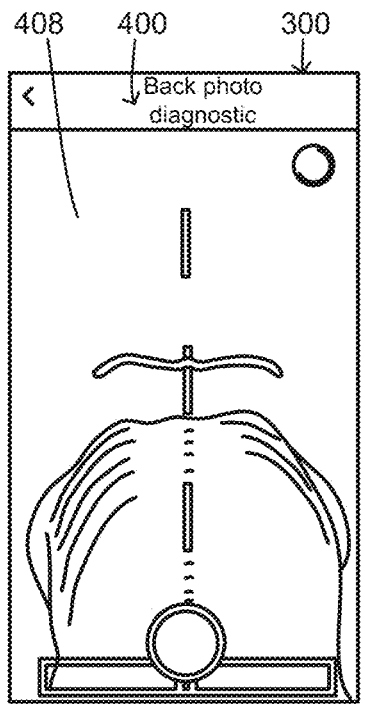
FIG. 4D illustrates a variation of a graphical user interface.

FIG. 4D illustrates that the body condition screening application 400 can include back photo diagnostic content 408 with the various features shown on the GUI 300. One or multiple alignment bars can be displayed on the GUI 300 before, during, and/or after the back photo is acquired.

Figure 4E:
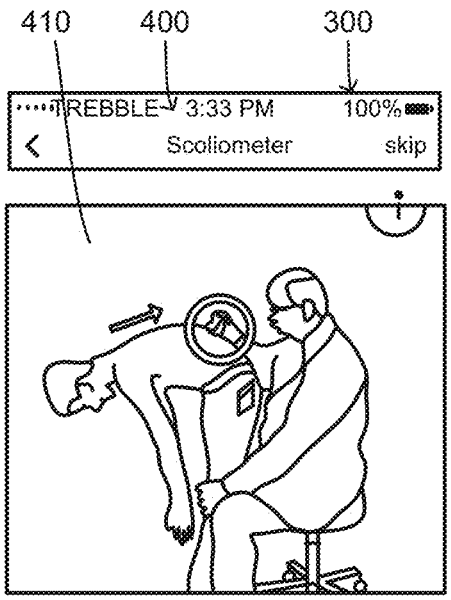
FIG. 4E illustrates a variation of a graphical user interface.

FIG. 4E illustrates that the body condition screening application 400 can include instruction content 410 with the various features shown on the GUI 300. For example, the instruction content 410 can provide instructions for how the subject and data acquisition device user should position their bodies for a scoliometer measurement and how the data acquisition user should use the scoliometer (e.g., "Sit behind the patient. You're going to slide your device down the patient's spine while they're in a forward bend."), where the scoliometer can be the same or different data acquisition device as the device having the GUI 300.

Figure 4F:
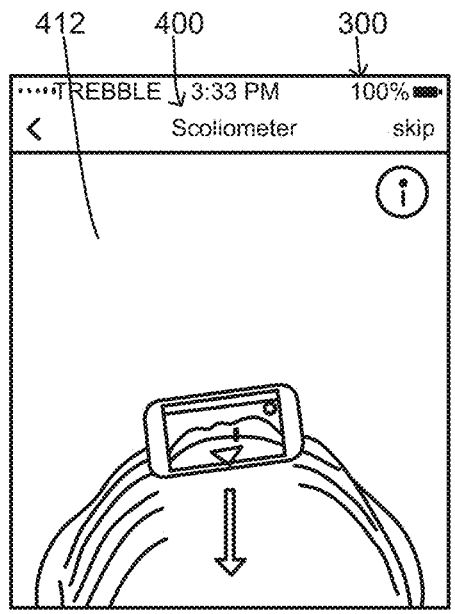
FIG. 4F illustrates a variation of a graphical user interface.

FIG. 4F illustrates that the body condition screening application 400 can include instruction content 412 with the various features shown on the GUI 300. For example, the instruction content 412 can provide instructions for how the subject and/or the data acquisition device user (e.g., "The patient needs to be shirtless or in a bra. You need enough light to take a crisp and clear recording."), where the scoliometer can be the same or different data acquisition device as the device having the GUI 300. The content 412 can show an example image or video of how the scoliometer should be used to take a proper measurement of the curvature of the subject's spine.

Figure 4G:
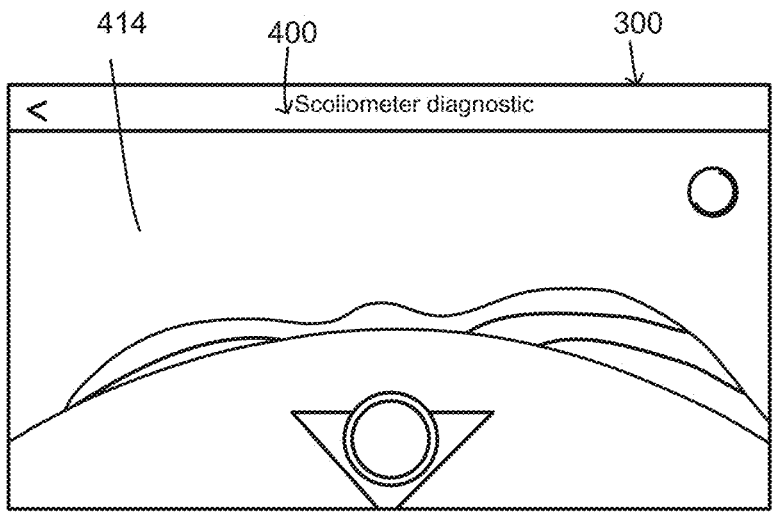
FIG. 4G illustrates a variation of a graphical user interface.

FIG. 4G illustrates that the body condition screening application 400 can include instruction content 414 with the various features shown on the GUI 300. For example, the instruction content 414 can show the real-time data capture while taking a measurement with the scoliometer (e.g., the data acquisition device 102).

Figure 5A:
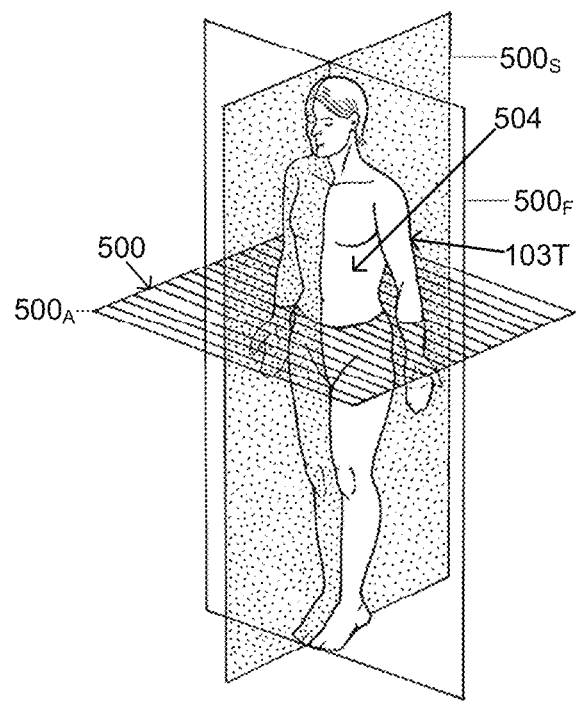
FIG. 5A illustrates a variation of a target object.
Figure 5B:
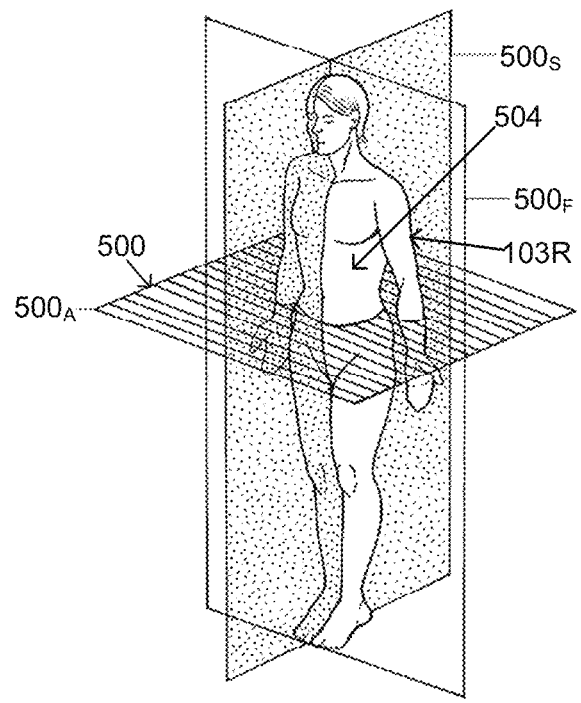
FIG. 5B illustrates a variation of a reference object.

FIGS. 1A-4G illustrate that the method 200 can be used to diagnose any body condition and to treat the diagnosed body conditions. For example, the method 200 can involve diagnosing a subject's scoliosis and designing a scoliosis brace to treat the diagnosed scoliosis. Starting with operation 202 of method 200, the diagnosis operation 202 can involve acquiring, via the data acquisition device 102, one or multiple images of a subject 103T (also referred to as the target object 103T). The data acquired can be, for example, x-rays, MRI images, CT scans, or any other body image, including any combination of image modalities. For example, FIG. 5A illustrates that the diagnosis of any condition (e.g., scoliosis) can involve, via operation 202, acquiring one or multiple images of the target object 103T in one or multiple planes 500. For example, FIG. 5A illustrates that operation 202 can involve acquiring zero, one, or multiple images in the frontal plane $500_F$ (also referred to as the coronal plane), acquiring zero, one, or multiple images in the sagittal plane $500_S$ (also referred to as the lateral plane), acquiring zero, one, or multiple images in the axial plane $500_A$ (also referred to as the transverse plane), or any combination thereof, or any two mutually perpendicular planes, or any three mutually perpendicular planes. For example, the method 200 (e.g., in operation 202) can involve using whatever image data is available. As another example, the method 200 (e.g., in operation 202) can involve using or acquiring whatever image data allows a complete analysis of the body or a region of the body. For example, the method 200 (e.g., in operation 202) can involve using or acquiring a 360 degree view of the subject 103T, or any acquisition example listed in table 600A (e.g., frontal x-ray, sagittal x-ray, axial x-ray). For example, for any given subject (e.g., subject 103T), the method 200 (e.g., in operation 202) can indicate or be programmed to acquire three fully body x-rays, one in the frontal plane $500_F$, one in the sagittal plane $500_S$, and one in the axial plane $500_A$. As another example, FIG. 5A illustrates that the target object 103T can be represented as a whole body (or any portion thereof) MRI image of the target object 103T, acquired, for example, from an MRI scan, where the frontal, sagittal, and axial planes $500_F$, $500_S$, and $500_A$ in FIG. 5A can be any number and combination of slices in the frontal, sagittal, and axial planes $500_F$, $500_S$, and $500_A$, respectively, of the target object 103T depicted in the MRI image (e.g., the three planes $500_F$, $500_S$, and $500_A$ shown in FIG. 5A). FIG. 5B illustrates an exemplary reference object 103R, which can be, for example, a compilation of every data acquisition of every target object 103T.

FIGS. $6A_1$ and $6A_2$ illustrate a table 600A (split across two pages due to page size limitations) of various exemplary data that can be acquired in operation 202, examples of one or multiple physical parameters 502 (also referred to as fit parameters) that can be determined from the acquired data in operation 202, examples of one or multiple body conditions 504 that can be diagnosable and that can be diagnosed from the physical parameters 502, examples of device measurements 506 (also referred to as device fit requirements) for fitting the device 150 to the target object 103T in operation 204, and examples of devices 150 that can be designed in operation 204 to treat the body conditions 504 that are diagnosed in operation 202. Although various examples are listed in the table spanning FIGS. $6A_1$ and $6A_2$, these examples are non-limiting. Operation 202 can use x-rays, MRI scans, CT scans, or any other modality suitable for determining the physical parameters 502 of the target object 103T. For example, MRI is good for soft tissue visualization, and CT and x-ray are both good for bone visualization (e.g., although CT scans can be more accurate). Any image of the target 103T can be taken using any of these modalities. For example, any combination of image modalities listed in FIGS. $6A_1$ and $6A_2$ can be used when imaging the target object 103T. Further, many of the measurements listed in the table in FIGS. $6A_1$ and $6A_2$ include topology.

FIGS. $6B_1$-$6B_3$ illustrate a table 600B (split across three pages due page size limitations) of the examples of one or multiple body conditions 504 listed in table 600A, examples of primary and secondary conditions associated with the body conditions 504 (e.g., any body condition 504 or any diagnosed body condition (e.g., body conditions 504) can be a primary condition), example thresholds for treatment of the example primary conditions, the examples of devices 150 listed in table 600A that can be designed in operation 204 to treat the body conditions 504 that are diagnosed in operation 202, example adjustments of physical parameters 502 from parameter first values to parameter second values (also referred to as first and second positions, respectively, of the target object 103T) that the devices 150 can cause, and examples of monitoring data that can be collected during treatment. If the devices 150 do not cause desired position change (e.g., from parameter first to second values), the devices 150 can be adjusted or re-design to effected the desired position change. With patient growth and/or sufficient time using the devices 150 while in the second position (e.g., while the parameter value is the second value), the next treatment step can generally be taken to change the parameter to a parameter third value. The devices 150 designed by the method 200 can prevent progression and correct body conditions 504 while using the devices 150 (e.g., while in a scoliosis brace).

For example, regarding data acquisition in operation 202 (e.g., examples in table 600A), FIGS. 7A-7D illustrate that a frontal torso x-ray 702 (FIG. 7A), a sagittal torso x-ray 704 (FIG. 7B), a sagittal torso x-ray 704 (FIG. 7C), and an axial torso x-ray 708 (FIG. 7D) of the target object 103T can be acquired in operation 202 using the data acquisition device 102.

FIGS. 7A-7D illustrate that the diagnosis operation 202 can involve electronically determining, via a computer processor (e.g., a processor of the system 100), one or multiple physical parameters 502 (also referred to as physical characteristics) of the subject 103T from the acquired data (e.g., x-rays 702, 704, 706, and 708). For example, operation 202 can involve measuring dimensions and angles in the acquired data (e.g., x-rays 702, 704, 706, and 708) and can involve deriving additional data (e.g., ratios of measured dimensions, ratios of measured angles) from the measured dimensions and angles. As another example, operation 202 can involve measuring dimensions and angles identifiable or measurable in the acquired data (e.g., x-rays 702, 704, 706, and 708) and can involve deriving additional data (e.g., ratios of measured dimensions, ratios of measured angles) from the measured dimensions and angles. When the method 200 screens for scoliosis, for example, the physical parameters 502 that are determined in operation 202 can include, for example, the spine curvature in degrees, body dimensions such as chest measurements, hip measurements, and torso measurements (e.g., horizontal torso measurements of the hip, waist, underbust) in the frontal and sagittal planes, and the distance from the apex of the spinal curves to the central sacral vertical line (CSVL), or any combination thereof.

For example, FIGS. 7A-7D illustrate various exemplary physical parameters 502 that can measured from the acquired data (e.g., x-rays 702, 704, 706 and 708) when the method 200 screens for a body condition 504 involving the spine of the subject 103T (e.g., scoliosis) in operation 202.

FIG. 7A illustrates, for example, that dimensions (e.g., X, $X_1$, and $X_2$) angles (e.g., $\Theta_{1X}$ and $\Theta_{2X}$) can be electronically measured from frontal x-rays of the subject 103T (e.g., from x-ray 702), where dimension X can be width of the pelvis in the frontal plane dimension $X_1$ can be width of the waist in the frontal plane, and dimension $X_2$ can be width of the chest in the frontal plane in FIG. 7A, and where angle $\Theta_{1X}$ can be Cobb angle of the lumbar curve in the frontal plane and angle $\Theta_{2X}$ can be Cobb angle of the thoracic curve in the frontal plane in FIG. 7A.

FIG. 7A further illustrates that the physical parameters 502 measured on x-ray 702 (e.g., dimensions X, $X_1$, and $X_2$ and angles $\Theta_{1X}$ and $\Theta_{2X}$) can be electronically shown (e.g., graphically) on the x-ray 702.

FIG. 7B illustrates, for example, that dimensions (e.g., $Y_1$, $Y_2$, $Y_3$, and $Y_4$) and angels (e.g., $\Theta_{1Y}$ and $\Theta_{2Y}$) can be electronically measured from sagittal x-rays of the subject 103T (e.g., from x-ray 704), where dimension $Y_1$ can be width of the pelvis in the sagittal plane, dimension $Y_2$ can be width of the torso in the sagittal plane, dimension $Y_3$ can be width of the waist in the sagittal plane, and dimension $Y_4$ can be width of the chest in the sagittal plane in FIG. 7B, and where angle thy can be the angle of lumbar lordosis in the sagittal plane and angle $\Theta_{2Y}$ can be angle of kyphosis in the sagittal plane FIG. 7B. FIG. 7B further illustrates that the physical parameters 502 measured on x-ray 704 (e.g., dimensions $Y_1$, $Y_2$, $Y_3$, and $Y_4$ and angles $\Theta_{1Y}$ and $\Theta_{2Y}$) can be electronically shown (e.g., graphically) on the x-ray 704.

FIG. 7C illustrates, for example, that dimensions (e.g., d) can be electronically measured from sagittal x-rays of the subject 103T (e.g., from x-ray 706), where dimension d in FIG. 7C can be the distance from the apex of the spinal curves to the central sacral vertical line (CSVL).

FIG. 7D illustrates, for example, that dimensions (e.g., a, b, and c) can be electronically measured from axial x-rays of the subject 103T (e.g., from x-ray 708), where dimension a can be the width of the torso in the sagittal plane, dimension b can be the width of the torso in the frontal plane, and dimension c can be the circumference of the torso in FIG. 7D. FIG. 7D further illustrates that the physical parameters 502 measured on x-ray 708 (e.g., dimensions a, b, and c can be electronically shown (e.g., graphically) on the x-ray 708.

FIGS. 7A-7D illustrate that operation 202 can further involve analyzing, via a computer processor (e.g., a processor of the system 100), the physical parameters 502 (e.g., the measured and/or derived physical parameters 502 derived from x-rays 702, 704, 706, and/or 708) to diagnose the body conditions 504 of the patient. For example, operation 202 can determine, upon an analysis of the physical parameters 502 of FIGS. 7A-7D, that the target object 103T has a body condition 504 and that the body condition 504 is scoliosis. Operation 202 can diagnose the body condition 504 from the physical parameters 502 by determining, for example, whether or not one or multiple diagnosis thresholds for the body condition 504 have been reached or exceeded. Each diagnosis threshold can be a threshold for one of the physical parameters 502 (e.g., one of the physical parameters 502 shown in x-rays 702, 704, 706, and 708), can be a threshold for a parameter derived from one of the physical parameters (e.g., a ratio between two of the physical parameters 502 shown in x-rays 702, 704, 706, and 708), or both.

For example, where the body condition 504 that is being screened for is scoliosis, the scoliosis diagnosis threshold can be a Cobb angle of about 15 degrees to about 20 degrees, or more broadly, a Cobb angle of about 10 degrees to about 20 degrees, or more broadly, a Cobb angle of about 5 degrees to about 20 degrees, including every 1 degree increment within and over these ranges, and such that the term about in these diagnosis thresholds can be the angle plus or minus 0.5 degrees. For example, a Cobb angle of about 15 degrees can include any angle between 14.5 degrees and 15.5 degrees, including every 0.1 degree increment within this range (e.g., 14.5 degrees, 15.0 degrees, 15.5 degrees). The Cobb angle can be determined by measuring the angle of the spine of the target object 103T. For example, using the physical parameters 502 shown in FIGS. 7A-7D, the Cobb angle can be determined by measuring the Cobb angle in the frontal plane $500_F$ shown in FIG. 7A, where the frontal plane Cobb angle can include a lumbar Cobb angle, a thoracic Cobb angle, or both. There can be two Cobb angles, one for lumbar curve and one for thoracic, or just one for lumbar or one for thoracic, as every curve is different.

Operation 202 can analyze, via a computer processor, whether the diagnosis threshold is reached or exceeded. If the diagnosis threshold is reached or exceeded, operation 202 can diagnose the body condition 504. For example, for scoliosis, upon determining that the Cobb angle of the spine of the target object is over about 15-20 degrees, over about 10-20 degrees, or over about 5-20 degrees, operation 202 can diagnose that the target object 103T has scoliosis. For example, where FIG. 7A illustrates a frontal plane Cobb angle of about 22 degrees and the scoliosis diagnosis threshold is a Cobb angle of about 20 degrees, operation 202 can diagnose scoliosis. As another example, where FIG. 7A illustrates a frontal plane Cobb angle of about 20 degrees and the scoliosis diagnosis threshold is a Cobb angle of about 20 degrees, operation 202 can diagnose scoliosis. As another example, where FIG. 7A illustrates a frontal plane Cobb angle of about 17 degrees and the scoliosis diagnosis threshold is a Cobb angle of about 15 degrees, operation 202 can diagnose scoliosis. As yet another example, where FIG. 7A illustrates a frontal plane Cobb angle of about 5 degrees and the scoliosis diagnosis threshold is a Cobb angle of about 5 degrees, operation 202 can diagnose scoliosis.

Upon diagnosing the body condition 504, which is also referred to as the primary body condition, operation 202 can determine whether or not the diagnosed primary condition (e.g., scoliosis) is an indicator for a secondary condition. For example, where the primary condition is scoliosis (e.g., determined by comparing the physical parameters 502 to a frontal plane Cobb angle threshold), the secondary condition can be hypo or hyper kyphosis. For example, upon diagnosing the primary condition (e.g., scoliosis), operation 202 can indicate that the target object 103T may have the secondary condition (e.g., hypo or hyper kyphosis) upon a determination that the target object 103T has the primary condition. The diagnosis of the primary condition can, for example, trigger the method 200 in operation 202 to screen (e.g., analyze) the acquired data for the secondary condition.

After diagnosing the body condition 504 in operation 202, operation 204 can involve designing a device 150 to engage with (e.g., treat) the body condition 504. The device 150 can be designed using the physical parameters 502 determined from the acquired data (e.g., x-rays 702, 704, 706, and 708), and based on the fit requirements 506 for the device 150 to treat the body condition 504. As another example, the device 150 can be designed based on the physical parameters 502, based on the device fit requirements, and based on the parameters of the body condition 504 and/or parameters of the device 150 to be monitored.

The body condition 504 can be treated, for example, by adjusting one or multiple parameters of or associated with the body condition 504 from a parameter first value to a parameter second value. For example, the device 150 can be designed to adjust any of the physical parameters 502 from a first value (e.g., the values measured and shown in x-rays 702, 704, 706, and 708) to a second value, where the second value can be selected by operation 204, via a processor (e.g., a processor of the system 100), to stabilize or reduce the magnitude of the body condition 504. For example, where the body condition 504 is scoliosis, the device 150 designed in operation 204 can be a scoliosis brace, and the scoliosis brace can be designed in operation 204 to reduce the Cobb angle of the target object 103T from a Cobb angle first value to a Cobb angle second value, where the Cobb angle second value can be about 5 degrees to about 12 degrees less than the Cobb angle first value, including every 1 degree increment within this range (e.g., 5 degrees, 12 degrees). The Cobb angle first value can be the Cobb angle determined in operation 202 from the acquired data (e.g., x-rays 702, 704, 706, and 708). The device 150 can be designed in operation 204 to change the parameter first value (e.g., Cobb angle first value) to the parameter second value (e.g., Cobb angle second value) over a time period ranging, for example, from 2 months to 12 months, including every 1 week increment within this range and including every 1 month increment within this range.

The parameter first value can be the initial value of the parameter and the parameter second value can be the final desired value of the parameter or any intermediate value between the initial value and the final desired value. For example, operation 204 can design the device 150 to adjust the parameter first value to the parameter second value in one or multiple stages, including 1 to 5 or more stages, 1 to 10 or more stages, 1 to 100 or more stages, including every 1 stage increment within these ranges (e.g., 1 stage, 2 stages, 5 stages, 10 stages, 100 stages, or more stages), where the number of stages can be dependent on the severity of the diagnosed condition 504 and on the amount that the parameter first value is being changed by the device 150. The multiple stages can be treatment stages such that operation 204 can design the device 150 such that the same device 150 can be used by the target object 103T for all of the treatment stages. The device 150 can have a device configuration specific to each one of the treatment stages, where the device 150 can be adjusted to have the device configuration specific to each one of the treatment stages (e.g., via tightening a strap, loosening a strap).

The number of treatment stages can be selected to optimize the comfort for the target object 103T, the speed of the treatment, or the efficacy of the treatment while moving a parameter first value to a parameter second value via the device 150. For example, in analyzing the physical parameters 502 of FIGS. 7A-7D, operation 204 can design the device 150 to have a first, second, third, and fourth treatment stage. The first treatment stage can be the initial treatment stage, where the device 150 can be configured to move the parameter first value to a parameter second value (e.g., from a first Cobb angle to a second Cobb angle). After the first stage of treatment, the device 150 can be adjusted to move the parameter second value to a parameter third value (from the second Cobb angle to a third Cobb angle). After the second stage of treatment, the device 150 can be adjusted to move the parameter third value to a parameter fourth value (from the third Cobb angle to a fourth Cobb angle). After the third stage of treatment, the device 150 can be adjusted to move the parameter fourth value to a parameter fifth value (from the fourth Cobb angle to a fifth Cobb angle). The parameter first value can be the initial value of the parameter (e.g., Cobb angle) that the device 150 is designed to change. The last parameter value in the treatment series (e.g., the fifth value in this 4-stage treatment example) can be the final desired parameter value in the treatment series. The Cobb angle can decrease from the first Cobb angle to the fifth Cobb angle. For example, where the Cobb angle is measured in FIGS. 7A-7D to be greater than 25 degrees (e.g., 40 degrees), the configuration of the device 150 in the first stage of treatment can be designed to move the Cobb angle from 40 degrees to 25 degrees while the target object 103T is wearing the device 150, the configuration of the device 150 in the second stage of treatment can be designed to move the Cobb angle from 25 degrees to 15 degrees while the target object 103T is wearing the device 150, the configuration of the device 150 in the third stage of treatment can be designed to move the Cobb angle from 15 degrees to 5 degrees while the target object 103T is wearing the device 150, and the configuration of the device 150 in the fourth stage of treatment can be designed to move the Cobb angle from 5 degrees to 0 degrees while the target object 103T is wearing the device 150.

In designing the device 150 in operation 204, the physical parameters 502 that are determined in operation 202 can function as inputs for the design of the device 150, meaning that the device 150 can be designed to fit the target object 103T taking into account the target object's unique body shape and dimensions (e.g., their physical parameters). In this way, the physical parameters 502 can be used to both diagnose the body condition 504 and to determine the fit parameters of the device 150 that is designed in operation 204 to treat the diagnosed body condition (e.g., scoliosis).

For example, where the GDD is used in operation 204, the physical parameters 502 are the measurements of the target object 103T and the device fit requirements are the fit requirements of the reference object 103R such that in operation 204, the device fit requirements for the reference object 103R are applied to the physical parameters 502 of the target object 103T to create a user-specific device that fits the physical parameters 502 of the user 103T. Using the GDD, the device fit requirements are the dimensions and other features that the device 150 would have to fit the reference object 103R to treat the same body condition 504 in the reference object 103R that was diagnosed in the target object 103T (e.g., the scoliosis that was diagnosed in operation 202 upon analyzing x-rays 702, 704, 706, and 708).

In addition to using the physical parameters 502, operation 204 can also design the device 150 based on the parameters that are going to be monitored, such that the placement of the sensors 152 on the device 150 can be selected so that the sensors 152 can monitor the device 150 and/or the target object 103T in any of the treatment stages of the device 150. As another example, operation 204 can design the device 150 such that the sensors 152 can be removably attachable to the device and design sensor attachment locations on the device 150 for each of the treatment stages of the device 150, where the position of the sensors 152 on the device 150 can be adjusted for each of treatment stages.

With respect to FIGS. 7A-7D and the scoliosis that was diagnosed in operation 202, once the scoliosis brace is designed in operation 204, the scoliosis brace can be created in operation 206, for example, using any manufacturing method, including any of the manufacturing methods disclosed herein (e.g., 3D printing).

With respect to FIGS. 7A-7D and the scoliosis diagnosed in operation 202, once the device 150 is designed in operation 204 and the device 150 is created in operation 206, the body condition 504 and/or the user's use of the device 150 can be monitored, for example, via one or multiple sensors 152. For example, the scoliosis brace designed in operation 204 can be designed with one or multiple sensors 152 (e.g., pressure sensors) that can monitor the pressure applied to the target object 103T via the device 150 when the target object 103T wears the device. When the target object 103 wears the scoliosis brace, the pressure applied to the user can be tracked and stored, for example, in a local memory on the device and/or can be stored on the cloud. This pressure data can be used to determine, for example, when each treatment stage is complete. Any treatment stage can be considered complete, for example, when the pressure sensed by the pressure sensor(s) decreases by or increases by 500 Pa to 2000 Pa relative to a first pressure sensed by the pressure sensor at the start of any treatment stage, including every 1 Pa increment within this range (e.g., 500 Pa, 1000 Pa, 2000 Pa), decreases by or increases by 25% to 50% relative to a first pressure sensed by the pressure sensor at the start of any treatment stage, including every 1% increment within this range (e.g., 25%, 35%, 50%), or decreases or increases to a desired or expected pressure, for example, where the desired or expected pressure can be 25% to 50% lower or higher than a first pressure sensed by the pressure sensor at the start of any treatment stage, including every 1% increment within this range (e.g., 25%, 35%, 50%). As another example, the pressure data collected by the device 150 via the sensors 152 can be used to determine how to adjust the scoliosis brace at the start of a next treatment stage so that the scoliosis brace applies the desired pressure to change the Cobb angle as desired. As yet another example, the change in the spine curvature of the target object 103T can be monitored, for example, via sensors 152 of the device 150 and/or via periodic (e.g., every 1 month to 6 month) data acquisitions by the data acquisition device 102 (e.g., of the system 100). For example, the relative positions of the sensors 152 (e.g., of the pressure sensors and/or location sensors) sensors can be monitored or determined in operation 208 to determine the spine curvature of the target object 103T or to estimate the spine curvature of the target object 103T.

Operation 210 can involve determining, via a computer processor (e.g., a processor of the system 100), whether to continue treatment based on monitoring data related to the scoliosis and/or the scoliosis brace, a reassessment of the scoliosis, or both. As described above, the determination to continue treatment can be made, for example, based partly or entirely on an observed anatomical change of the subject (e.g., a change in any of the physical parameters 502). For example, for scoliosis, the observed anatomical change can be a change in the Cobb angle, for example, a threshold decrease in the Cobb angle of about 5 degrees to about 12 degrees. As another example, the threshold decrease in the Cobb angle can be dependent on the device 150 that is designed and the treatment stages. For example, in the four-stage scoliosis brace described above, the threshold decrease can correspond to the desired decrease in the Cobb angle in each of the stages. For example, in the first stage the Cobb angle is decreased from 40 degrees to 25 degrees, so the threshold decrease in the first stage can be 15 degrees, in the second stage the Cobb angle is decreased from 25 degrees to 15 degrees, so the threshold decrease in the Cobb angle in the second stage can be 10 degrees, in the third stage the Cobb angle is decreased from 15 degrees to 5 degrees, so the threshold decrease in the Cobb angle in the third stage can be 10 degrees, and in the fourth stage the Cobb angle is decreased from 5 degrees to 0 degrees, so the threshold decrease in the Cobb angle in the fourth stage can be 5 degrees. However, any decrease between any two Cobb angle values (e.g., between a first Cobb angle value to a second Cobb angle value) can be the observed anatomical change. Until the threshold decrease in the anatomical change is observed (e.g., by reassessing the physical parameters 502 of the subject 103T via a data acquisition device 102 of the system 100 and/or via one or more sensors 152 of the device 150, and, for example, re-determining the physical parameters 502 shown in x-rays 702, 704, 708), operation 210 can make a determination to continue treatment, where operation 212 can determine whether to maintain the treatment (e.g., keep the device 150 at the current treatment stage configuration, for example, keep the dimensions of the device 150 the same) or change the treatment (e.g., adjust the device 150 to the next treatment stage configuration, for example, change the dimensions of the device 150). When the threshold decrease in the anatomical change is observed, operation 210 can make a decision to terminate treatment, after which the method 200 can make the decisions described elsewhere in this disclosure with respect to operations 216 and 218.

As another example, the determination to continue treatment can be made when the device 150 achieves a desired anatomical change of the subject 103T. For example, for scoliosis, the desired anatomical change can be a desired threshold change of the Cobb angle, which can be considered achieved, for example, when, after the subject 103T removes the scoliosis brace, the Cobb angle of the subject 103T stays at the desired Cobb angle (i.e., the Cobb angle that the scoliosis brace forces or urges the subjects spine to have when the subject 103T wears the scoliosis brace), plus or minus 5 degrees, for a period of 1 day to 14 days, including every 1 day increment within this range. Until the desired anatomical change of the subject 103T achieved, which can be determined, for example, by reassessing the physical parameters 502 of the subject 103T via a data acquisition device and/or via one or more sensors 152 of the device 150 and re-determining, for example, the physical parameters 502 shown in x-rays 702, 704, 708, operation 210 can make a determination to continue treatment, where operation 212 can determine whether to maintain the treatment (e.g., keep the device 150 at the current treatment stage configuration, for example, keep the dimensions of the device 150 the same) or change the treatment (e.g., adjust the device 150 to the next treatment stage configuration, for example, change the dimensions of the device 150). As another example, the method 200 can determine whether or not the desired anatomical change of the subject 103T is achieved by measuring the pressure sensed by the pressure sensors when the subject 103T puts on the scoliosis brace for the first time after the 1 day to 14 day wear break period. For example, if at a reference time (e.g., time zero) the pressure sensor measures the pressure to be a reference pressure and if after the subject 103T does not wear the scoliosis brace for 1 to 14 days after the reference time (e.g., time zero), the pressure sensed by the pressure sensor(s) does not decrease by or does not increase by 500 Pa to 2000 Pa relative to the reference pressure, including every 1 Pa increment within this range (e.g., 500 Pa, 1000 Pa, 2000 Pa), or does not decrease by or does not increase by 25% to 50% relative to the reference pressure, including every 1% increment within this range (e.g., 25%, 35%, 50%), operation 210 can make a determination to continue treatment. As another example, for scoliosis, the desired anatomical change can be a desired threshold change of the pressure measured or detected by the sensors 152 (e.g., by pressure sensors), which can be considered achieved, for example, when, while the subject 103T wears the scoliosis brace, the pressure sensed by the pressure sensor(s) decreases by or increases by 500 Pa to 2000 Pa relative to a first pressure sensed by the pressure sensor at the start of any treatment stage, including every 1 Pa increment within this range (e.g., 500 Pa, 1000 Pa, 2000 Pa), decreases by or increases by 25% to 50% relative to a first pressure sensed by the pressure sensor at the start of any treatment stage, including every 1% increment within this range (e.g., 25%, 35%, 50%), or decreases or increases to a desired or expected pressure, for example, where the desired or expected pressure can be 25% to 50% lower or higher than a first pressure sensed by the pressure sensor at the start of any treatment stage, including every 1% increment within this range (e.g., 25%, 35%, 50%). Until the desired change in pressure detected by the sensors 152 is achieved (e.g., decreases by or increases by 500 Pa to 2000 Pa, decreases by or increases by 25% to 50% relative to a pressure initially sensed at the start of any treatment stage, or decreases or increases to a desired or expected pressure, for example, where the desired or expected pressure is 25% to 50% lower or higher than the pressure initially sensed at the start of any treatment stage), operation 210 can make a determination to continue treatment.

Operation 210 can make a determination to continue treatment if the desired anatomical change of the subject 103T has not yet been reached, where operation 212 can then determine whether to maintain the treatment (e.g., keep the device 150 at the current treatment stage configuration, for example, keep the dimensions of the device 150 the same) or change the treatment (e.g., adjust the device 150 to the next treatment stage configuration, for example, change the dimensions of the device 150). For example, for the scoliosis brace, when the subject 103T is in the first treatment stage and the device 150 has dimensions to move the Cobb angle from 40 degrees to 25 degrees while the target object 103T is wearing the device 150, operation 210 can determine to keep the dimensions of the scoliosis brace the same if, when the scoliosis brace is worn by the subject 103T, the Cobb angle is corrected to a Cobb angle greater than 25 degrees (but less than 40 degrees), or can determine to keep the dimensions of the scoliosis brace the same if, when the scoliosis brace is worn by the subject 103T, the pressure sensed by the pressure sensor(s) in the first treatment stage does not decrease by or does not increase by 500 Pa to 2000 Pa relative to a reference pressure, including every 1 Pa increment within this range (e.g., 500 Pa, 1000 Pa, 2000 Pa), or does not decrease by or does not increase by 25% to 50% relative to the reference pressure, including every 1% increment within this range (e.g., 25%, 35%, 50%), where the reference pressure can be a pressure detected by the pressure sensor at the start of any treatment stage. When the desired anatomical change is detected via the method 200 (e.g., via sensors 152, via the data acquisition device 102), operation 210 can make a decision to terminate treatment, after which the method 200 can make the decisions described elsewhere in this disclosure with respect to operations 216 and 218.

When operation 212 determines to change the treatment, the device 150 (e.g., the scoliosis brace can be changed as described elsewhere in this disclosure with respect to operation 214.

In progressing through the method 200 for any device 150, the method 200 can return to any previous operation in the method 200 after operation 212, after operation 214, or after operation 216 such that the method 200 can be circular and repeated as desired or as needed, where the initial pass through the method 200 can be the initial state of the subject 103T and each pass through operation 204, for example, can improve the design of the device 150. In this way the device 150 can be continuously improved.

Turning back to FIGS. 5-7D, the data acquired via operation 202 (e.g., x-rays 702, 704, 706, and 708) can be acquired before or after anyone is aware that the subject 103T has the body condition that is ultimately diagnosed (e.g., scoliosis) by operation 202. In other words, operation 202 can be a blind screening of the subject 103T or can be a targeted screening of the subject 103T, or any both, where a blind screening checks the subject 103T, via operation 202, for one or multiple body conditions 504 without any previous information as to whether the subject 103T has or does not have the body conditions 504 being screened for, and where a targeted screening checks the subject 103T, via operation 202, for one or multiple body conditions 504 based on information or data received that the subject 103T may have or should be checked for the body conditions 504 being screened for in operation 202 (e.g., such data can include advice from a medical professional or can be, for example, a secondary condition that is indicated from a primary condition detected by operation 202). For example, the data acquired via operation 202 (e.g., x-rays 702, 704, 706, and 708) can be acquired to screen the subject 103T for any number of body conditions, including scoliosis. As another example, the data acquired via operation 202 (e.g., x-rays 702, 704, 706, and 708) can be acquired to screen the subject 103T for a specific body condition, for example, scoliosis, such that the data acquired via operation 202 (e.g., x-rays 702, 704, 706, and 708) is acquired to diagnose the extent of a body condition that the subject 103T already knows they have or that someone else (e.g., a medical professional such as a doctor) has already diagnosed.

FIGS. 8A-8F illustrate that a frontal x-ray 802 (FIG. 8A), a frontal picture 804 (FIG. 8B), a sagittal x-ray 806 (FIG. 8C), a sagittal picture 808 (FIG. 8D), a sagittal picture 810 (FIG. 8E), and an axial x-ray 810 (FIG. 8E), or any combination thereof, of a leg of the target object 103T can be acquired in operation 202 using the data acquisition device 102. FIGS. 8A-8F illustrate various exemplary physical parameters 502 that can measured from the acquired data (e.g., images 802, 804, 806, 808, 810, 812) when the method 200 screens for a body condition 504 in the leg (e.g., for a condition involving the knee) in operation 202.

FIG. 8A illustrates, for example, that dimensions (e.g., $Y_1$, $Y_2$, $Y_3$, and L) and angles (e.g., $\Theta$) can be electronically measured from frontal x-rays of a leg of the subject 103T (e.g., from x-ray 802), where dimension $Y_1$ can be the horizontal width of the lower leg in the frontal plane, dimension $Y_2$ can be the horizontal width of the knee in the frontal plane, dimension $Y_3$ can be the horizontal width of the upper leg in the frontal plane, and dimension L can be the length of the leg that the brace must cover in FIG. 8A, and where angle $\Theta$ can be the angle between the lower and upper leg in the frontal plane in FIG. 8A. FIG. 8A further illustrates that the physical parameters 502 measured on x-ray 802 (e.g., dimensions $Y_1$, $Y_2$, $Y_3$, and L and angle $\Theta$) can be electronically shown (e.g., graphically) on the x-ray 802.

FIG. 8B illustrates, for example, that dimensions (e.g., $X_1$, $X_2$, $X_3$, and L) and angles (e.g., $\Theta$) can be electronically measured from frontal pictures of a leg of the subject 103T (e.g., from picture 804), where dimension $X_1$ can be the horizontal width of the upper leg in the frontal plane, dimension $X_2$ can be the horizontal width of the knee in the frontal plane, dimension $X_3$ can be the horizontal width of the lower leg in the frontal plane, and dimension L can be the length of the leg that the brace must cover in FIG. 8B, and where angle Θ can be the angle between the lower and upper leg in the frontal plane in FIG. 8B. FIG. 8B further illustrates that the physical parameters 502 measured on picture 804 (e.g., dimensions $X_1$, $X_2$, $X_3$, and L and angle Θ) can be electronically shown (e.g., graphically) on the picture 804. FIG. 8B further illustrates that the same picture (e.g., picture 804) can be displayed twice on the GUI 300 to show different dimensions without crowding the picture (e.g., picture 804) with data.

FIG. 8C illustrates, for example, that dimensions (e.g., X, $X_1$, and $X_2$) and angles (e.g., Θ) can be electronically measured from sagittal x-rays of a leg of the subject 103T (e.g., from x-ray 806), where dimension X can be the width of the lower leg in the sagittal plane, dimension $X_1$ can be the width of the knee in the sagittal plane, and dimension $X_2$ can be the width of the upper leg in the sagittal plane in FIG. 8C, and where angle Θ can be the angle between the lower leg and the upper leg in the sagittal plane in FIG. 8C. FIG. 8C further illustrates that the physical parameters 502 measured on x-ray 806 (e.g., dimensions X, $X_1$, and $X_2$ and angle Θ) can be electronically shown (e.g., graphically) on the x-ray 806.

FIG. 8D illustrates, for example, that dimensions (e.g., $X_1$, $X_2$, $X_3$, and L) can be electronically measured from sagittal pictures of a leg of the subject 103T (e.g., from picture 808), where dimension $X_1$ can be the width of the upper leg in the sagittal plane, dimension $X_2$ can be the width of the knee in the sagittal plane, dimension $X_3$ can be the width of the lower leg in the sagittal plane, and dimension L can be the length between where $X_1$ and $X_3$ are measured. FIG. 8D further illustrates that the physical parameters 502 measured on picture 808 (e.g., dimensions $X_1$, $X_2$, $X_3$, and L) can be electronically shown (e.g., graphically) on the picture 808.

FIG. 8E illustrates, for example, that angles (e.g., Θ) can be electronically measured from sagittal pictures of a leg of the subject 103T (e.g., from picture 810), where angle Θ can be the angle between the upper and lower leg in FIG. 8E. FIG. 8D further illustrates that the physical parameters 502 measured on picture 808 (e.g., dimensions $X_1$, $X_2$, $X_3$, $C_1$, $C_2$, and $C_3$) can be electronically shown (e.g., graphically) on the picture 808.

FIGS. 8A-8D illustrate that when the images of the subject's leg are acquired, the subject's leg can be straight (e.g., FIGS. 8A, 8B, and 8D) or bent (e.g., FIGS. 8c and 8E).

FIG. 8F illustrates, for example, that dimensions (e.g., X, Y, and C) can be electronically measured from axial x-rays of the subject 103T (e.g., from x-ray 812), where dimension X can be the sagittal width of the knee or leg, dimension Y can be the frontal width of the knee or leg, and dimension C can be the circumference of the knee or leg in FIG. 8F. FIG. 8F further illustrates that the physical parameters 502 measured on x-ray 812 (e.g., dimensions X, Y, and C and angle Θ) can be electronically shown (e.g., graphically) on the x-ray 812.

FIGS. 9A and 9B illustrate that a frontal x-ray 902 (FIG. 9A) and a sagittal x-ray 904 (FIG. 9B), or any combination thereof, of a pelvis of the target object 103T can be acquired in operation 202 using the data acquisition device 102. FIGS. 9A and 9B illustrate various exemplary physical parameters 502 that can measured from the acquired data (e.g., images 902 and 904) when the method 200 screens for a body condition 504 in the pelvis (e.g., for a condition involving the hips) in operation 202.

FIG. 9A illustrates, for example, that dimensions (e.g., x, y, a, b, L) and angles (e.g., Θ) can be electronically measured from frontal x-rays of a pelvis of the subject 103T (e.g., from x-ray 902), where dimension x can be the width of the hip joint cavity in the frontal plane, dimension y can be the height of the hip joint cavity in the frontal plane, dimension a can be the width of the pelvis in the frontal plane, dimension b can be the height of the pelvis in the frontal plane, and dimension L can be the length of the femoral neck in the frontal plane in FIG. 9A, and where angle Θ can be the Q angle of the hip in FIG. 9A. FIG. 9A further illustrates that the physical parameters 502 measured on x-ray 902 (e.g., dimensions x, y, a, b, L and angle Θ) can be electronically shown (e.g., graphically) on the x-ray 902.

FIG. 9B illustrates, for example, that dimensions (e.g., x, y, $L_1$, and $L_2$) can be electronically measured from sagittal x-rays of a pelvis of the subject 103T (e.g., from x-ray 904), where dimension x can be the width of the hip joint in the sagittal plane, dimension y can be the height of the hip joint in the sagittal plane, dimension $L_1$ can be the width of the pelvis in the sagittal plane, and dimension $L_2$ can be length of the femoral neck in the sagittal plane in FIG. 9B. FIG. 9B further illustrates that the physical parameters 502 measured on x-ray 904 (e.g., dimensions x, y, $L_1$, and $L_2$) can be electronically shown (e.g., graphically) on the x-ray 904.

FIGS. 10A-10C illustrate that a frontal x-ray 1002 (FIG. 10A), a sagittal x-ray 1004 (FIG. 10B), and an axial x-ray 1006 (FIG. 10C), or any combination thereof, of a lower leg of the target object 103T can be acquired in operation 202 using the data acquisition device 102. FIGS. 10A-10C illustrate various exemplary physical parameters 502 that can measured from the acquired data (e.g., images 1002, 1004, and 1006) when the method 200 screens for a body condition 504 in the lower leg (e.g., for a condition involving a foot) in operation 202.

FIG. 10A illustrates, for example, that angles (e.g., Θ and $Θ_1$) can be electronically measured from frontal x-rays of a leg of the subject 103T (e.g., from x-ray 1002), where angle Θ can be the medial angle between the foot and the lower leg in the frontal plane and angle $Θ_1$ can be the lateral angle between the foot and the lower leg in the frontal plane in FIG. 10A. FIG. 10A further illustrates that the physical parameters 502 measured on x-ray 1002 (e.g., angles Θ and $Θ_1$) can be electronically shown (e.g., graphically) on the x-ray 1002.

FIG. 10B illustrates, for example, that dimensions (e.g., y, $y_1$, $y_2$, L, and h) and angles (e.g., Θ) can be electronically measured from sagittal x-rays of a leg of the subject 103T (e.g., from x-ray 1004), where dimension y can be the width of the toes in the sagittal plane, dimension $y_1$ can be the width of the midfoot in the sagittal plane, dimension $y_2$ can be the width of the upper foot in the sagittal plane, dimension L can be the length of the foot in the sagittal plane, and dimension h can be the arch height of the foot in the sagittal plane in FIG. 10B, and where angle Θ can be the sagittal angle between the foot and the lower leg in FIG. 10B. FIG. 10B further illustrates that the physical parameters 502 measured on x-ray 1004 (e.g., dimensions y, $y_1$, $y_2$, L, and h and angle Θ) can be electronically shown (e.g., graphically) on the x-ray 1004.

FIG. 10C illustrates, for example, that dimensions (e.g., y, $y_1$, $y_2$, and $y_3$) and angles (e.g., Θ) can be electronically measured from sagittal x-rays of a leg of the subject 103T (e.g., from x-ray 1006), where dimension y can be the width of the upper foot in the axial plane, dimension $y_1$ can be the width of the midfoot in the axial plane, dimension $y_2$ can be the width of the metatarsals in the axial plane, and dimension $y_3$ can be the width of the toes in the axial plane, in FIG. 10C, and where angle Θ can be the angle between the big toe and the rest of the foot in the axial plane in FIG. 10C. FIG. 10C further illustrates that the physical parameters 502 measured on x-ray 1006 (e.g., dimensions y, $y_1$, $y_2$, and $y_3$ and angle Θ) can be electronically shown (e.g., graphically) on the x-ray 1006.

FIGS. 11A-11C illustrate that a frontal picture 1102 (FIG. 11A), a sagittal picture 1104 (FIG. 11B), and an axial picture 1106 (FIG. 10C), or any combination thereof, of an arm of the target object 103T can be acquired in operation 202 using the data acquisition device 102. FIGS. 11A-11C illustrate various exemplary physical parameters 502 that can measured from the acquired data (e.g., images 1102, 1104, and 1106) when the method 200 screens for a body condition 504 in the arm (e.g., for a condition involving the upper arm, elbow, or lower arm) in operation 202.

FIG. 11A illustrates, for example, that dimensions (e.g., $X_1$, $X_2$, and $X_3$) and angles (e.g., Θ) can be electronically measured from frontal pictures of the subject 103T (e.g., from picture 1102), where dimension $X_1$ can be width of the upper arm in the frontal plane, dimension $X_2$ can be the width of anther point on the upper arm in the frontal plane, and dimension $X_3$ can be the width of yet another point on the upper arm in the frontal plane in FIG. 11A, and where angle Θ can be the range of motion of the shoulder in the frontal plane in FIG. 11A. FIG. 11A further illustrates that the physical parameters 502 measured on picture 1102 (e.g., dimensions $X_1$, $X_2$, and $X_3$ and angle Θ) can be electronically shown (e.g., graphically) on the picture 1102.

FIG. 11B illustrates, for example, that dimensions (e.g., $X_1$, $X_2$, and $X_3$) and angles (e.g., Θ) can be electronically measured from sagittal pictures of the subject 103T (e.g., from picture 1104), where dimension $X_1$ can be width of the upper arm in the sagittal plane, dimension $X_2$ can be width of the elbow in the sagittal plane, and dimension $X_3$ can be width of the lower arm in the sagittal plane in FIG. 11B, and where angle Θ can be angle between upper and lower arm in FIG. 11B. FIG. 11B further illustrates that the physical parameters 502 measured on picture 1104 (e.g., dimensions $X_1$, $X_2$, and $X_3$ and angle Θ) can be electronically shown (e.g., graphically) on the picture 1104.

FIG. 11C illustrates, for example, that dimensions (e.g., L) can be electronically measured from axial pictures of the subject 103T (e.g., from picture 1106), where dimension L can be length of the arm that the brace must cover in FIG. 11C. FIG. 11C further illustrates that the physical parameters 502 measured on picture 1106 (e.g., dimension L) can be electronically shown (e.g., graphically) on the picture 1106.

For FIGS. 7A-11C, the use of like reference numerals for the physical parameters 502 shown in these figures does not indicate identical physical parameters between the figures. The specific physical parameters 502 for each of these figures is exemplary of the target object 103T and the anatomical location shown and therefore specific to each of these figures, which also further demonstrates that any combination of the acquired images (e.g., those shown in FIGS. 7A-11C) can be acquired and/or analyzed when screening the subject 103T for body conditions 504.

FIGS. 12$A_1$ and 12$A_2$ illustrate that the device 150 can be a scoliosis brace and that the target object 103T can wear the device 150 (e.g., scoliosis brace) to treat scoliosis diagnosed, for example, in operation 202. FIG. 12$A_1$ illustrates that the brace 150 can have two sensors 152, which can be any of the sensors disclosed. For example, the two sensors 152 illustrated in FIG. 12$A_1$ can be pressure sensors that measure the force the user's body exerts against the brace while wearing the device 150. FIG. 12$A_2$ illustrates that the device 150 can have adjustable straps 1202 (e.g., two adjustable straps) that can be adjusted, for example, when the device 150 is modified to accommodate factors such as user growth, user weight gain, user weight loss, straightening or worsening of the diagnosed scoliosis, or any combination thereof.

FIG. 12B illustrates that the device 150 can be a knee brace and that the target object 103T can wear the device 150 (e.g., knee brace) to treat a diagnosed condition involving the knee (e.g., either primary condition or secondary condition).

FIGS. 12$C_1$ and 12$C_2$ illustrate that the device 150 can be a hip implant implanted into the target object 103T. FIG. 12$C_1$ illustrates that the method 200 can design, for example, the acetabular component 1204 (with a liner for engagement with a femoral head), a femoral head 1206, and a femoral stem 1208, and that these components can be implanted into the subject 103T. FIG. 12C2 illustrates that the femoral head 1206 can be screwed into the femur of the subject 103T via screw 1210.

FIG. 12D illustrates that the device 150 can be an orthotic insole that the subject 103T can insert into a shoe to correct, for example, a low arch by raising the user's arch to dotted line 1212 when the user 103T uses the device 150. FIG. 12D further illustrates that the orthotic insole can have a sensor 152 (e.g., pressure sensor) to monitor the pressure exerted against the orthotic by the subject 103T during use.

FIG. 12E illustrates that the device 150 can be an arm brace and that the target object 103T can wear the device 150 (e.g., arm brace) to treat a diagnosed condition involving the arm (e.g., either primary condition or secondary condition).

FIG. 13A illustrates that some or all of the operations of method 200 can be used, for example, to execute method 1300, including operations 1302, 1304, 1306, 1308, 1310, and 1312.

FIG. 13B illustrates that some or all of the operations of method 200 can involve, for example, to execute method 1320, including operations 1322, 1324, and 1326.

The method 200 can include acquiring (e.g., in operation 202), via a data acquisition device, a digital representation of a subject 103T. The method 200 can include measuring (e.g., in operation 202), via a processor, physical parameters (e.g., physical parameters 502 in table 600A) of the subject from the digital representation of the subject. The method 200 can include detecting (e.g., in operation 202), via an analysis of the physical parameters by the processor, a body condition (e.g., a body condition 504 in table 600A) of the subject. The method 200 can include determining, via a processor, fit parameters of the body condition. The method 200 can include determining, via a processor, a treatment parameter of the body condition, where the treatment parameter can be a desired change in at least one of the fit parameters from a parameter first value to a parameter second value. The method 200 can include designing (e.g., in operation 204), based on the fit parameters and the treatment parameter, a body engagement device (e.g., device 150). The body engagement device, when worn or attached to the subject, can engage with the subject to change the parameter first value to the parameter second value (e.g., see the first and second parameter values in table 600B). The fit parameters of the body condition can be dimensions of the subject measured in the measuring step.

Detecting a body condition 504 can involve comparing, via a processor (e.g., of the system 100), the measured physical parameters (e.g., physical parameters 502 that are measured) of the subject to a library of diagnosis thresholds (e.g., see the library of thresholds in table 600B for treating primary conditions) associated with the measured physical parameters, and for each of the measured physical parameters that exceeds its associated diagnosis threshold, detecting the body condition indicated by each of the exceeded diagnosis thresholds. Exceeding a diagnosis threshold can include going above the threshold or going below the threshold.

Detecting a body condition 504 can involve comparing, via a processor (e.g., of the system 100), a measured physical parameter and a diagnosis threshold associated with the measured physical parameter, and upon determining, via the processor, that the measured physical parameter exceeds the diagnosis threshold, detecting the body condition of the subject. The treatment parameter can be the same as the measured physical parameter that is compared to the diagnosis threshold.

Detecting a body condition 504 can involve analyzing symptoms of the body condition provided by the subject. Analyzing symptoms of the body condition can involve asking the subject questions via a questionnaire (e.g., on a computer and/or in person). The questionnaire can include asking the subject if they have any pain and if so where the pain is located. Upon determining that the subject has pain in a body location that overlaps with (e.g., is in the same area or region of the body as) the location of the subject's body where the measured physical parameter is measured, the method 200 can involve lowering or raising the diagnosis threshold by 10% to 50%, including every 1% increment within this range (e.g., 10%, 25%, 50%). Lowering or raising the diagnosis threshold can, for example, make it easier for the method 200 to diagnose the subject with the body condition 504 that is ultimately diagnosed.

The method 200 can involve monitoring (e.g., in operation 208), via a sensor (e.g., sensor 152), the treatment parameter. The method 200 can involve monitoring (e.g., in operation 208), via a sensor (e.g., sensor 152), wear data of the body engagement device. The method 200 can involve receiving (e.g., in operation 208) first data recorded by a sensor on the body engagement device while the subject is wearing the body engagement device. The method 200 can involve redesigning (e.g., in operation 204) the body engagement device to fit the first body condition based on the first data. The method 200 can involve receiving (e.g., in operation 208) second data recorded by the sensor on the body engagement device while the subject is not wearing the body engagement device.

The method 200 can include identifying (e.g., in operation 202), by processing a first digital representation of a subject 103T via a computer, first physical parameters (e.g., physical parameters 502) of the subject associated with the first digital representation and diagnosing, by processing the first physical parameters associated with the first digital representation, a first body condition 504 of the subject. The method 200 can include determining (e.g., in operation 202), via an analysis of the first physical parameters associated with the first digital representation via the computer, a first physical extent of the first body condition. The method 200 can include designing, based on the first physical extent of the first body condition, a first digital 3D model to engage with the first body condition. The first digital 3D model can be designed to at least one of stabilize and change the first physical extent of the first body condition The first digital 3D model, when digitally worn or digitally attached to the digital representation of the subject, can at least one of stabilize and change the first physical extent of the first body condition.

Identifying the first body condition (e.g., in operation 202) can involve comparing, via a computer, the first physical parameters to a library of diagnosis thresholds (e.g., see the library of thresholds in table 600B for treating primary conditions) associated with the first physical parameters, and for each of the first physical parameters that exceeds its associated diagnosis threshold, detecting the first body condition indicated by each of the exceeded diagnosis thresholds. Exceeding a diagnosis threshold can include going above the threshold or going below the threshold.

The method 200 can involve monitoring (e.g., in operation 208), via a sensor (e.g., sensor 152), the treatment parameter. The method 200 can involve monitoring (e.g., in operation 208), via a sensor (e.g., sensor 152), wear data of the body engagement device. The method 200 can involve receiving (e.g., in operation 208) first data recorded by a sensor on the body engagement device while the subject is not wearing the body engagement device. The method 200 can involve receiving (e.g., in operation 208) second data recorded by the sensor on the body engagement device while the subject is wearing the body engagement device. The method 200 can involve redesigning (e.g., in operation 204) the body engagement device to fit the first body condition based on the first data.

The method 200 can include identifying (e.g., in operation 202, for example, in the first iteration of operation 202 or in a second iteration of operation 202), by processing a second digital representation of the subject via a computer, second physical parameters (e.g., parameters 502) of the subject 103T associated with the second digital representation. The method 200 can include comparing (e.g., in operation 202), via a computer, the second physical parameters identified in the second digital representation with the first physical parameters identified in the first digital representation. The method 200 can include detecting, based on the comparison, a difference or a similarity between the second physical parameters identified in the second digital representation and the first physical parameters identified in the first digital representation. Based on the difference or the similarity detected, the method 200 can include redesigning (e.g., in operation 204) the body engagement device to fit the difference or the similarity detected. Redesigning the body engagement device to fit the difference or the similarity detected can involve changing dimensions of the body engagement device or making a new body engagement device.

The method 200 can include identifying (e.g., in operation 202), by processing a second digital representation of the subject via the computer, second physical parameters of the subject associated with the second digital representation. The method 200 can include determining (e.g., in operation 202), via an analysis of the second physical parameters associated with the second digital representation via the computer, a second physical extent of the first body condition.

The method 200 can include comparing (e.g., in operation 202), via a computer, the second physical extent of the first body condition with the first physical extent of the first body condition. The method 200 can include detecting (e.g., in operation 202), based on the comparison, a difference or a similarity between the second physical extent of the first body condition and the first physical extent of the first body condition. Based on the difference or the similarity detected, the method 200 can include redesigning (e.g., in operation 204) the body engagement device to fit the second physical extent of the body condition. Redesigning the body engagement device to fit the second physical extent can involve changing dimensions of the body engagement device or making a new body engagement device. The method 200 can include re-diagnosing (e.g., in operation 202), by processing the second physical parameters associated with the second digital representation, the first body condition of the subject. The method 200 can include diagnosing (e.g., in operation 202), by processing the second physical parameters associated with the second digital representation, a second body condition of the subject. The second body condition can be different from the first body condition.

The method 200 can include determining (e.g., in operation 202), via an analysis of the second physical parameters associated with the second digital representation via the computer, a first physical extent of the second body condition. The method 200 can include designing (e.g., in operation 204), based on the second physical extent of the first body condition, a second digital 3D model to engage with the first body condition. The second digital 3D model can be designed to at least one of stabilize and change the second physical extent of the first body condition. The second digital 3D model, when digitally worn or digitally attached to the digital representation of the subject, can at least one of stabilize and change the second physical extent of the first body condition. The method 200 can include designing (e.g., in operation 204), based on the first physical extent of the second body condition, a third digital 3D model to engage with the second body condition. The third digital 3D model can be designed to at least one of stabilize and change the first physical extent of the second body condition. The third digital 3D model, when digitally worn or digitally attached to the digital representation of the subject, can at least one of stabilizes and changes the first physical extent of the second body condition. Designing the second digital 3D model can involve redesigning (e.g., in operation 204) the first digital 3D model to fit the second physical extent of the first body condition. Redesigning the first digital 3D model to fit the second physical extent of the first body condition can involve changing dimensions of the first digital 3D model. Designing the third digital 3D model can involve designing (e.g., in operation 204) the third digital 3D model to fit the first physical extent of the second body condition. The second digital 3D model can be a model of a first body engagement device and the third digital 3D model can be a model of a second body engagement device. A digital model of the body engagement device include the second digital 3D model and the third digital 3D model.

The method 200 can include determining (e.g., in operation 202), via an analysis of the second physical parameters associated with the second digital representation via the computer, a first physical extent of the second body condition. The method 200 can include designing (e.g., in operation 204), based on the second physical extent of the first body condition and the first physical extent of the second body condition, a second digital 3D model to engage with the first body condition and with second body condition. The second digital 3D model can be designed to at least one of stabilize and change the second physical extent of the first body condition and can at least one of stabilize and change the first physical extent of the second body condition. The second digital 3D model, when digitally worn or digitally attached to the digital representation of the subject, can at least one of stabilize and change the second physical extent of the first body condition and can at least one of stabilize and change the first physical extent of the second body condition. Designing the second digital 3D model can involve redesigning (e.g., in operation 204) the first digital 3D model to fit the first and second body conditions. Redesigning the first digital 3D model to fit the first and second body conditions can involve changing dimensions of the first digital 3D model. Based on the second digital 3D model, the method 200 can include redesigning (e.g., in operation 204) the body engagement device to fit the second physical extent of the first body condition and the first physical extent of the second body condition. Redesigning the body engagement device to fit the second physical extent of the first body condition and the first physical extent of the second body condition can involve changing dimensions of the body engagement device or making a new body engagement device.

The system 100 can have a data acquisition device and a computer, wherein the computer. The computer can analyze a digital representation of a subject acquired from the data acquisition device. The computer can measure, via a processor, physical parameters of the subject from the digital representation of the subject. The computer can detect, based on the analysis of the acquired digital representation of the subject, a body condition of the subject. The computer can determine fit parameters of the body condition. The computer can determine a treatment parameter of the body condition. The treatment parameter can be a desired change in at least one of the fit parameters from a parameter first value to a parameter second value. The computer can design, based on the fit parameters and the treatment parameter, the body engagement device. The body engagement device, when worn or attached to the subject, can engage with the subject to change the parameter first value to the parameter second value.

Every combination of claims is hereby disclosed.

The claims are not limited to the exemplary embodiments shown in the drawings, but instead may claim any feature disclosed or contemplated in the disclosure as a whole. Any elements described herein as singular can be pluralized (i.e., anything described as "one" can be more than one). Any species element of a genus element can have the characteristics or elements of any other species element of that genus. The term "about" or other similar terms (e.g., approximately), if not otherwise stated, can indicate plus or minus 1 unit of whatever increment the term relates to (e.g., degrees, millimeters, centimeters), can indicate plus or minus 1% of whatever value the term is linked to (e.g., degrees, millimeters, centimeters), and/or any reasonable interpretation thereof. Some elements may be absent from individual figures for reasons of illustrative clarity. The above-described configurations, elements or complete assemblies and methods and their elements for carrying out the disclosure, and variations of aspects of the disclosure can be combined and modified with each other in any combination, and each combination is hereby explicitly disclosed. All devices, apparatuses, systems, and methods described herein can be used for medical (e.g., diagnostic, therapeutic or rehabilitative) or non-medical purposes.

What is claimed is:

1. A method of creating a body treatment device and treating a body condition with the body treatment device, the method comprising:

acquiring, via a data acquisition device, a digital representation of a subject;

measuring, via a processor, physical parameters of the subject from the digital representation of the subject;

detecting, via an analysis of the physical parameters by the processor, the body condition of the subject;

determining, via the processor, fit parameters of the body condition;

determining, via the processor, a treatment parameter of the body condition;

designing, based on the fit parameters and the treatment parameter, the body treatment device, wherein the body treatment device, when worn or attached to the subject, engages with the subject to change at least one of the fit parameters from a parameter first value to a parameter second value;

treating the body condition with the body treatment device;

receiving first data recorded by a sensor on the body treatment device while the subject is wearing the body treatment device;

receiving second data recorded by the sensor on the body treatment device while the subject is not wearing the body treatment device; and redesigning the body treatment device to fit the first body condition based on the first data and/or the second data.

2. The method of claim 1, wherein detecting comprises comparing, via the processor, the physical parameters of the subject to a library of diagnosis thresholds associated with the physical parameters, and for each of the physical parameters that exceeds its associated diagnosis threshold, detecting the body condition indicated by each of the exceeded diagnosis thresholds.

3. The method of claim 1, wherein detecting comprises comparing, via the processor, a measured physical parameter and a diagnosis threshold associated with the measured physical parameter, and upon determining, via the processor, that the measured physical parameter exceeds the diagnosis threshold, detecting the body condition of the subject.

4. The method of claim 3, wherein the treatment parameter is the same as the measured physical parameter compared to the diagnosis threshold.

5. The method of claim 3, wherein detecting further comprises analyzing symptoms of the body condition provided by the subject.

6. The method of claim 5, wherein analyzing symptoms of the body condition comprises asking the subject questions via a computer, via a questionnaire, or via both the computer and the questionnaire.

7. The method of claim 6, wherein the questionnaire includes asking the subject if they have any pain and if so where the pain is located.

8. The method of claim 6, wherein upon determining that the subject has pain in a body location that overlaps with the location of the subject's body where the measured physical parameter is measured, lowering the diagnosis threshold by 10% to 50%.

9. The method of claim 1, wherein the fit parameters of the body condition comprise dimensions of the subject measured in the measuring step.

10. The method of claim 1, further comprising monitoring, via the sensor or another sensor, the treatment parameter.

11. The method of claim 1, further comprising monitoring, via the sensor, wear data of the body treatment device, wherein the first data and/or the second data comprises the wear data.

12. The method of claim 11, further comprising comparing the wear data to wear data of another subject.

13. The method of claim 11, wherein the wear data comprises the subject's compliance with a treatment plan.

14. The method of claim 1, wherein the sensor comprises a first sensor, and wherein the method further comprises monitoring, via the first sensor or a second sensor, the body treatment device.

15. The method of claim 14, further comprising monitoring, via the first sensor or the second sensor, the subject.

16. The method of claim 1, wherein redesigning the body treatment device to fit the first body condition based on the first data and/or the second data comprises changing dimensions of the body treatment device or making a new body treatment device.

17. A method of creating a body treatment device and treating a first body condition with the body treatment device, the method comprising:

identifying, by processing a first digital representation of a subject via a computer, first physical parameters of the subject associated with the first digital representation and diagnosing, by processing the first physical parameters associated with the first digital representation, the first body condition of the subject;

determining, via an analysis of the first physical parameters associated with the first digital representation via the computer, a first physical extent of the first body condition;

designing, based on the first physical extent of the first body condition, a first digital 3D model to engage with the first body condition, wherein the first digital 3D model, when digitally worn or digitally attached to the first digital representation of the subject, changes the first physical extent of the first body condition;

treating the first body condition with the body treatment device; and monitoring, via a sensor, wear data of the body treatment device, wherein the body treatment device comprises the sensor.

18. The method of claim 17, wherein identifying the first body condition comprises comparing, via the computer, the first physical parameters to a library of diagnosis thresholds associated with the first physical parameters, and for each of the first physical parameters that exceeds its associated diagnosis threshold, detecting the first body condition indicated by each of the exceeded diagnosis thresholds.

19. The method of claim 17, further comprising monitoring, via the sensor or another sensor, the treatment parameter.

20. The method of claim 17, further comprising receiving first data recorded by the sensor while the subject is not wearing the body treatment device.

21. The method of claim 20, further comprising receiving second data recorded by the sensor while the subject is wearing the body treatment device.

22. The method of claim 21, further comprising redesigning the body treatment device to fit the first body condition based on the first data.

23. The method of claim 17, further comprising:

identifying, by processing a second digital representation of the subject via the computer, second physical parameters of the subject associated with the second digital representation;

comparing, via the computer, the second physical parameters identified in the second digital representation with the first physical parameters identified in the first digital representation;

detecting, based on the comparison, a difference or a similarity between the second physical parameters identified in the second digital representation and the first physical parameters identified in the first digital representation; and based on the difference or the similarity detected, redesigning the body treatment device to fit the difference or the similarity detected.

24. The method of claim 23, wherein redesigning the body treatment device to fit the difference or the similarity detected comprises changing dimensions of the body treatment device or making a new body treatment device.

25. The method of claim 17, further comprising:
identifying, by processing a second digital representation of the subject via the computer, second physical parameters of the subject associated with the second digital representation; and determining, via an analysis of the second physical parameters associated with the second digital representation via the computer, a second physical extent of the first body condition.

26. The method of claim 25, further comprising:
comparing, via the computer, the second physical extent of the first body condition with the first physical extent of the first body condition;

detecting, based on the comparison, a difference or a similarity between the second physical extent of the first body condition and the first physical extent of the first body condition; and based on the difference or the similarity detected, redesigning the body treatment device to fit the second physical extent of the first body condition.

27. The method of claim 26, wherein redesigning the body treatment device to fit the second physical extent comprises changing dimensions of the body treatment device or making a new body treatment device.

28. The method of claim 27, further comprising diagnosing, by processing the second physical parameters associated with the second digital representation, a second body condition of the subject, wherein the second body condition is different from the first body condition.

29. The method of claim 28, further comprising:
determining, via an analysis of the second physical parameters associated with the second digital representation via the computer, a first physical extent of the second body condition;

designing, based on the second physical extent of the first body condition, a second digital 3D model to engage with the first body condition, wherein the second digital 3D model, when digitally worn or digitally attached to the digital representation of the subject, at least one of stabilizes and changes the second physical extent of the first body condition; and designing, based on the first physical extent of the second body condition, a third digital 3D model to engage with the second body condition, wherein the third digital 3D model, when digitally worn or digitally attached to the digital representation of the subject, at least one of stabilizes and changes the first physical extent of the second body condition.

30. The method of claim 29, wherein designing the second digital 3D model comprises redesigning the first digital 3D model to fit the second physical extent of the first body condition.

31. The method of claim 30, wherein redesigning the first digital 3D model to fit the second physical extent of the first body condition comprises changing dimensions of the first digital 3D model.

32. The method of claim 31, wherein designing the third digital 3D model comprises designing the third digital 3D model to fit the first physical extent of the second body condition.

33. The method of claim 31, wherein the second digital 3D model comprises a model of a first body treatment device and the third digital 3D model comprises a model of a second body treatment device.

34. The method of claim 31, wherein a digital model of the body treatment device comprises the second digital 3D model and the third digital 3D model.

35. The method of claim 28, further comprising:
determining, via an analysis of the second physical parameters associated with the second digital representation via the computer, a first physical extent of the second body condition; and designing, based on the second physical extent of the first body condition and the first physical extent of the second body condition, a second digital 3D model to engage with the first body condition and with second body condition, wherein the second digital 3D model, when digitally worn or digitally attached to the second digital representation of the subject, at least one of stabilizes and changes the second physical extent of the first body condition and at least one of stabilizes and changes the first physical extent of the second body condition.

36. The method of claim 35, wherein designing the second digital 3D model comprises redesigning the first digital 3D model to fit the first body condition and the second body condition.

37. The method of claim 36, wherein redesigning the first digital 3D model to fit the first body condition and the second body condition comprises changing dimensions of the first digital 3D model.

38. The method of claim 35, wherein based on the second digital 3D model, the method further comprises redesigning the body treatment device to fit the second physical extent of the first body condition and the first physical extent of the second body condition.

39. The method of claim 38, wherein redesigning the body treatment device to fit the second physical extent of the first body condition and the first physical extent of the second body condition comprises changing dimensions of the body treatment device or making a new body treatment device.

40. The method of claim 27, further comprising re-diagnosing, by processing the second physical parameters associated with the second digital representation, the first body condition of the subject.

41. A body treatment device 3D modeling system, comprising:
a data acquisition device; and
a computer, wherein the computer is configured to:
analyze a digital representation of a subject acquired from the data acquisition device;
measure, via a processor, physical parameters of the subject from the digital representation of the subject;
detect, based on the analysis of the digital representation of the subject, a body condition of the subject;
determine fit parameters of the body condition;
determine a treatment parameter of the body condition;
design, based on the fit parameters and the treatment parameter, the body treatment device, wherein the body treatment device, when worn or attached to the subject, engages with the subject to treat the body condition by changing at least one of the fit parameters from a parameter first value to a parameter second value, wherein the body treatment device, via sensors, is configured to collect wear data of the body treatment device and data of the subject, and wherein the computer or a processor is configured to determine, based on the wear data of the body treatment device, the subject's compliance with a treatment plan.

42. A method of creating a body treatment device and treating a body condition with the body treatment device, the method comprising:

acquiring, via a data acquisition device, a digital representation of a subject;

measuring, via a processor, physical parameters of the subject from the digital representation of the subject;

detecting, via an analysis of the physical parameters by the processor, the body condition of the subject;

determining, via the processor, fit parameters of the body condition;

determining, via the processor, a treatment parameter of the body condition;

designing, based on the fit parameters and the treatment parameter, the body treatment device, wherein the body treatment device, when worn or attached to the subject, engages with the subject to change at least one of the fit parameters from a parameter first value to a parameter second value;

treating the body condition with the body treatment device; and collecting, via a first sensor, data of the subject, wherein the body treatment device comprises the first sensor.

43. The method of claim 42, further comprising collecting, via a second sensor, data of the body treatment device, wherein the body treatment device comprises the second sensor.

* * * * *